(12) United States Patent
Heimberger et al.

(10) Patent No.: US 9,675,633 B2
(45) Date of Patent: Jun. 13, 2017

(54) MIRNA FOR TREATING CANCER AND FOR USE WITH ADOPTIVE IMMUNOTHERAPIES

(71) Applicant: Board of Regents, The University of Texas System, Austin, TX (US)

(72) Inventors: Amy Heimberger, Houston, TX (US); Jun Wei, Houston, TX (US)

(73) Assignee: Board of Regents, The University of Texas System, Austin, TX (US)

(*) Notice: Subject to any disclaimer, the term of this patent is extended or adjusted under 35 U.S.C. 154(b) by 0 days.

(21) Appl. No.: 14/775,667

(22) PCT Filed: Mar. 14, 2014

(86) PCT No.: PCT/US2014/028296
§ 371 (c)(1),
(2) Date: Sep. 11, 2015

(87) PCT Pub. No.: WO2014/152932
PCT Pub. Date: Sep. 25, 2014

(65) Prior Publication Data
US 2016/0022728 A1 Jan. 28, 2016

Related U.S. Application Data

(60) Provisional application No. 61/782,921, filed on Mar. 14, 2013.

(51) Int. Cl.
A61K 48/00 (2006.01)
A61K 31/7105 (2006.01)
C12N 15/113 (2010.01)
A61K 9/127 (2006.01)
A61K 45/06 (2006.01)

(52) U.S. Cl.
CPC .......... *A61K 31/7105* (2013.01); *A61K 9/127* (2013.01); *A61K 45/06* (2013.01); *C12N 15/113* (2013.01)

(58) Field of Classification Search
CPC .................................................. A61K 48/00
USPC ......................................................... 514/44
See application file for complete search history.

(56) References Cited

U.S. PATENT DOCUMENTS

| | | |
|---|---|---|
| 2011/0077288 A1 | 3/2011 | Kauppinen et al. |
| 2012/0172416 A1 | 7/2012 | Velin et al. |
| 2012/0202870 A1 | 8/2012 | Weiner et al. |

FOREIGN PATENT DOCUMENTS

| | | |
|---|---|---|
| WO | WO 2012-006577 | 1/2012 |
| WO | WO 2012-121178 | 9/2012 |

OTHER PUBLICATIONS

Allavena et al., "Anti-inflammatory properties of the novel antitumor agent yondelis (trabectedin): inhibition of macrophage differentiation and cytokine production," *Cancer Res.*, 65:2964-2971, 2005.
Andreopoulos and Anastassiou, "Integrated analysis reveals hsa-miR-142 as a representative of a lymphocyte-specific gene expression and methylation signature," *Cancer Inform.*, 11:61-75, 2012.
Bharali et al. "Organically modified silica nanoparticles: a nonviral vector for in vivo gene delivery and expression in the brain," *PNAS*, 102(32):11539-11544, 2005.
Birks et al., "Survey of microRNA expression in pediatric brain tumors," *Pediatr Blood Cancer*, 56(2):211-216, 2011.
Bjorge et al., "Simultaneous siRNA targeting of Src and downstream signaling molecules inhibit tumor formation and metastasis of a human model breast cancer cell line," *PLoS One*, 6:e19309, 2011.
Bouquet et al., "TGFβ1 inhibition increases the radiosensitivity of breast cancer cells in vitro and promotes tumor control by radiation in vivo," *Clin Cancer Res.*, 17:6754-6765, 2011.
Carthon et al., "Preoperative CTLA-4 blockade: tolerability and immune monitoring in the setting of a presurgical clinical trial," *Clin Cancer Res.*, 16:2861-2871, 2010.
Chan et al., "MicroRNA-21 is an antiapoptotic factor in human glioblastoma cells," *Cancer Res.*, 65:6029-6033, 2005.
Chan et al., "Targeting glioma stem cells by functional inhibition of a pro survival oncomiR-138 in malignant gliomas," *Cell Rep*, 2(3):591-602, 2012.
Chaudhry et al., "Radiation-induced micro-RNA modulation in glioblastoma cells differing in DNA-repair pathways," *DNA Cell Biol.*, 29(9):553-561, 2010.
Chen et al., "Anti-CTLA-4 therapy results in higher CD4+ICOShi T cell frequency and IFN-gamma levels in both nonmalignant and malignant prostate tissues," *Proc Natl Acad Sci USA*, 106:2729-2734, 2009.
Chihara et al., "HIV-1 proteins preferentially activate anti-inflammatory M2-type macrophages," *J Immunol.*, 188:3620-3627, 2012.
Corsten et al., "MicroRNA-21 knockdown disrupts glioma growth in vivo and displays synergistic cytotoxicity with neural precursor cell delivered S-TRAIL in human gliomas," *Cancer Res.*, 67:8994-9000, 2007.
Dai et al., "STAT3 mediates resistance to MEK inhibitor through microRNA miR-17," *Cancer Res.*, 71:3658-3668, 2011.
Doucette et al., "Immune heterogeneity of glioblastoma subtypes: extrapolation from the cancer genome atlas," *Cancer Immunol Res.*, 1:112-122, 2013.
Eulalio et al., "Getting to the root of miRNA-mediated gene silencing," *Cell*, 132:9-14, 2008.
Fecci et al.,"Systemic CTLA-4 blockade ameliorates glioma-induced changes to the CD4+ T cell compartment without affecting regulatory T-cell function," *Clin Cancer Res.*, 13:2158-2167, 2007.
Flavell et al., "The polarization of immune cells in the tumour environment by TGFbeta," *Nat Rev Immunol.*, 10:554-567, 2010.
Friedman et al., "Most mammalian mRNAs are conserved targets of microRNAs," *Genome Res.*, 19:92-105, 2009.

(Continued)

*Primary Examiner* — Kimberly Chong
(74) *Attorney, Agent, or Firm* — Parker Highlander PLLC

(57) ABSTRACT

In some aspects, miRNA for the treatment of cancer are provided. In some embodiments, a miRNA (e.g., miR-124, miR-142, and/or miR-138) may be used to promote or enhance immune destruction of a cancer, or reduce the immune suppression of the cancer, in a subject. In other aspects, the miRNA may be used in, or in combination with, an adoptive immunotherapy.

33 Claims, 43 Drawing Sheets

(56) References Cited

OTHER PUBLICATIONS

Fu et al., "The ICOS/ICOSL pathway is required for optimal antitumor responses mediated by anti-CTLA-4 therapy," *Cancer Res.*, 71:5445-5454, 2011.

Gabriely et al., "MicroRNA 21 promotes glioma invasion by targeting matrix metalloproteinase regulators," *Mol Cell Biol.*, 28:5369-5380, 2008.

Gaur et al., "Downregulation of Pdcd4 by mir-21 facilitates glioblastoma proliferation in vivo," *Neuro Oncol.*, 13:580-590, 2011.

Hashimoto et al., "Serial analysis of gene expression in human monocytes and macrophages," *Blood*, 94:837-844, 1999.

Heimberger et al., "Epidermal growth factor receptor VIII peptide vaccination is efficacious against established intracerebral tumors," *Clin Cancer Res.*, 9:4247-4254, 2003.

Heimberger et al., "Immunotherapy coming of age: what will it take to make it standard of care for glioblastoma?" *Neuro Oncol.*, 13:3-13, 2011.

Heimberger et al., "miR-124 as a novel immunotherapeutic molecule to reverse glioma-mediated immune suppression and enhance anti-tumor clearance," *J Immunother*, 35(9):776, Abstract, 2012.

Heimberger, "Emerging immune therapeutics targeting glioma-mediated immune suppression," Presentation, 2012.

Heusinkveld et al., "Identification and manipulation of tumor associated macrophages in human cancers," *J Transl Med.*, 9:216, 2011.

Huse et al., "Genetically engineered mouse models of brain cancer and the promise of preclinical testing," *Brain Pathol.*, 19:132-143, 2009.

Hussain et al., "The role of human glioma-infiltrating microglia/macrophages in mediating antitumor immune responses," *Neuro Oncol.*, 8:261-279, 2006.

Iliopoulos et al.,"STAT3 activation of miR-21 and miR-181b-1 via PTEN and CYLD are part of the epigenetic switch linking inflammation to cancer," *Mol Cell.*, 39:493-506, 2010.

Kong et al., "Intratumoral mediated immunosuppression is prognostic in genetically engineered murine models of glioma and correlates to immunotherapeutic responses," *Clin Cancer Res.*, 16:5722-5733, 2010.

Kortylewski et al., "In vivo delivery of siRNA to immune cells by conjugation to a TLR9 agonist enhances antitumor immune responses," *Nat Biotechnol.*, 27:925-932, 2009.

Kortylewski et al., "Inhibiting Stat3 signaling in the hematopoietic system elicits multicomponent antitumor immunity," *Nat Med.*, 11:1314-1321, 2005.

Lim et al., "Microarray analysis shows that some microRNAs downregulate large numbers of target mRNAs," *Nature*, 433:769-773, 2005.

Liu et al., "Micro-RNA-138 suppresses epithelial-mesenchymal transition in squamous cell carcinoma cell lines," *Biochem J.*, 440:23-31, 2011.

Löffler et al., "Interleukin-6 dependent survival of multiple myeloma cells involves the Stat3-mediated induction of microRNA-21 through a highly conserved enhancer," *Blood*, 110:1330-1333, 2007.

Lu et al., "Regulation of tumor angiogenesis by EZH2," *Cancer Cell*, 18:185-197, 2010.

Lujambio et al., "Genetic unmasking of an epigenetically silenced microRNA in human cancer cells," *Cancer Res.*, 67:1424-1429, 2007.

Lv et al., "An oncogenic role of miR-142-3p in human T-cell acute lymphoblastic leukemia (T-ALL) by targeting glucocorticoid receptor-$\alpha$ and cAMP/PKA pathways," *Leukemia*, 26:769-777, 2012.

Muraoka et al., "Blockade of TGF-beta inhibits mammary tumor cell viability, migration, and metastases," *J Clin Invest.*, 109:1551-1559, 2002.

Murray, "STAT3-mediated anti-inflammatory signalling," *Biochem Soc Trans.*, 34:1028-1031, 2006.

PCT International Preliminary Report on Patentability issued in International Application No. PCT/US2014/028296, mailed Sep. 15, 2015.

PCT International Search Report and Written Opinion issued in International Application No. PCT/US2014/028296, mailed Jun. 30, 2014.

Pinheiro et al., "Synthetic genetic polymers capable of heredity and evolution," *Science*, 336(6079):341-344, 2012.

Ponomarev et al., "MicroRNA-124 promotes microglia quiescence and suppresses EAE by deactivating macrophages via the C/EBP-$\alpha$-PU.1 pathway," *Nat Med.*, 17:64-70, 2011.

Pramanik et al. "Restitution of tumor suppressor microRNAs using a systemic nanovector inhibits pancreatic cancer growth in mice," *Mol Cancer Ther*, 10:1470-1480, 2011.

Schreiner et al., "Expression of the B7-related molecule ICOSL by human glioma cells in vitro and in vivo," *GLIA*, 44:296-301, 2003.

Scuto et al., "STAT3 inhibition is a therapeutic strategy for ABC-like diffuse large B-cell lymphoma," *Cancer Res.*, 71:3182-3188, 2011.

Silber et al., "miR-124 and miR-137 inhibit proliferation of glioblastoma multiforme cells and induce differentiation of brain tumor stem cells," *BMC Medicine*, 6:14, 2008.

Song et al., "miR-138 suppresses expression of hypoxia-inducible factor 1$\alpha$ (HIF-1$\alpha$) in clear cell renal cell carcinoma 786-O cells," *Asian Pacific J Cancer Prev*, 12:1307-1311, 2011.

Stupp et al., "Radiotherapy plus concomitant and adjuvant temozolomide for glioblastoma," *N Engl J Med.*, 352:987-996, 2005.

Wei et al., "Glioblastoma cancer-initiating cells inhibit T-cell proliferation and effector responses by the signal transducers and activators of transcription 3 pathway," *Mol Cancer Ther.*, 9:67-78, 2010.

Wei et al., "Glioma-associated cancer-initiating cells induce immunosuppression," *Clin Cancer Res.*, 16:461-73, 2010. (Retracted May 1, 2015).

Wei et al., "IT-o8. miR-124 as a novel immunotherapeutic molecule to reverse glioma-mediated immune suppression and enhance anti-tumor clearance," *Neuro Oncol*, 14(suppl6): vi43-vi49, Abstract, 17th Annual Scientific Meeting and Education Day of the Society for Neuro-Oncology (SNO), Nov. 15-18, 2012.

Wu et al., "Glioma cancer stem cells induce immunosuppressive macrophages/microglia," *Neuro Oncol.*, 12:1113-25, 2010.

Xu et al., "IT-11. The anti-tumor and immunological properties of miR-142-3P in glioma," *Neuro Oncol*, 14(suppl6): vi43-vi49, Abstract, 17th Annual Scientific Meeting and Education Day of the Society for Neuro-Oncology (SNO), Nov. 15-18, 2012.

Zhou et al., "Downregulation of miR-21 inhibits EGFR pathway and suppresses the growth of human glioblastoma cells independent of PTEN status," *Lab Invest.*, 90:144-55, 2010.

Lin et al., "MicroRNA-124 suppresses tumor cell proliferation and invasion by targeting CD164 signaling pathway in non-small cell lung cancer," *J Gene Ther.*, 2(1), 2016.

Wei et al., "MiR-138 exerts anti-glioma efficacy by targeting immune checkpoints," *Neuoro-Oncology*, 18(5):639-648, 2016.

Xu et al., "Effect of miR-142-3p on the M2 macrophage and therapeutic efficacy against murine glioblastoma," *J Natl Cancer Inst.*, 106(8), 2014.

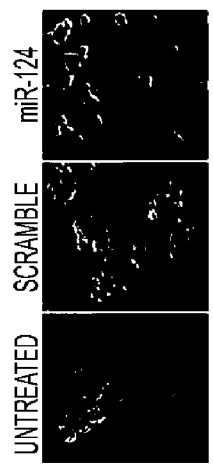
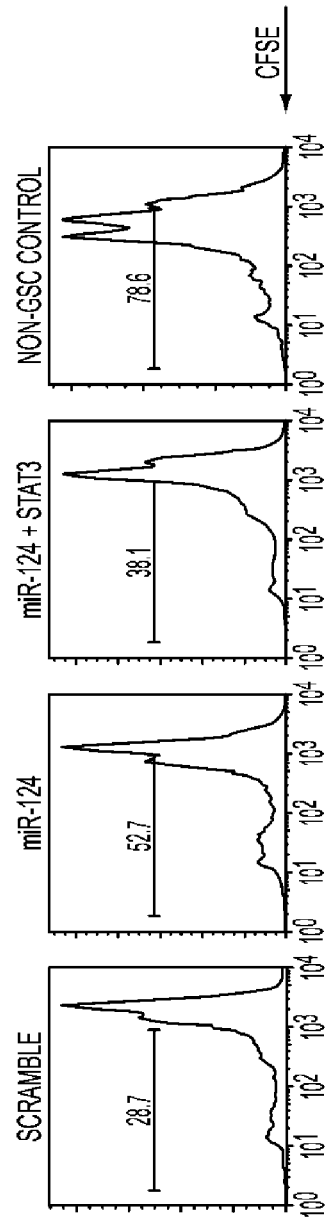
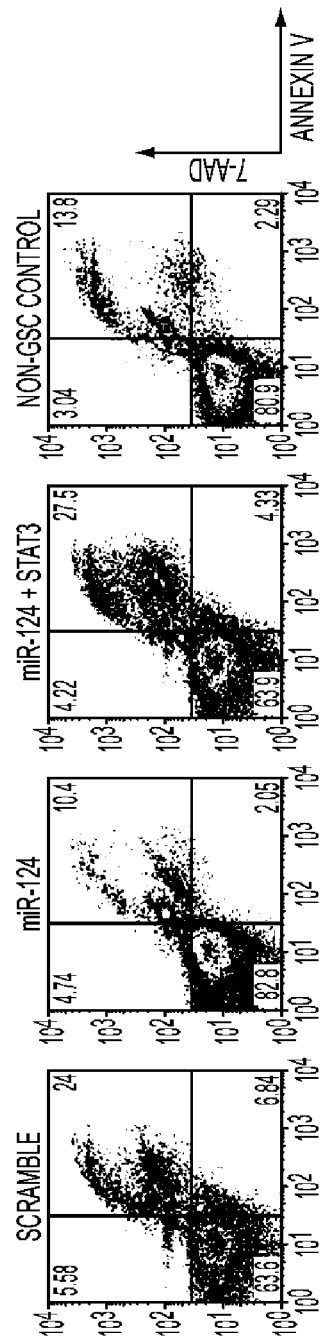
FIG. 2A
FIG. 2B
FIG. 2C

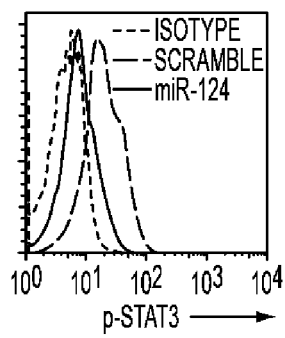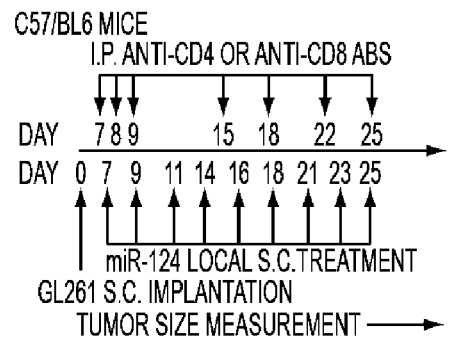
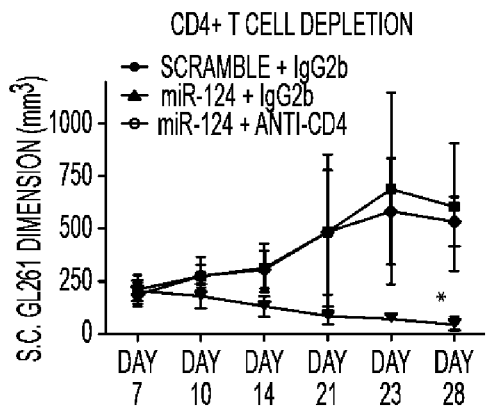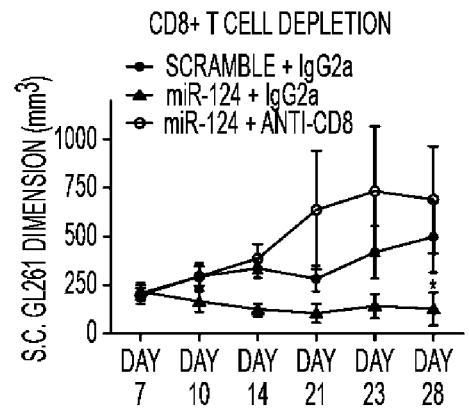
FIG. 6A                FIG. 6B
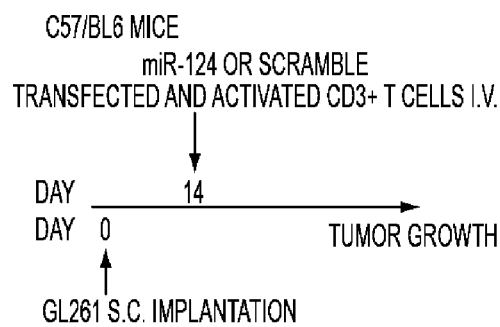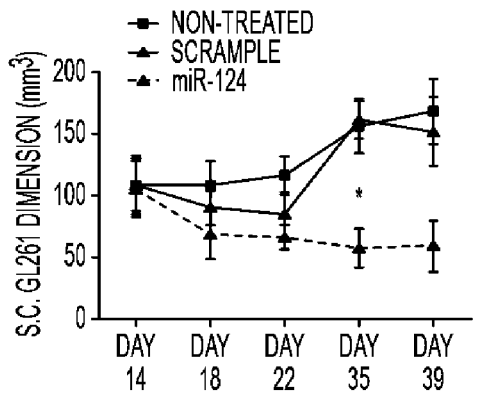
FIG. 6C

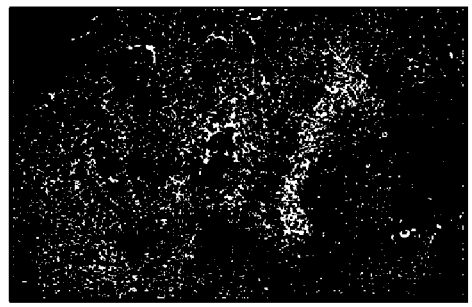
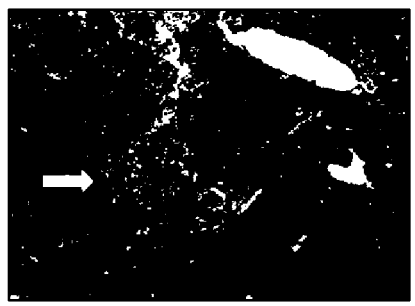
FIG. 7A  FIG. 7B
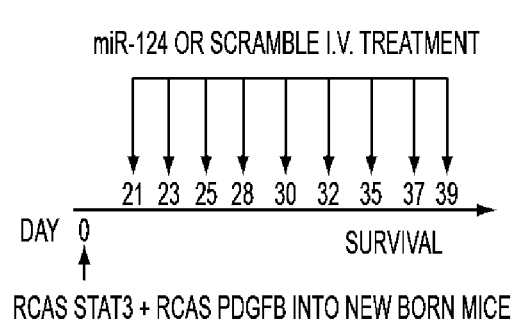
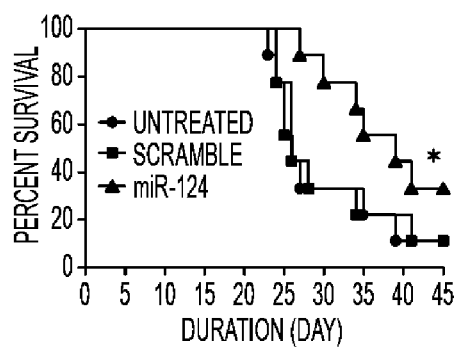
FIG. 7C
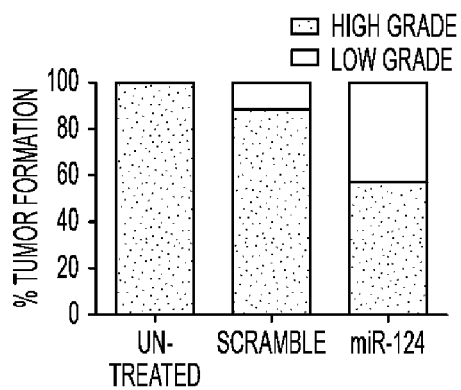
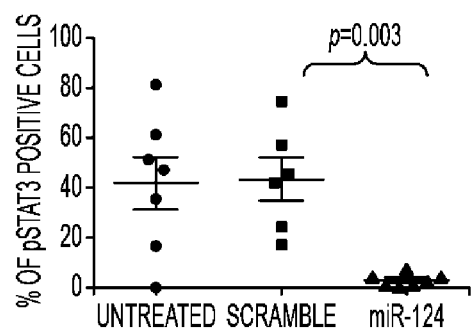
FIG. 7D  FIG. 7E

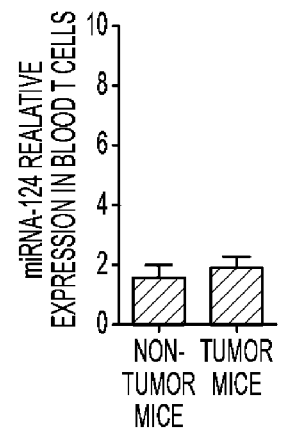
FIG. 12A        FIG. 12B
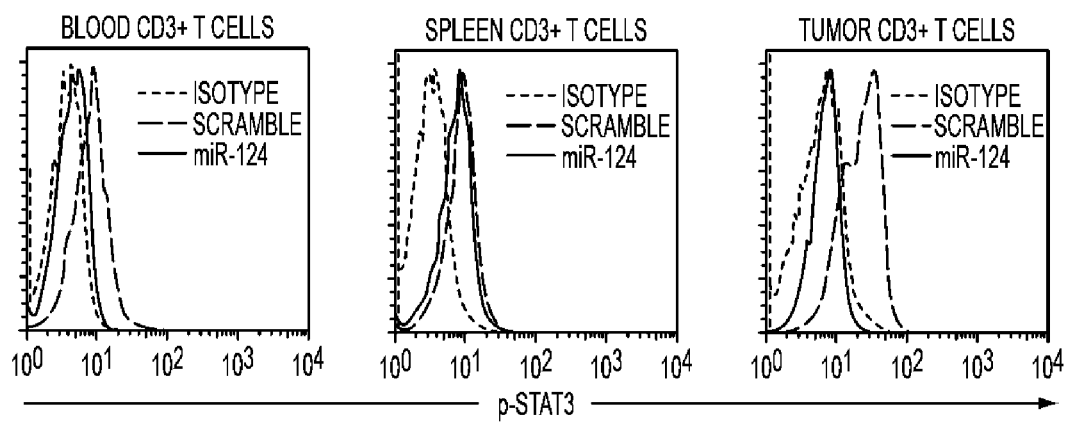
FIG. 12C

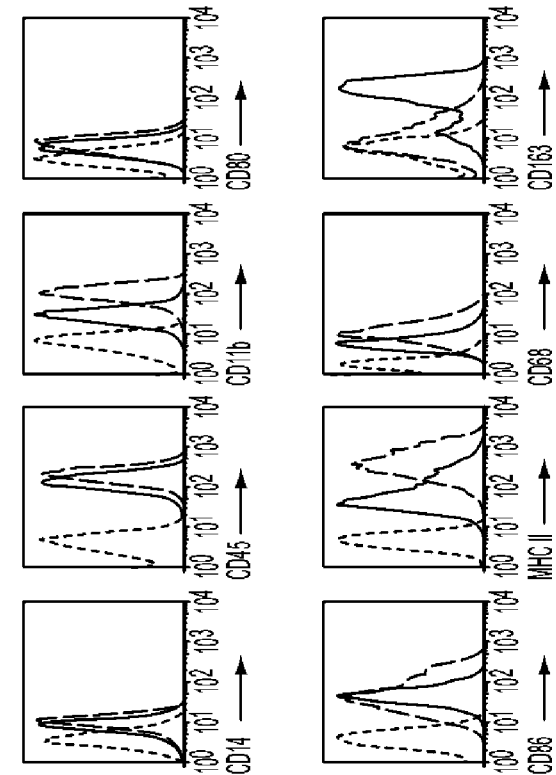
FIG. 15B
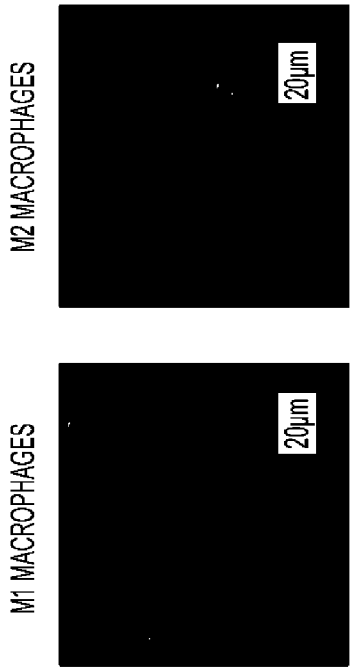
FIG. 15A
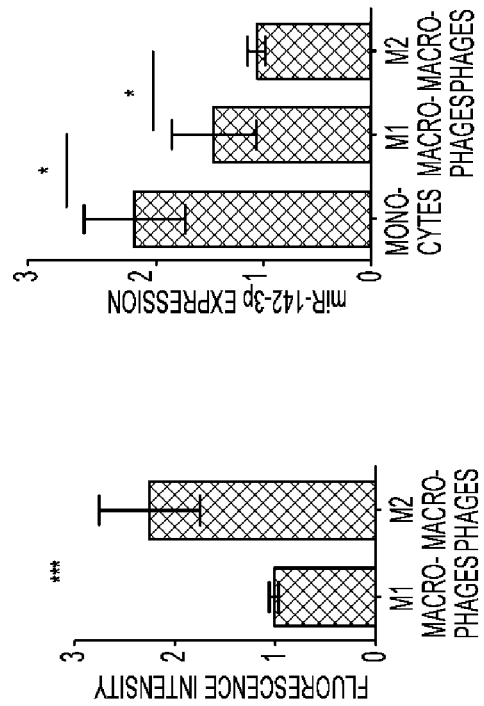
FIG. 15D
FIG. 15C

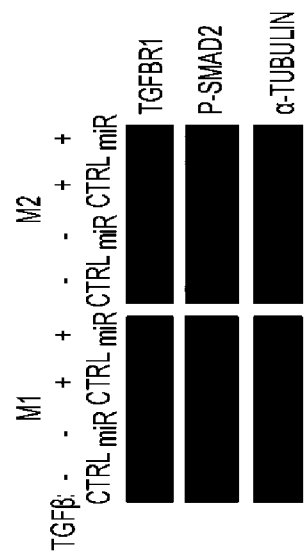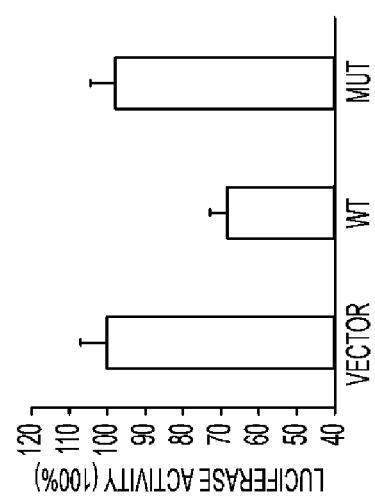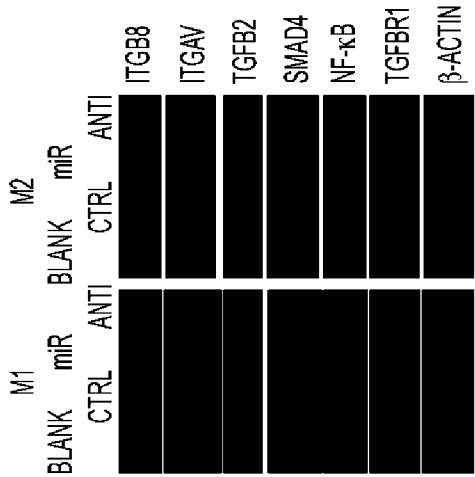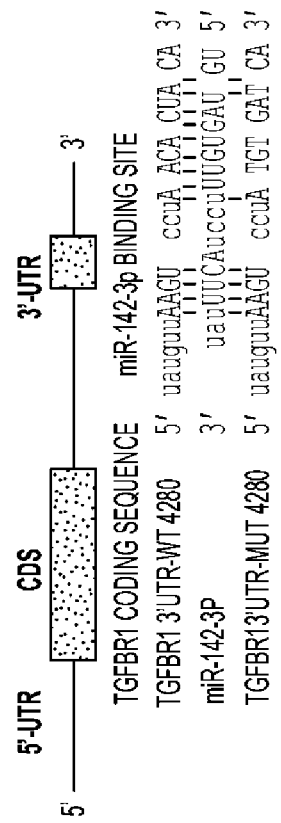
FIG. 16A
FIG. 16B
FIG. 16C
FIG. 16D

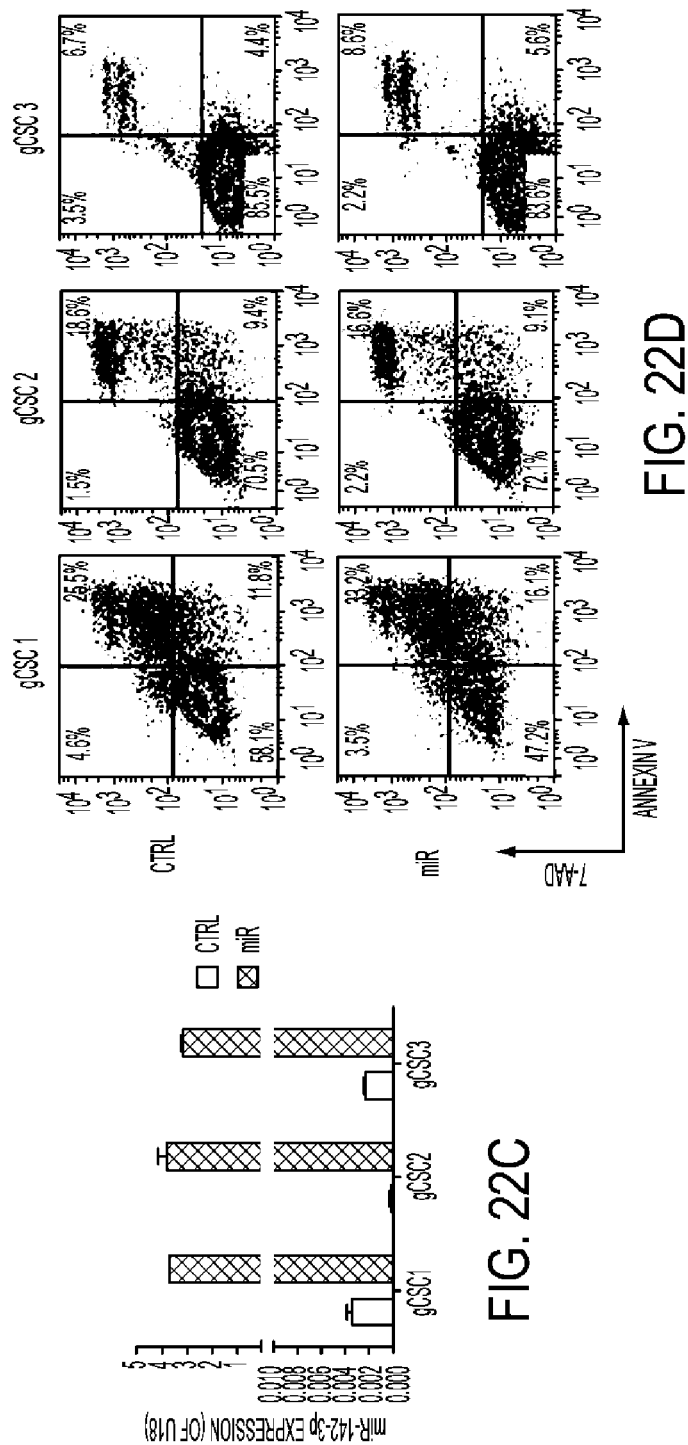

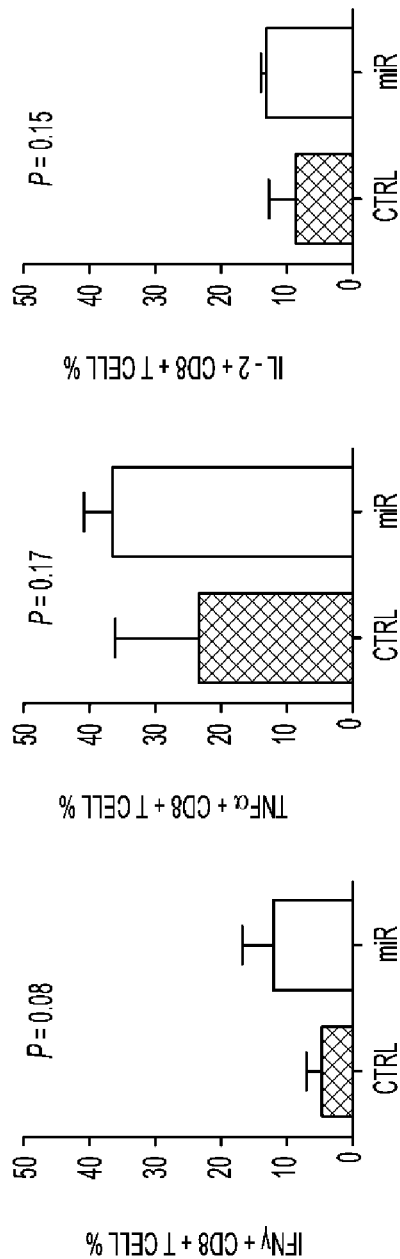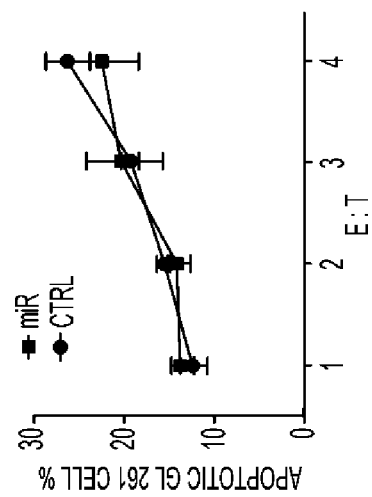
FIG. 24C
FIG. 24D

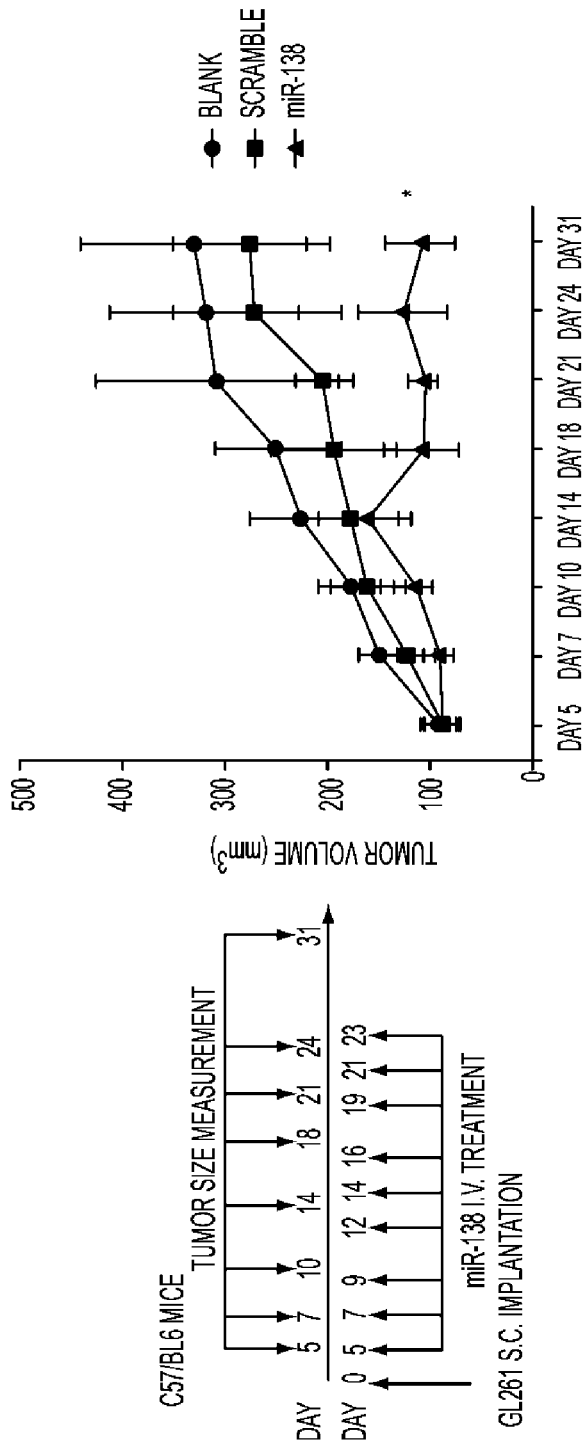
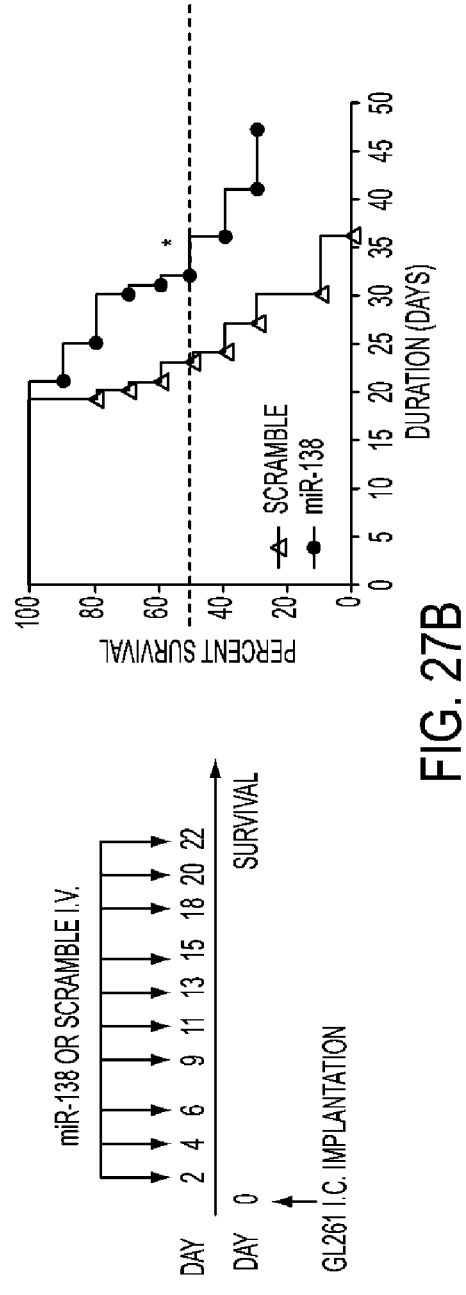
FIG. 27A
FIG. 27B

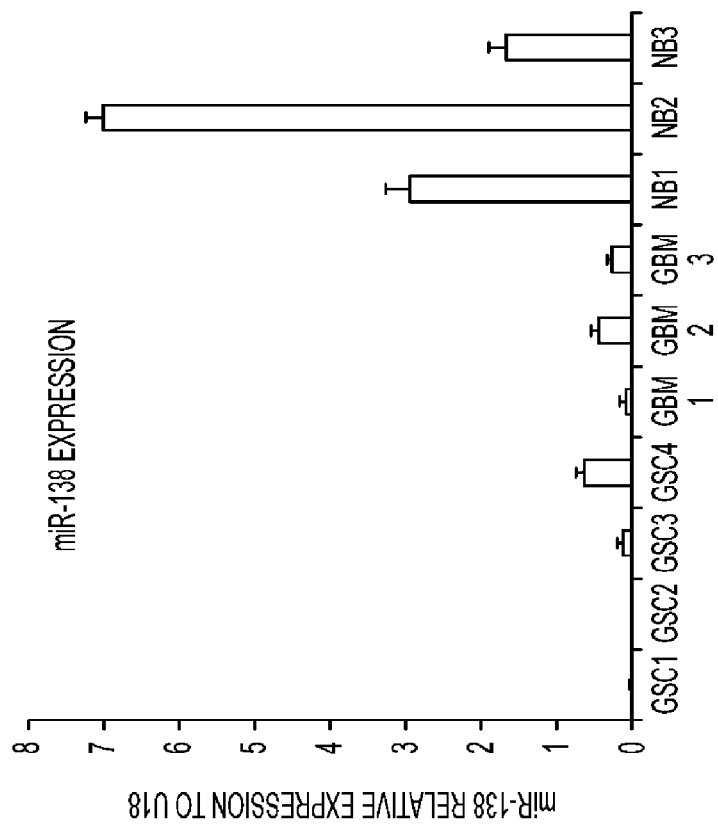
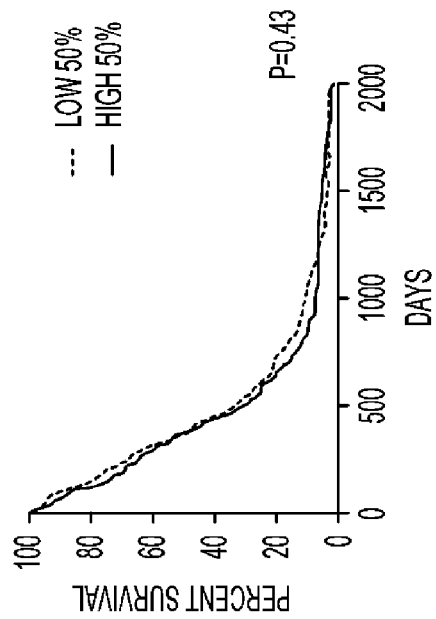
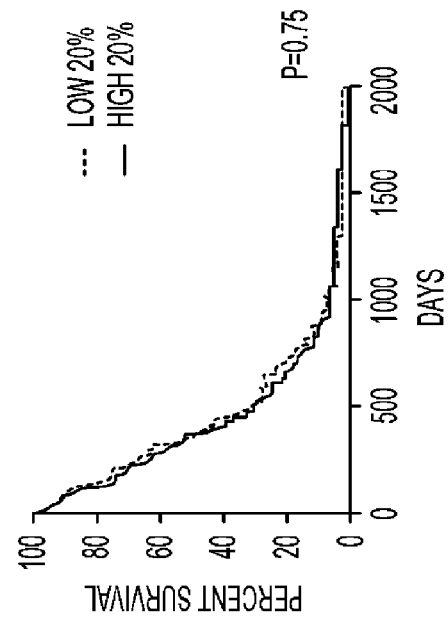

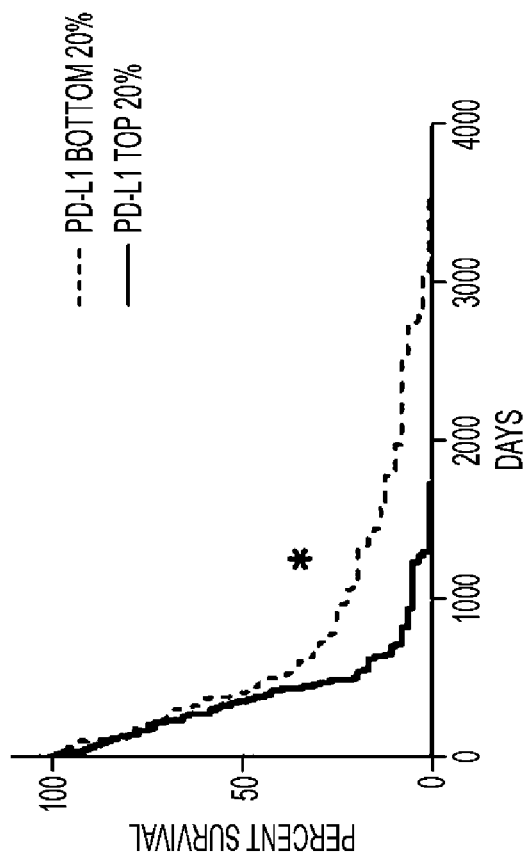
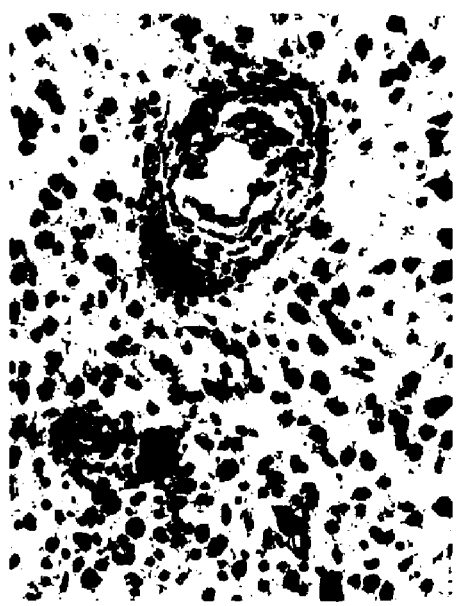
FIG. 30B
FIG. 30A

SEQUENCE LISTING

```
<160> NUMBER OF SEQ ID NOS: 38

<210> SEQ ID NO 1
<211> LENGTH: 85
<212> TYPE: DNA
<213> ORGANISM: Homo sapiens

<400> SEQUENCE: 1
aggcctctct ctccgtgttc acagcggacc ttgatttaaa tgtccataca attaaggcac    60
gcggtgaatg ccaagaatgg ggctg                                         85

<210> SEQ ID NO 2
<211> LENGTH: 87
<212> TYPE: DNA
<213> ORGANISM: Homo sapiens

<400> SEQUENCE: 2
gacagtgcag tcacccataa agtagaaagc actactaaca gcactggagg gtgtagtgtt    60
tcctacttta tggatgagtg tactgtg                                       87

<210> SEQ ID NO 3
<211> LENGTH: 99
<212> TYPE: DNA
<213> ORGANISM: Homo sapiens

<400> SEQUENCE: 3
ccctggcatg gtgtggtggg gcagctggtg ttgtgaatca ggccgttgcc aatcagagaa    60
cggctacttc acaacaccag ggccacacca cactacagg                          99

<210> SEQ ID NO 4
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 4
uaaggcacgc ggugaaugcc a                                             21

<210> SEQ ID NO 5
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 5
gcauucaccg cgugccuuaa u                                             21

<210> SEQ ID NO 6
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 6
```
aguacugcuu acgauacggt t                                              21

<210> SEQ ID NO 7
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 7
ccguaucgua agcaguacut t                                              21

<210> SEQ ID NO 8
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 8
ggcaucaaaa uguaauucut t                                              21

<210> SEQ ID NO 9
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 9
agaauuacau uuugaugcct t                                              21

<210> SEQ ID NO 10
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 10
ccauugauau ugcuccaaat t                                              21

<210> SEQ ID NO 11
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 11
uuuggagcaa uaucaauggt a                                              21

<210> SEQ ID NO 12
<211> LENGTH: 24
<212> TYPE: DNA
<213> ORGANISM: Artificial sequence
<220> FEATURE:
<223> OTHER INFORMATION: Synthetic nucleotide

<400> SEQUENCE: 12
uguaguguuu ccuacuuuau ggau                                           24

<210> SEQ ID NO 13
<211> LENGTH: 24
<212> TYPE: RNA

```
<213> ORGANISM: Artificial sequence
<220> FEATURE:
<223> OTHER INFORMATION: Synthetic nucleotide

<400> SEQUENCE: 13
ccauaaagua ggaaacacua caaa                                              24

<210> SEQ ID NO 14
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 14
aguacugcuu acgauacggt t                                                 21

<210> SEQ ID NO 15
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 15
ccguaucgua agcaguacut t                                                 21

<210> SEQ ID NO 16
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 16
ggcaucaaaa uguaauucut t                                                 21

<210> SEQ ID NO 17
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 17
agaauuacau uuugaugcct t                                                 21

<210> SEQ ID NO 18
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 18
ccauugauau ugcuccaaat t                                                 21

<210> SEQ ID NO 19
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 19
uuuggagcaa uaucaauggt a                                                 21
```

<210> SEQ ID NO 20
<211> LENGTH: 24
<212> TYPE: DNA
<213> ORGANISM: Artificial sequence
<220> FEATURE:
<223> OTHER INFORMATION: Synthetic nucleotide

<400> SEQUENCE: 20
agcugguguu gugaaucagg ccgu                                              24

<210> SEQ ID NO 21
<211> LENGTH: 24
<212> TYPE: RNA
<213> ORGANISM: Artificial sequence
<220> FEATURE:
<223> OTHER INFORMATION: Synthetic nucleotide

<400> SEQUENCE: 21
ggccugauuc acaacaccag cugc                                              24

<210> SEQ ID NO 22
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 22
aguacugcuu acgauacggt t                                                 21

<210> SEQ ID NO 23
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 23
ccguaucgua agcaguacut t                                                 21

<210> SEQ ID NO 24
<211> LENGTH: 16
<212> TYPE: DNA
<213> ORGANISM: Artificial sequence
<220> FEATURE:
<223> OTHER INFORMATION: Synthetic nucleotide

<400> SEQUENCE: 24
uaaggcacgc ggugaa                                                       16

<210> SEQ ID NO 25
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 25
uuguuucugu gggugccuua                                                   20

<210> SEQ ID NO 26
<211> LENGTH: 20
<212> TYPE: DNA
<213> ORGANISM: Artificial sequence
<220> FEATURE:

<223> OTHER INFORMATION: Synthetic nucleotide

<400> SEQUENCE: 26
uuguuucugu gggacggaaa                                        20

<210> SEQ ID NO 27
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 27
uguaguguuu ccuacuuuau                                        20

<210> SEQ ID NO 28
<211> LENGTH: 22
<212> TYPE: DNA
<213> ORGANISM: Artificial sequence
<220> FEATURE:
<223> OTHER INFORMATION: Synthetic nucleotide

<400> SEQUENCE: 28
uauguuaagu ccuaacacua ca                                     22

<210> SEQ ID NO 29
<211> LENGTH: 22
<212> TYPE: DNA
<213> ORGANISM: Artificial sequence
<220> FEATURE:
<223> OTHER INFORMATION: Synthetic nucleotide

<400> SEQUENCE: 29
uauguuaagu ccuatgtgat ca                                     22

<210> SEQ ID NO 30
<211> LENGTH: 23
<212> TYPE: DNA
<213> ORGANISM: Artificial sequence
<220> FEATURE:
<223> OTHER INFORMATION: Synthetic nucleotide

<400> SEQUENCE: 30
agcugguguu gugaaucagg ccg                                    23

<210> SEQ ID NO 31
<211> LENGTH: 23
<212> TYPE: DNA
<213> ORGANISM: Artificial sequence
<220> FEATURE:
<223> OTHER INFORMATION: Synthetic nucleotide

<400> SEQUENCE: 31
gggauguuuc ugucacauca gcu                                    23

<210> SEQ ID NO 32
<211> LENGTH: 23
<212> TYPE: DNA
<213> ORGANISM: Artificial sequence
<220> FEATURE:
<223> OTHER INFORMATION: Synthetic nucleotide

<400> SEQUENCE: 32
gggauguuuc ugucaguugu ccu                                    23

```
<210> SEQ ID NO 33
<211> LENGTH: 23
<212> TYPE: DNA
<213> ORGANISM: Artificial sequence
<220> FEATURE:
<223> OTHER INFORMATION: Synthetic nucleotide

<400> SEQUENCE: 33
acaaggucau uugcuaacua gcu                                              23

<210> SEQ ID NO 34
<211> LENGTH: 23
<212> TYPE: DNA
<213> ORGANISM: Artificial sequence
<220> FEATURE:
<223> OTHER INFORMATION: Synthetic nucleotide

<400> SEQUENCE: 34
acaaggucau uugcuauguu cgu                                              23

<210> SEQ ID NO 35
<211> LENGTH: 23
<212> TYPE: DNA
<213> ORGANISM: Artificial sequence
<220> FEATURE:
<223> OTHER INFORMATION: Synthetic nucleotide

<400> SEQUENCE: 35
gcuuuggggc uuuuacacca guu                                              23

<210> SEQ ID NO 36
<211> LENGTH: 23
<212> TYPE: DNA
<213> ORGANISM: Artificial sequence
<220> FEATURE:
<223> OTHER INFORMATION: Synthetic nucleotide

<400> SEQUENCE: 36
gcuuuggggc uuuuacuggu cuu                                              23

<210> SEQ ID NO 37
<211> LENGTH: 24
<212> TYPE: DNA
<213> ORGANISM: Artificial sequence
<220> FEATURE:
<223> OTHER INFORMATION: Synthetic nucleotide

<400> SEQUENCE: 37
acuccugggg cagggccacc agca                                             24

<210> SEQ ID NO 38
<211> LENGTH: 24
<212> TYPE: DNA
<213> ORGANISM: Artificial sequence
<220> FEATURE:
<223> OTHER INFORMATION: Synthetic nucleotide

<400> SEQUENCE: 38
acuccugggg cagggccugg ucca                                             24
```

MIRNA FOR TREATING CANCER AND FOR USE WITH ADOPTIVE IMMUNOTHERAPIES

This application is a national phase application under 35 U.S.C. 371 of International Application No. PCT/US2014/028296, filed Mar. 14, 2014, which claims the benefit of U.S. Provisional Patent Application No. 61/782,921, filed Mar. 14, 2013, the entirety of each of which is incorporated herein by reference.

The invention was made with government support under grants RO1-CA1208113, P50-CA127001, and P50-CA093459 awarded by the National Institutes of Health. The government has certain rights in the invention.

BACKGROUND OF THE INVENTION

1. Field of the Invention

The present invention relates generally to the field of molecular biology and medicine. More particularly, it concerns miRNA for the treatment of cancer and their use as an immunotherapeutic.

2. Description of Related Art

Glioblastoma, the most common type of primary malignant brain tumor, is associated with disproportionately high morbidity and mortality. Despite multi-modality treatment, the median survival time is 14.6 months for patients with newly-diagnosed glioblastoma (Stupp et al., 2005). Significant and profound immunosuppression exists in the glioblastoma microenvironment and systemically that participates in the glioblastoma pathophysiology by both inhibiting anti-tumor immunity and promoting glioma invasion and progress. Specifically, it has been shown that tumor-associated macrophages, the largest infiltrating immune cell population in glioblastomas (Hussain et al., 2006), do not participate in anti-tumor immune responses but rather support the glioblastoma invasion, progression, and therapeutic resistance (Wu et al., 2010). Micro RNAs (miRNA or miRs) are non-coding molecules involved in post-transcriptional gene regulation that have been shown to modulate tumor cell proliferation and apoptosis and to act as oncogenes or tumor-suppressor genes (Gabriely et al., 2008; Iliopoulos et al., 2010). Although some miRNA have been linked to tumor progression, the connection between tumor-mediated immune modulation and miRNA has not been previously demonstrated. Clearly, there is a need for new treatments for cancers, such as glioblastoma.

SUMMARY OF THE INVENTION

The present invention overcomes limitations in the prior art by exploiting the immune system to mediate the anti-tumor effects of miRNA for the treatment of cancer or inflammation. In some aspects, miR-124 (SEQ ID NO:1), miR-142-3p (SEQ ID NO:2), and/or miR-138 (SEQ ID NO:3) may be administered to a subject, such as a human patient, to treat a cancer, such as a glioblastoma. In some embodiments, the miRNA may promote activation of the immune system and as such may be used as an immunotherapeutic. As shown in the below examples, in vivo local or systemic administration of miR-124, miR-142-3p or miR-138 resulted in inhibition of glioma growth and extended survival in a glioma mouse model. For example, as shown in the below examples, in vivo treatment of established subcutaneous glioma cells with miR-138 demonstrated that gliomas started to shrink as soon as miR-138 was intravenously administered to mice; further, the gliomas continued to regress even after miR-138 treatment was discontinued.

An aspect of the present invention relates to a method of inducing an anti-cancer immune response in a subject, comprising administering to immune cells of said subject, or contacting the immune cells of the subject with, a pharmaceutically effective amount of a nucleic acid composition comprising a miR-124, a miR-142, or a miR-138 nucleic acid sequence in an amount sufficient to induce, enhance, or promote an immune response against the cancer in the subject. The immune cells may comprise T-cells, natural killer (NK) cells, or dendritic cells. The immune cells may be contacted in vivo. In some embodiments, the nucleic acid composition is administered parenterally to the subject. For example, the nucleic acid composition may be administered to the subject intradermally, intravenously, intraarterially, intrathecally, intraperitoneally, intramuscularly, or by injection into a surgical/resection cavity. The nucleic acid composition may be administered to the subject via an aerosol. In some embodiments, the immune cells are contacted with the nucleic acid composition ex vivo in an amount sufficient to immunologically prime the immune cells, and the immunologically primed immune cells are subsequently administered to the patient. In some embodiments, miR-124 is administered to the immune cells. In some embodiments, miR-142 is administered to the immune cells. In some embodiments, miR-138 is administered to the immune cells. The nucleic acid may be a modified nucleic acid such as, e.g., a LNA. In some embodiments, the nucleic acid is an unmodified nucleic acid. The cancer may be selected from the group consisting of a brain cancer, a glioma, a neuroblastoma, a medulloblastoma, a glioblastoma, an astrocytoma, or a melanoma. In some embodiments, the cancer is a brain cancer, a glioma, a neuroblastoma, or glioblastoma. The nucleic acid may comprise a phosphoramidate linkage, a phosphorothioate linkage, a phosphorodithioate linkage, or an O-methylphosphoroamidite linkage. The nucleic acid may comprise one or more nucleotide analogs. The subject is a mammal such as, e.g., a human. In some embodiments, the method further comprises administering to the subject a chemotherapy, immunotherapy, radiotherapy, cytokine therapy, or surgery. In some embodiments, an immunotherapy is administered to the subject. The immunotherapy may be an adoptive immunotherapy. The adoptive immunotherapy may comprise a T-cell immunotherapy, a natural killer (NK) cell immunotherapy, a dendritic cell immunotherapy, a viral immunotherapy, or an adoptive T-cell transfer. The immunotherapy may comprise administration of a monoclonal antibody, interleukin 2 (IL-2), or gamma interferon to the subject. In some embodiments, a monoclonal antibody is administered to the subject, wherein the monoclonal antibody selectively targets an immune checkpoint or immune suppressive pathway or mechanism. The nucleic acid may be comprised in a vector such as, e.g., a viral vector. The viral vector may be an adenovirus, an adeno-associated virus, a lentivirus, or a herpes virus. In some embodiments, the vector comprises a lipid, lipid emulsion, liposome, nanoparticle, or exosomes. The miRNA may be comprised in a liposome, nanoparticle, or exosome. The miRNA may be comprised in a liposome, wherein the liposome comprises N-[1-(2,3-Dioleoyloxy)propyl]-N,N,N-trimethylammonium methyl-sulfate (DOTAP) or Lipofectamine™. Alternately, the liposome or nanoparticle may comprise chitosan, cholesterol, (DOTAP and cholesterol), polyethylene glycol (PEG), dimyristoyl-phosphatidylcholine (DMPC), dimyristoylphosphatidylglycerol (DMPG), soy phosphatidylcholine (HSPC), cholesterol, phosphatidylglycerol (DSPG), dioleoylphosphatidylcholine (DOPC), 1,2-dipalmitoyl-sn-glycero-3-phosphatidylglycerol (DPPG), 1,2-distearoyl-sn-glycero-3-phosphocholine (DSPC), egg lecithin, MPEG-DSPE, Soybean oil, Polysorbate 80, or egg sphingomyelin. The miRNA may be comprised in a nanoparticle, wherein the nanoparticle comprises silicone or gold.

Another aspect of the present invention relates to a pharmaceutical preparation comprising miR-124, miR-142, or miR-138. The miRNA may comprise a phosphoramidate linkage, a phosphorothioate linkage, a phosphorodithioate linkage, or an O-methylphosphoroamidite linkage. In some embodiments, the miRNA is a LNA. The pharmaceutical preparation may be formulated for intravenous, intraperitoneal, intratumoral, intrathecal, intranasal, intralymphatic, or oral administration. The miRNA may be comprised in a liposome, nanoparticle, or exosome. The pharmaceutical preparation may comprise N-[1-(2,3-Dioleoyloxy)propyl]-N,N,N-trimethylammonium methyl-sulfate (DOTAP) or Lipofectamine™.

Yet another aspect of the present invention relates to a method of treating a cancer in an individual, comprising: (a) contacting T-cells, natural killer (NK) cells, or dendritic cells to be used in an adoptive therapy with a synthetic or recombinant miR-124, miR-142, or miR-138 in an amount sufficient to promote or enhance the function or proliferation of the cells; and (b) administering the T-cells, natural killer (NK) cells, or dendritic cells to the individual. The cells may be incubated in the presence of the miRNA in vitro, wherein the miRNA are synthetic or recombinant miRNA. The miRNA may be comprised in a liposome during at least a portion of said incubation. The liposome may comprise N-[1-(2,3-Dioleoyloxy)propyl]-N,N,N-trimethylammonium methyl-sulfate (DOTAP) or Lipofectamine™. The miRNA may be encoded by a nucleic acid, wherein the nucleic acid has been transfected into the cells. Said transfection may comprise electroporation or incubation with a viral vector. The viral vector may be an adenovirus, an adeno-associated virus, a lentivirus, or a herpes virus.

In some embodiments, miRNAs may be combined (e.g., miR-124, miR-142-3p, and/or miR-138) for further therapeutic synergy and/or comprehensive targeting of tumor-mediated immune suppression. In some embodiments, the combined miRNAs may be administered to a subject, such as a human patient, in combination with one or more additional immune therapy. For example, in some aspects a pharmaceutical preparation may comprise (miR-124 and miR-142-3p), (miR-124 and miR-138), (miR-142-3p and miR-138), or (miR-124, miR-142-3p, and miR-138) and an excipient. The pharmaceutical preparation may be formulated in a liposome or other pharmaceutical preparation as described herein. The pharmaceutical preparation may be used to treat a cancer (e.g., a glioma, etc.) as described herein. The combination therapy of a miRNA may be further combined with an additional therapy such as, e.g., a radiation therapy, surgery, additional chemotherapy (e.g., a STAT3 inhibitor such as WP1066, etc.), or additional immune therapy to treat a cancer (e.g., a glioma, etc.) as described herein.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) Relative expression levels of miR-124 were detected by TaqMan quantitative PCR. There was a significant difference in the relative expression levels of miR-124 between normal brain tissues, glioblastoma specimens, and glioma cancer stem cells (gCSCs). (FIG. 1B) Representative specimens of normal brain (I) demonstrating miR-124 expression (arrow) by in situ hybridization in neurons and in a glioblastoma (II) lacking miR-124 expression (at 40× magnification). (FIG. 1C) Sequence of the predicted miR-124 binding site (SEQ ID NO:24) on the STAT3-3'UTR (SEQ ID NO:25) and the STAT3-3'UTR mutant (SEQ ID NO:26) that disrupted miR-124 binding. On the basis of predictive algorithms, there exists an 11-bp nucleotide binding site in the STAT3 3'-UTR that is imperfectly paired with miR-124, which is predicted to lead to STAT3 mRNA degradation. (FIG. 1D) Relative luciferase activity of HeLa cells after transfection with miR-124- or scramble control-expressing plasmids in conjunction with a wild type STAT3 3'-UTR or miR-124 binding site mutant reporter construct, demonstrating inhibition of STAT3. **P<0.01. (FIG. 1E) Western blot analysis of the STAT3 signaling pathway gCSCs transfected with scramble control (S) compared with miR-124 (M).

FIGS. 2A-E. miR-124 reverses glioma-mediated immunosuppression. (FIG. 2A) The gCSC phenotype was markedly altered by miR-124, as photographed 48 hours after transfection. (FIG. 2B) T-cell proliferation was detected by flow cytometry analysis with CFSE staining after 3 days of treatment with medium alone, gCSC-scramble-transfected conditioned medium, gCSC-miR-124-transfected conditioned medium, or gCSC-miR-124+STAT3-transfected conditioned medium. miR-124 up regulation caused a reversal of inhibition in T-cell proliferation compared with the gCSC-scramble-transfected conditioned medium. STAT3 overexpression restored gCSC inhibition on T-cell proliferation. (FIG. 2C) T-cell apoptosis was measured by the percentage of annexin V+ 7-AAD+ cells. Similarly, miR-124 up regulation decreased gCSC-induced T-cell apoptosis, whereas STAT3 overexpression reversed the miR-124 effect. (FIG. 2D) T-cells were analyzed on the basis of CD4 and FoxP3 expression levels, by flow cytometry analysis. Up regulation of miR-124 caused a decline in Treg induction compared with the scrambled gCSC control, and STAT3 addition restored the ability of the gCSCs to induce Tregs. (FIG. 2E) The functional suppressive activity of FoxP3+ Tregs induced in (FIG. 2D) was verified by autologous coculture with CD4+ T-cells. The experiments were repeated three times with similar results, and one representative set of data is shown.

(FIG. 4A) The treatment schema and the volumes of subcutaneous GL261 tumors in C57BL/6J mice treated intratumorally with either miR-124 or scramble control, or left untreated starting on day 6 (n=10/group/experiment). In the miR-124 group, * denotes a P value of <0.01 compared with both the untreated and scramble control tumors. Standard deviations are shown. Arrows indicate days of treatment and tumor size measurements. The inset photo on the right is of a representative ex vivo GL261 tumor comparison between miR-124- and scramble control-treated tumor-bearing mice. (FIG. 4B) Ex vivo immunohistochemical analysis of gliomas, untreated (n=2), or treated with a scramble control (n=5), or miR-124 (n=3), which demonstrates a marked decrease in p-STAT3 expression in the local tumor microenvironment (P=0.0039). (FIG. 4C) Splenocytes from miR-124 intratumorally treated GL261 mice (n=3) have markedly increased cytotoxicity at 48 hours after coculture with GL261 cells compared with that in splenocytes from scramble control oligonucleotide-treated tumor-bearing mice (P<0.001). The ratios of splenocytes to GL261 cells are 10:1, 40:1, and 100:1. Error bars in the curve represent the standard deviation in the data from 3 mice. (FIG. 4D) Decreased tumor-infiltrating FoxP3+ Tregs in miR-124-treated GL261 mice. A single example is shown, but identical results were obtained in two other tumor bearing animals. Furthermore, miR-124 administration enhances IFN-γ and TNF-α production in CD4 T-cells (FIG. 4E) and CD8 T-cells (FIG. 4F) in the tumor local microenvironment. One set of representative FACS plots is shown. Similar results were obtained from another two tumor-bearing mice treated with miR-124 or scramble control, respectively.

(FIG. 5A) The treatment schema and the volumes of subcutaneous GL261 tumors in C57BL/6J mice treated intravenously with miR-124 or scramble control starting on day 7 (n=10/group/experiment). In the miR-124 group, * denotes a P value of <0.01 compared with scramble control tumors. Standard deviations are shown. The arrows indicate days of treatment and tumor size measurements. (FIG. 5B) The treatment schema and volumes of subcutaneous GL261 tumors in nude mice treated intratumorally with miR-124 or scramble control starting on day 7 (n=10/group/experiment). Standard deviations are shown. Arrows indicate days of treatment and tumor size measurements. (FIG. 5C) Treatment schema and graph of the Kaplan-Meier estimate, demonstrating better survival in C57BL/6J mice with miR-124-treated intracerebral GL261 gliomas (n=10/group/experiment) than in scrambled controls. * denotes a P value=0.02 compared with scramble control gliomas. (FIG. 5D) Graph of the Kaplan-Meier estimate demonstrates miR-124's lack of therapeutic effect in nude mice with intracerebral GL261 gliomas (n=10/group/experiment, P=0.24).

FIGS. 6A-C. T-cells mediate the antiglioma immune therapeutic efficacy of miR-124. (FIG. 6A) Histogram shows miR-124 transfection inhibited p-STAT3 activity in adoptively transferred T cells. (FIG. 6B) The treatment schema and volumes of subcutaneous GL261 tumors in C57BL/6J mice treated intratumorally with miR-124 or scramble control subcutaneously on day 7 (n=8/group/experiment) in the setting of in vivo CD4+ T-cells or CD8+ T-cell depletion. Arrows indicate days of treatment and tumor size measurements. *denotes a P value of <0.01 comparing the anti-CD4 or anti-CD8 depletion group with the isotype and miR-124-treated group. Standard deviations are shown. (FIG. 6C) The treatment schema and volumes of subcutaneous GL261 tumors in C57BL/6J mice treated intravenously with miR-124 or scramble control transfected CD3+ T-cells on day 14 (n=10/group/experiment). *denotes a P value of <0.01 comparing the miR-124 transfected T-cell treated group with the scramble control and untreated group.

FIGS. 7A-E. miR-124 exerts a therapeutic effect in Ntv-a mice. (FIG. 7A) Representative hematoxylin and eosin staining of a high-grade glioma induced in Ntv-a mice transfected with RCAS-PDGFB and RCAS-STAT3 transgenes demonstrates neovascular proliferation (arrow) and pseudopallisading necrosis (arrowhead) at 100× magnification. (FIG. 7B) Representative specimen from the brain of an Ntv-a mouse transfected with the RCAS-PDGFB and RCAS-STAT3 transgenes demonstrates miR-124 expression by in situ hybridization in neurons surrounding a glioma devoid of miR-124 expression (arrow) at 400× magnification. (FIG. 7C) Treatment schema and graph of the Kaplan-Meier estimate demonstrates improved survival in miR-124-treated Ntv-a mice transfected with the RCAS-PDGFB and RCAS-STAT3 transgenes (n=9/group) compared with scramble control and untreated mice (lipofectamine 2000 vehicle only). *denotes a P value of 0.04. (FIG. 7D) Summary graph demonstrates the incidence of high- and low-grade gliomas on the basis of hematoxylin and eosin staining features of necrosis and neovascular proliferation in miR-124-treated Ntv-a mice transfected with RCAS-PDGFB and RCAS-STAT3 transgenes (n=7) compared with scrambled controls (n=8) and untreated mice (n=7) (P<0.0001). (FIG. 7E) An ex vivo immunohistochemical analysis of gliomas, untreated (n=7) or treated with a scramble control (n=6) or miR-124 (n=7), demonstrates a marked decrease in p-STAT3 expression in the local tumor microenvironment of the miR-124-treated group (scramble vs. miR-124: P=0.003; untreated vs miR-124: P=0.007; untreated vs scramble: P=0.87). Quantification of p-STAT3 expression was obtained by averaging the number of nuclear positive p-STAT3 cells by immunohistochemistry from 10 non-overlapping high-power microscopic fields (magnification× 400) of the gliomas obtained from either untreated RCAS-PDGF-B+RCAS-STAT3 mice or mice treated with the scramble control or miR-124. Each dot represents the analysis of one mouse glioma.

(FIG. 8A) Summary dot plot demonstrating miR-124 expression is induced in gCSCs (n=8) upon neural differentiation (P<0.01). Black filled circles: gCSCs; black filled squares: differentiated gCSCs. (FIG. 8B) Interleukin-8 (IL-8) (P<0.05), galectin-3 (P<0.01), and MIC-1 (P<0.05) produced by gCSCs were reduced upon transfection with miR-124 compared with their levels in the scramble control.

(FIG. 10A) Relative expression levels of miR-21 were detected by TaqMan quantitative PCR. There were significant differences in the relative expression levels of miR-21 between normal brain tissues, gCSCs and glioblastoma specimens. (FIG. 10B) T-cell proliferation was detected by flow cytometry analysis with CFSE staining after 3 days of treatment with medium alone, gCSC-scramble-transfected conditioned medium, or gCSC-miR-21-transfected conditioned medium. miR-21 up regulation caused further inhibition in T-cell proliferation compared with the gCSC-scramble-transfected conditioned medium. (FIG. 10C) Forced overexpression of miR-124 in the gCSCs resulted in the down modulation of miR-21 expression.

FIGS. 12A-C. Up regulation of miR-124 level and down regulation of p-STAT3 in peripheral blood T-cells and glioma-infiltrating T-cells after intravenous administration of miR-124. (FIG. 12A). The miR-124 expression level is below the limit of detection in CD3+ T-cells isolated from the blood of non-tumor bearing C57/BL6J mice (n=3) and GL261-bearing mice (n=3) (P>0.05). Levels are shown relative to U6 snRNA. (FIG. 12B) miR-124 is detected in both CD3+ T-cells isolated from blood (P<0.05 relative to scramble control; n=3) and gliomas (P<0.05 relative to scramble control; n=3) 18 hours after the in vivo administration of miR-124. (FIG. 12C) Coinciding with the presence of miR-124, p-STAT3 expression levels were decreased in the T-cells from the peripheral blood and gliomas in the miR-124 treated mice. Representative histograms were shown. The p-STAT3 expression levels relative to isotype control in the peripheral blood T-cells in the miR-124 treated mice (1.4±0.2%) was down-modulated compared to scramble treated mice (17.9±1.9%) (P=0.007; n=3) and glioma-infiltrating T-cells (miR-124: 4.3±0.1%; scramble: 18.2±4.3%; P=0.007), but not within the splenic T-cells (miR-124: 16.8±0.9%; scramble: 12.9±2.7%; P=0.07).

(FIG. 14A). Heatmaps demonstrating the miRNA expression pattern in glioblastoma-infiltrating macrophages compared with matched peripheral blood monocytes, utilizing the Human miRNA OneArray Microarray v2. With a mean 4.9-fold decrease in level relative to matched peripheral blood monocytes, miR-142-3p emerged as a leading down-regulated candidate. (FIG. 14B) Total RNA was extracted from gCSCs (n=5), glioma cell lines (U-87 and U-251), glioblastomas (n=4), healthy donor peripheral blood CD14+ monocytes (n=3), glioblastoma patient peripheral blood CD14+ monocytes (n=6), and glioblastoma infiltrating CD11b+ macrophages (n=3). Analysis by quantitative reverse transcription polymerase chain reaction demonstrated that although miR-142-3p is not expressed in glioma cell lines or gCSCs, monocytes express high levels of miR-142-3p and are a major contributing source of miR-142-3p in glioblastomas.

FIGS. 15A-D. Preferential Expression of miR-142-3p in M1 Macrophages. Human CD14+ monocytes were incubated with GM-CSF or M-CSF to induce M1 and M2 macrophages, respectively. FIG. 15A, The M1 and M2 macrophages have a distinctive in vitro morphology. Scale bar=20 µM. FIG. 15B, Cell surface expression of CD14, CD45, CD11b, CD80, CD86, MHC II, CD68 and CD163 were evaluated by flow cytometry. Representative results are shown. Similar result was observed in 3 replicates. The grey histogram denotes M1 macrophages, black denotes M2 macrophages, and the dotted line represents the isotype control. FIG. 15C, The phagocytic activity of M1 and M2 was measured by fluorescent uptake and summarized. Error bars represent standard deviations. A paired two-sided Student t test was used. n=6, ***P<0.001. FIG. 15D, The miR-142-3p expression as determined by quantitative reverse transcription polymerase chain reaction analysis was down regulated during macrophage differentiation but preferentially in the immunosuppressive M2 macrophages relative to the proinflammatory M1 macrophages. Error bars represent standard deviations. A paired two-sided Student t test was used. n=6, *P=0.03.

FIGS. 16A-D. miR-142-3p Interacts with the TGFβR1 Pathway. FIG. 16A, Western blot analysis of the predicted miR-142-3p targets as indicated by bioinformatics tools in M1 and M2 macrophages untreated (blank), transfected with scramble control (ctrl), transfected with miR-142-3p (miR), or transfected with anti-miR-142-3p (anti). Similar result was observed in 3 replicates. FIG. 16B, miR-142-3p overexpression inhibits the downstream target, p-SMAD2, in M2 macrophages. After 5 days, the M1 and M2 macrophages were treated with TGF-β1, transfected with scramble control (ctrl) or miR-142-3p (miR) and then measured for p-SMAD2. Similar result was observed in 3 replicates. FIG. 16C, Sequence of the predicted miR-142-3p binding site (SEQ ID NO:27) on the TGFBR1-3'UTR (upper; SEQ ID NO:28) and the mutated TGFBR1-3'UTR sequence which potentially disrupts miR-142-3p binding (lower; SEQ ID NO:29). FIG. 16D, The relative luciferase activity in HeLa cells after transfection with miR-142-3p—in conjunction with the parental luciferase vector, the wild type TGFBR1 3'-UTR or the miR-142-3p binding site mutant reporter construct. Luciferase activity is shown relative to the parental luciferase vector and error bars represent standard deviations.

(FIG. 17A) Representative flow analysis cytometry and summarized data demonstrating more early apoptosis (Annexin $V^+7$-AAD$^-$) and late apoptosis/cell death (Annexin $V^+7$-AAD$^+$) induced in M2- than in M1-committed monocytes at 48 hours after the miR-142-3p transfection (n=9). *P=0.02. (FIG. 17B) Representative flow analysis cytometry and summarized data set of blockade of TGFβR1 by the antagonist SB431542 and LY364947 demonstrating induced preferential M2 macrophage apoptosis (n=6). *P=0.04 and** P=0.001.

FIG. 19C, Immunohistochemistry demonstrating staining with anti-F4/80 antibodies to identify glioma-infiltrating macrophages. Left panel: representative images (max: ×400) of mice treated with scramble control and miR-142-3p respectively. Right panel: quantification of glioma-infiltrating macrophage and comparison between the two groups. Scale bar=50 µm. FIG. 19D, The correlation between the percentage of glioma-infiltrating F4/80+ macrophages and the survival duration of miR-142-3p treated mice. R2=0.303.

(FIG. 20A) miR-142-3p expression was significantly upregulated after transfection with a miR-142-3p precursor into the M1 and M2 macrophages. (FIG. 20B) Transfection of miR-142-3p did not change the expression levels of TGFβR1 mRNA as detected by RT-PCR. (FIG. 20C) Summarized TGF-β2 ELISA data from M1 and M2 macrophages demonstrating miR-142-3p transfection does not alter secretion.

(FIG. 21A) After the miR-142-3p precursor/inhibitor transfection, the expression of the general macrophage marker CD68 did not significantly change in either the M1 or M2 macrophages (light grey is isotype control; black is CD68). (FIG. 21B) Expression of CD163, a specific marker for M2 macrophages, was down regulated upon the overexpression of miR-142-3p (light grey is isotype control; black is CD68). CD163 expression in M2 was upregulated by the miR-142-3p inhibitor (anti-miR). (FIG. 21C) Summarized data of the effects of miR-142-3p in macrophages. *P=0.02, n=8.

FIGS. 22A-D: (FIG. 22A) TGFβR1 was down regulated in both M1 and M2 macrophages for two different TGFβR1 siRNAs (set #1 and set #2). (FIG. 22B) Preferential apoptosis was observed in M2 macrophages compared to M1 macrophages in both siRNA treated group. (FIG. 22C) miR-142-3p expression was significantly upregulated after transfection with a miR-142-3p precursor into the gCSCs. (FIG. 22D) Neither early apoptosis (Annexin $V^+7$-AAD$^-$) nor late apoptosis/cell death (Annexin $V^+7$-AAD$^+$) was induced in gCSCs transfected with miR-142-3p.

FIG. 23A, The treatment schema of tumor-free C57BL/6J mice (n=5 per group) with scramble control or miR-142-3p duplex is shown. FIG. 23B, No significant change in the cell count was found for peripheral monocytes or T-cells in miR-142-3p treated mice relative to the scramble control (P>0.05).

FIGS. 24A-D. FIG. 24A, Spleen macrophages from miR-142-3p treated tumor animals presented a more M1-like differentiated phenotype. Bars indicate the mean proportion (±SEM) of the percent of CD11b+ macrophages producing the cytokines Specifically, the percentage of CD11b+IL-6+ M2 macrophages was reduced to 51.1% in the miR-142-3p group relative to 71.8% in the control group (P=0.013). Furthermore, the CD11b+TNFα+M1 macrophage percentage was increased from 13.9% in the control group to 22.7% in the miR-142-3p group (P=0.032). FIG. 24B, Representative flow cytometric analysis of MHCII/33D1 surface expression on mature dendritic cells (mDCs) in splenocytes of GL261 tumor-bearing mice treated with miR-142-3p or scramble control. Percentages represent the proportion of the MHCII+33D1+ cell subset. FIG. 24C, No significant changes of effector cytokine production in CD8+ T-cells were found between miR-142-3p and scramble treated groups. D) CD8+ T-cells from miR-142-3p-treated mice display similar cytotoxicity to that displayed by CD8+ T-cells from control mice E:T (effector T-cells: tumor cells) ratio 1, 2, 3 and 4 represent 1:1, 5:1, 10:1 and 20:1, respectively. Data are combined from 3 mice. P-value of statistical analysis (unpaired t-test) was shown above each bar graph.

FIG. 25A. The three predicted miR-138 binding sites in the 3' un-translated region of CTLA-4 are noted with their sequences. The mutational alterations are noted for each luciferase expression construct. FIG. 25B. The miR-138 PD-1 binding site sequence. FIG. 25C. A significant decrease in luciferase expression is seen when the cells are co-transfected with a reporter plasmid containing the wild-type 3' UTR of PD-1 and miR-138 (WT-mir138 vs WT-scr, 18% decrease in relative luciferase expression, p<0.05); whereas this difference is abolished when the mutant 3' UTR reporter plasmid is evaluated (Mut-scr vs Mut-mir138).

FIGS. 27A-B: miR-138 exerts potent efficacy to suppress GL261 tumors in a syngeneic mouse model. FIG. 27A. The treatment schema and the volumes of subcutaneous GL261 tumors in C57BL/6J mice treated intravenously with either miR-124 or scramble control, or left untreated starting on day 5 (n=10 group/experiment). The figure is the result of a single experiment but was repeated with identical results. In the miR-138 group, *denotes a P value of <0.01 compared with both the untreated and scramble control tumors. Standard deviations are shown. Arrows indicate days of treatment and tumor size measurements. FIG. 27B. Treatment schema and graph of the Kaplan-Meier estimate demonstrating survival of C57BL/6J mice with intracranial GL261 that were treated intravenously with miR-138 versus scramble control. miR-138 treatment resulted in a marked increase in median survival in comparison to scramble control (33.5 versus 23.5 days; p=0.01).

FIG. 28A. Treatment schema and graph of the Kaplan-Meier estimate demonstrating the lack of therapeutic effect of miR-138 in nude mice with intracerebral GL261 gliomas (n=8 in scramble miRNA group, 7 in miR-138 treatment group, P=0.87). FIG. 28B. Photomicrograph (400×) showing FoxP3 expressing lymphocytes within GL261 tumors treated with scramble control versus miR-138. The dot plot graph summarizes the number of FoxP3+ cells per 1000 between scramble and miR-138 treated intracerebral GL261 tumors.

FIGS. 29A-C: Kaplan-Meier curves demonstrate that there is no significant difference in survival between high expression and low expression of miR-138 utilizing data from 383 glioblastoma patients in The Cancer Genome Atlas comparing (FIG. 29A) the upper 50% versus lower 50% level of expression or (FIG. 29B) the top 20% versus bottom 20% level of expression. FIG. 29C. The expression of miR-138 mRNA is diminished in gCSCs and glioblastomas relative to normal brain by quantitative PCR.

FIGS. 30A-C: FIG. 30A. Kaplan-Meier survival estimates stratified by the presence or absence of PD-L1 expression based on TCGA data sets. There was a significant decrease in survival with increased PD-L1 expression (p=0.0018, log-rank test). FIG. 30B. Representative microphotograph of immunohistochemical staining for PD-L1 on the glioblastoma TMA. FIG. 30C. Histograms demonstrating the amount of PD-L1 expression relative to isotype controls in gCSCs and in glioma cell lines.

DESCRIPTION OF ILLUSTRATIVE EMBODIMENTS

I. Definitions

Figure 1A:
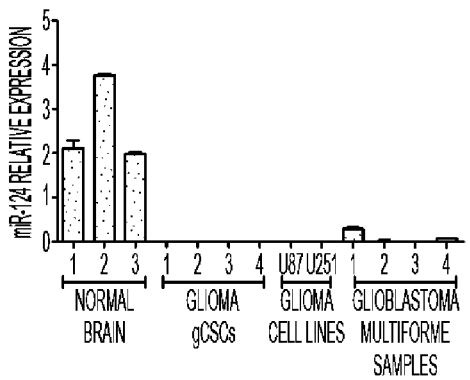
FIGS. 1A-E. miR-124 expression is significantly reduced in glioblastoma and inhibits the signal transducer and activator of transcription 3 (STAT3).

A nucleic acid will generally contain phosphodiester bonds, although nucleic acid analogs may be included that have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. The 2'-OH-group may be replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. Modified nucleotides also include nucleotides conjugated with cholesterol through, e.g., a hydroxyprolinol linkage as described in Krutzfeldt et al. (2005); Soutschek et al. (2004); and U.S. Patent Publication No. 20050107325, which are incorporated herein by reference. Modified nucleotides and nucleic acids may also include locked nucleic acids (LNA), as described in U.S. Patent Publication No. 2002/0115080, U.S. Pat. No. 6,268,490, and U.S. Pat. No. 6,770,748, which are incorporated herein by reference. LNA nucleotides include a modified extra methylene "bridge" connecting the 2' oxygen and 4' carbon of the ribose ring. The bridge "locks" the ribose in the 3'-endo (North) conformation, which is often found in the A-form of DNA or RNA. LNA nucleotides can be mixed with DNA or RNA bases in the oligonucleotide whenever desired. Such oligomers are commercially available from companies including Exiqon (Vedbaek, Denmark). Additional modified nucleotides and nucleic acids are described in U.S. Patent Publication No. 20050182005, which is incorporated herein by reference. Modifications of the ribose-phosphate backbone may be done for a variety of reasons, e.g., to increase the stability and half-life of such molecules in physiological environments, to enhance diffusion across cell membranes, or as probes on a biochip. Mixtures of naturally occurring nucleic acids and analogs may be made; alternatively, mixtures of different nucleic acid analogs, and mixtures of naturally occurring nucleic acids and analogs may be made.

In some embodiments, a LNA or other nucleic acid analog may be produced via methods involving use of an enzyme. Methods for producing LNA include the use of an enzyme or polymerase have been shown, e.g., in Pinheiro et al. (2012). In some embodiments, a polymerase may be used in the synthesis of C5-ethynyl locked nucleic acids, LNA, cyclohexenyl nucleic acids (CeNA), anhydrohexital nucleic acids (HNA), or threofuranosyl nucleid acids (TNA) (see, e.g., Veedu et al., 2010; Pinheiro et al., 2012). Producing LNA via the use of an enzyme may significantly reduce the costs associated with the production of LNA.

In certain embodiments, a LNA may be administered to a subject, such as a mammal, mouse, rat, dog, primate, or human subject. It is anticipated that a miRNA of the present invention (e.g., miR-124, miR-142, or miR-138) does not need to be LNA. In various embodiments, a similar effect may be achieved using one or more unmodified miRNA ring, which may result in improved hybridization with complementary RNA. By use of a similar strategy, constraining the ethyl chain in the MOE residue back to the 4'-position of the furanose ring system can be used to make nucleosides E (R-constrained MOE or R-cMOE) and F (S-cMOE) below (Seth et al., 2008). The methoxymethyl groups in cMOE nucleosides may mimic the steric and hydration attributes of MOE nucleosides and may, in some embodiments, improve the safety profile of antisense oligonucleoties containing these modifications. (Teplova et al., 1999).

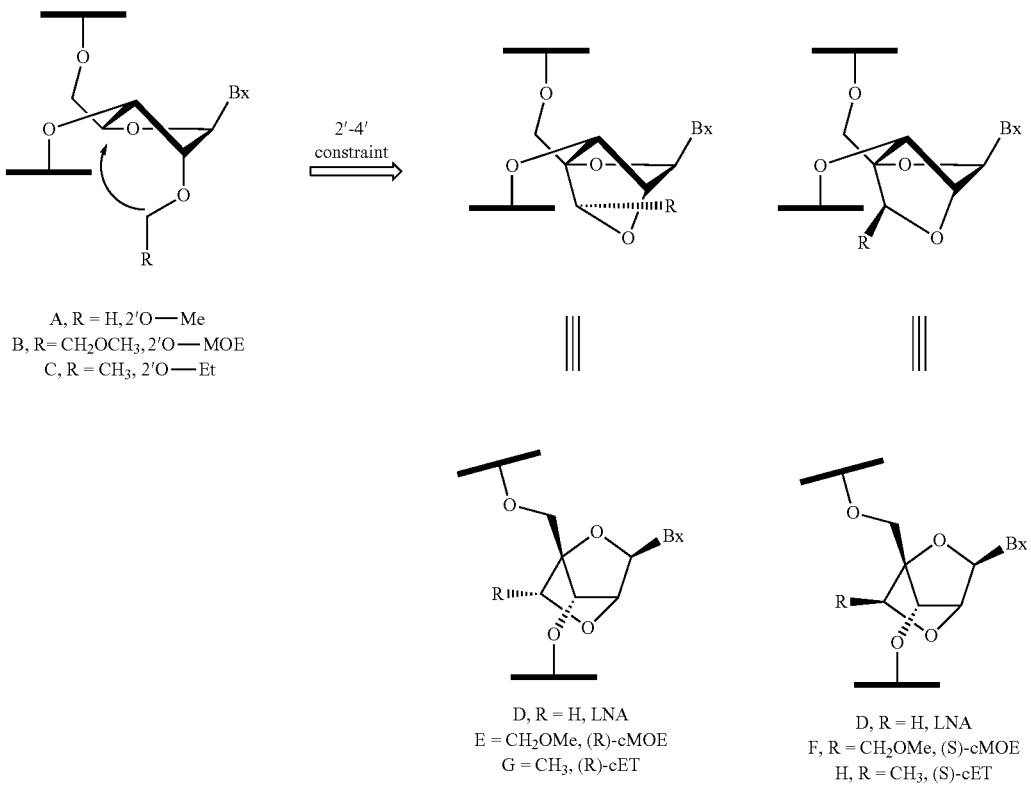

sequences either alone, as a "naked miRNA," or comprising one or more modification (e.g., to reduce in vivo degradation, improve pharmacokinetics, etc.).

In some embodiments, a modified nucleic acid that is not a LNA may be administered to an individual to treat a cancer or hyperproliferative disease. For example, an antisense nucleic acid comprising a 2'-4' conformationally restricted nucleoside analogue may be used. Previous work involving short oligonucleotides with a 2'-4' conformationally restricted nucleoside analogues has shown that these molecules may exhibit increased potency without increased toxicity in animals (Seth et al., 2009). Alternately, a cyclohexenyl nucleic acid (CeNA), an anhydrohexital nucleic acid (HNA), or a threofuranosyl nucleid acid (TNA) may be used as, or the modification may be included in, a miRNA of the present invention such as, e.g., miR-124, miR-142, or miR-138.

LNA (or 2'-4' BNA) generally refers to a 2'-OMe nucleoside (A, below) where the methyl group is constrained back to the 4'-position of the furanose ring system. The 2'-4' constraint enforces an N-type sugar pucker of the furanose "Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

II. Micrornas (MIRNAS)

MicroRNAs (miRNAs) are short, non-coding RNAs that can target and substantially silence protein coding genes through 3'-UTR elements. Important roles for miRNAs in numerous biological processes have been established, but comprehensive analyses of miRNA function in complex diseases are lacking. MiRNAs are initially transcribed as primary miRNAs (pri-miRNAs) that are then cleaved by the nuclear RNAses Drosha and Pasha to yield precursor-miRNAs (pre-miRNAs). These precursors are further processed by the cytoplasmic RNAse III dicer to form short double stranded miR-miR* duplexes, one strand of which (miR) is then integrated into the RNA Induced Silencing Complex (RISC) that includes the enzymes dicer and Argonaute (Ago). The mature miRNAs (~17-24nt) direct RISC to specific target sites located within the 3'UTR of target genes. Once bound to target sites, miRNAs represses translation through mRNA decay, translational inhibition and/or sequestration into processing bodies (P-bodies) (Eulalio et al., 2008; Behm-Ansmant et al., 2006; Chu and Rana, 2006). Recent estimates find that over 60% of protein coding genes carry 3'-UTR miRNA target sites (Friedman et al., 2009). In this regard, miRNAs act as key regulators of processes as diverse as early development (Reinhart et al., 2000), cell proliferation and cell death (Brennecke et al., 2003), apoptosis and fat metabolism (Xu et al., 2003), and cell differentiation (Chen, 2004; Dostie et al., 2003). In addition, studies of miRNA expression in chronic lymphocytic leukemia (Calin et al., 2008), colonic adenocarcinoma (Michael et al., 2003), Burkitt's lymphoma (Metzler et al., 2004), cardiac disease (Zhao et al., 2007) and viral infection (Pfeffer et al., 2004) suggest vital links between miRNA and numerous diseases.

miRNAs thus far observed have been approximately 21-22 nucleotides in length and they arise from longer precursors, which are transcribed from non-protein-encoding genes. See review of Carrington et al. (2003). The precursors form structures that fold back on each other in self-complementary regions; they are then processed by the nuclease Dicer in animals or DCL1 in plants. miRNA molecules interrupt translation through precise or imprecise base-pairing with their targets. In some embodiments, a miRNA may be used therapeutically or administered to a subject, such as a human patient, to treat a disease such as, e.g., cancer; alternately, in some embodiments, a nucleic acid that is complementary to the miRNA may be therapeutically administered to a subject in vivo or used in vitro to generate the desired therapeutic miRNA (e.g., miRNA-142-3p, miRNA-142-3p, miRNA-124, or miRNA-138). In this way, the complementary nucleic acid may be used as a template to generate the desired therapeutic miRNA (e.g., miRNA-142-3p, miRNA-142-3p, miRNA-124, or miRNA-138).

III. Adoptive Immunotherapies

In some embodiments, a miRNA of the present invention, such as miR-124, miR-142, or miR-138 may be used as an immunotherapeutic. Without wishing to be bound by any theory, the below examples indicate that these miRNA can activate the immune systems response to a cancer. These miRNAs were selected based on their ability to block tumor-mediated immune suppression or immune checkpoints. A previous therapeutic limitation of using miRNAs for solid malignancies has been insufficient tumor targeting and penetration. This limitation may be overcome by activating or exploiting the immune system to gain access to the tumor. In some embodiments, circulating immune cells may be among the first cells that contact an administrated miRNA. Without wishing to be bound by any theory, in some embodiments, immune system responses may mediate the anti-tumor effect, thus in some embodiments the mode of administration does not require miRNA to make direct contact with the tumor, e.g., intratumoral injection is not required in some embodiments. Although a miRNA as disclosed herein may be directly administered (e.g., intravenously, etc.) into a human subject, the miRNAs may also be utilized to modify a wide variety of pre-existing immunotherapeutic approaches including but not exclusive to: adoptive T-cell transfers, NK immunotherapy, dendritic cell immunotherapy, and/or a viral immunotherapy to enhance their therapeutic effect. The miRNAs could be used to directly modify an adoptive immunotherapy or given concurrently with the adoptive immunotherapy. For example, isolated CD3+ T-cells may be transfected with miR-124, and their numbers expanded in vitro before adoptively transferring these cells into patients. In mice models, this type of miR-124 transfection in the CD3+ T cells was observed to inhibit p-STAT3 in the adoptively transferred T cells, and a significant enhancement of the anti-tumor therapeutic effects in comparison to unmodified CD3+ T cells was observed. As shown in the below examples, miR-124 transfected adoptively transferred T cells can induce potent anti-tumor immune effector responses while minimizing Tregs in the tumor microenvironment. In various embodiments, another miRNA of the present invention, such as, e.g., miR-142 or miR-138, may be substituted for or used in combination with miR-124, as described above.

IV. Clinical Information

A. Definitions

"Treatment" and "treating" as used herein refer to administration or application of a therapeutic agent to a subject or performance of a procedure or modality on a subject for the purpose of obtaining a therapeutic benefit of a disease or health-related condition.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease.

"Prevention" and "preventing" are used according to their ordinary and plain meaning to mean "acting before" or such an act. In the context of a particular disease or health-related condition, those terms refer to administration or application of an agent, drug, or remedy to a subject or performance of a procedure or modality on a subject for the purpose of blocking the onset of a disease or health-related condition.

The term "compound" refers to any chemical entity, pharmaceutical, drug, and the like that can be used to treat or prevent a disease, illness, sickness, or disorder of bodily function. Compounds comprise both known and potential therapeutic compounds. A compound can be determined to be therapeutic by screening using the screening methods of the present invention. A "known therapeutic compound" refers to a therapeutic compound that has been shown (e.g., through animal trials or prior experience with administration to humans) to be effective in such treatment. In other words, a known therapeutic compound is not limited to a compound efficacious in the treatment of asthma.

A "sample" is any biological material obtained from an individual. For example, a "sample" may be a blood sample or a lung tissue sample.

B. Dosage

A pharmaceutically effective amount of a therapeutic agent as set forth herein is determined based on the intended goal, for example inhibition of cell death. The quantity to be administered, both according to number of treatments and dose, depends on the subject to be treated, the state of the subject, the protection desired, and the route of administration. Precise amounts of the therapeutic agent also depend on the judgment of the practitioner and are peculiar to each individual.

For example, a dose of the therapeutic agent may be about 0.0001 milligrams to about 1.0 milligrams, or about 0.001 milligrams to about 0.1 milligrams, or about 0.1 milligrams to about 1.0 milligrams, or even about 10 milligrams per dose or so. Multiple doses can also be administered. In some embodiments, a dose is at least about 0.0001 milligrams. In further embodiments, a dose is at least about 0.001 milligrams. In still further embodiments, a dose is at least 0.01 milligrams. In still further embodiments, a dose is at least about 0.1 milligrams. In more particular embodiments, a dose may be at least 1.0 milligrams. In even more particular embodiments, a dose may be at least 10 milligrams. In further embodiments, a dose is at least 100 milligrams or higher.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. Dosages of nucleic acid or LNA which may be used include, for example, about from 10-100 mg (LNA or nucleic acid)/g body weight, about 25-75 mg (LNA or nucleic acid)/g body weight, about mg (LNA or nucleic acid)/g body weight, or any range derivable therein. A dosage of about 50 mg (LNA or nucleic acid)/g mouse body weight was observed to be effective to substantially inhibit allergic or inflammatory lung responses in mice in vivo. In some embodiments, a dose of about 0.01-5 mg/kg, about 0.01-1 mg/kg, or about 0.03-1 mg/kg may be administered to a subject, such as a human patient.

The dose can be repeated as needed as determined by those of ordinary skill in the art. Thus, in some embodiments of the methods set forth herein, a single dose is contemplated. In other embodiments, two or more doses are contemplated. Where more than one dose is administered to a subject, the time interval between doses can be any time interval as determined by those of ordinary skill in the art. For example, the time interval between doses may be about 1 hour to about 2 hours, about 2 hours to about 6 hours, about 6 hours to about 10 hours, about 10 hours to about 24 hours, about 1 day to about 2 days, about 1 week to about 2 weeks, or longer, or any time interval derivable within any of these recited ranges.

In certain embodiments, it may be desirable to provide a continuous supply of a pharmaceutical composition to the patient. This could be accomplished by catheterization, followed by continuous administration of the therapeutic agent. The administration could be intra-operative or post-operative.

V. Pharmaceutical Compositions and Routes for Administration to Patients

Some embodiments of the present invention involve administration of pharmaceutical compositions. Where clinical applications are contemplated, pharmaceutical compositions will be prepared in a form appropriate for the intended application. Generally, this will involve preparing compositions that are essentially free of pyrogens, as well as other impurities that could be harmful to humans or animals.

In some embodiments, a miRNA may be delivered in a lipid emulsion, a liposome, a nanoparticle, an exosome, or in a viral vector. The liposome may be a unilamellar, multilamellar, or multivesicular liposome. It is anticipated that a wide variety of liposomes and exosomes may be used with the present invention. For example, in some embodiments, a silicone nanoparticle may be used to deliver a miRNA to a cell (e.g., as described in Bharali et al. *PNAS* (2005) 102(32): 11539-11544, which is incorporated by reference in its entirety). Liposomes may comprise N-[1-(2,3-Dioleoyloxy)propyl]-N,N,N-trimethylammonium methyl-sulfate (DOTAP) or Lipofectamine™. In some embodiments, a delivery system involving chitosan may be used as described, e.g., in Lu et al. (*Cancer Cell* (2010) 18:185-197), which is incorporated by reference in its entirety without disclaimer. In some embodiments, a nanovector may be used to deliver a miRNA to a subject; nanovectors are described, e.g., in Pramanik et al. *Mol Cancer Ther* (2011) 10:1470-1480, which is incorporated by reference in its entirety without disclaimer.

One will generally desire to employ appropriate salts and buffers in preparing compositions of therapeutic agents. Buffers also will be employed when recombinant cells are introduced into a patient. Aqueous compositions of the present invention comprise an effective amount of the therapeutic agent, dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the therapeutic agents of the compositions.

The active compositions of the present invention may include classic pharmaceutical preparations. Administration of these compositions according to the present invention may be via any common route so long as the target tissue is available via that route. Administration may be by any method known to those of ordinary skill in the art, such as intravenous, intradermal, subcutaneous, intramuscular, intraperitoneal, intrathecal, intralymphatic, inhalation, intranasal, or by direct injection into the tumor. Other modes of administration include oral, buccal, and nasogastric administration. The active compounds may also be administered parenterally or intraperitoneally. Such compositions would normally be administered as pharmaceutically acceptable compositions, as described supra. In particular embodiments, the composition is administered to a subject using a drug delivery device. For example, the drug delivery device may be a catheter or syringe. Alternatively, the miRNAs could be incorporated into a polymer or polifeprosan and implanted into a resection cavity or delivered by convection enhanced delivery.

By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils and by spray-dry techniques. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying, freeze-drying and spray-drying techniques which yield a powder of the active ingredient(s) plus any additional desired ingredient from a previously sterile-filtered solution thereof.

In preferred embodiments systemic formulations of the miRNA are contemplated. Systemic formulations include those designed for administration by injection, e.g. subcutaneous, intravenous, intramuscular, intrathecal or intraperitoneal injection, as well as those designed for transdermal, transmucosal, inhalation, oral or pulmonary administration. In some embodiments, a miRNA of the present invention is delivered by intravenous or intratumoral injection. In embodiments, the mode of administration is not intratumoral injection.

For injection, the proteins of the embodiments may be formulated in aqueous solutions, preferably in physiologically compatible buffers such as Hanks' solution, Ringer's solution, or physiological saline buffer. The solution may contain formulatory agents such as suspending, stabilizing and/or dispersing agents.

For oral administration the therapeutic agents of the present invention generally may be incorporated with excipients. Any excipient known to those of ordinary skill in the art is contemplated. In some embodiments, administration is not oral. In some embodiments, it may be advantageous to modify any miRNA that will be administered orally to reduce degradation. In some embodiments it may be preferable to administer a miRNA via a route that is not oral, such as, e.g., an intravenous, parenteral, intraperitoneal, intratumoral, or subcutaneous, etc. route. In some embodiments, a miRNA of the present invention is administered intravenously.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like). Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like).

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15$^{th}$ Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

VI. Cancers

In some aspects, a miRNA of the present invention may be administered to a subject or individual to treat a cancer.

In some embodiments, the cancer is a brain cancer, a glioma, a neuroblastoma, glioblastoma, glioblastoma multiforme, an oligodendroglioma or metastatic tumor to the brain. In various aspects, it is anticipated that miRNAs of the present invention may be used to treat virtually any malignancy. In some embodiments, the cancer may suppress the immune system of the subject or individual with the cancer. In some embodiments and as shown in the below examples, miRNA as provided herein can suppress or reverse cancer-mediated immune suppression and allow for immune recognition and clearance of the malignancy.

In some embodiments, a miRNA of the present invention may be used to promote or enhance clearance or attack of a cancer by the immune system of a subject or individual with the cancer. Cancer cells that may be treated with miRNA according to the embodiments include but are not limited to cells from the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor may comprise an osteosarcoma, angiosarcoma, rhabdosarcoma, leiomyosarcoma, Ewing sarcoma, glioblastoma, neuroblastoma, or leukemia.

VII. Combined Therapy

In another embodiment, it is envisioned to use a miRNA or a miRNA inhibitor as set forth herein in combination with other therapeutic modalities. Thus, in addition to the therapies described above, one may also provide to the patient a more "standard" pharmaceutical therapy. Examples of other therapies include, e.g., a chemotherapy, a radiotherapy or radiation therapy, a cytokine therapy, a gene therapy, an immunotherapy, and/or a surgery. In some embodiments, a miRNA of the present invention such as, e.g., miR-124, miR-142, or miR-138 is administered to a subject in combination with an adoptive immunotherapy.

The other therapeutic modality may be administered before, concurrently with, or following administration of the miRNA. The therapy using miRNA may precede or follow administration of the other agent(s) by intervals ranging from minutes to weeks. In embodiments where the other agent and the miRNA are administered separately, one would generally ensure that a significant period of time did not expire between the time of each delivery, such that each agent would still be able to exert an advantageously combined effect. In such instances, it is contemplated that one would typically administer the miRNA and the other therapeutic agent within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of a miRNA, or the other agent will be desired. In this regard, various combinations may be employed. By way of illustration, where the miRNA is "A" and the other agent is "B", the following permutations based on 3 and 4 total administrations are exemplary:

| | | | | | |
|---|---|---|---|---|---|
| A/B/A | B/A/B | B/B/A | A/A/B | B/A/A | A/B/B |
| B/B/B/A | B/B/A/B | A/A/B/B | A/B/A/B | A/B/B/A | B/B/A/A |
| B/A/B/A | B/A/A/B | B/B/B/A | A/A/A/B | B/A/A/A | A/B/A/A |
| A/A/B/A | A/B/B/B | B/A/B/B | B/B/A/B | | |

Other combinations are likewise contemplated. Non-limiting examples of pharmacological agents that may be used in the present invention include any pharmacological agent known to be of benefit in the treatment of a cancer or hyperproliferative disorder or disease.

VIII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1 miR-124 Systemically Enhances T Cell Mediated Anti-Glioma Immune Clearance by Inhibiting STAT3 Signaling A. Materials and Methods 1. miR Comparison of Glioblastoma to Normal Brain Tissue This study was approved by the institutional review board at M.D. Anderson and conducted according to protocol #LAB03-0687. Tumors were pathologically confirmed as glioblastoma (World Health Organization grade IV) by a board-certified neuropathologist. Tumors were washed in RPMI1640 medium and dissected to remove blood products and surrounding non-tumor brain tissue. The total tissue was broken down into smaller pieces and digested in digesting buffer from the cancer cell isolation kit (Panomics, Santa Clara, Calif.) for 2 hours. The cells were suspended in RNAlater solution (Ambion, Austin, Tex.) in Rnase-free tubes and stored at 4° C. overnight; after 24 hours, they were transferred to −80° C. until needed for total RNA extraction. Extraction was performed using the mirVana kit (Ambion). Once extracted, RNA levels were analyzed for concentrations and purity using UV/Vis spectroscopy at 230, 260, and 280 nm.

Total RNA extracted from patients was sent to Phalanx Biotech Group (Belmont, Calif.) for microRNA and mRNA-gene expression analyses. Total RNA from normal brain tissues was obtained from Biochain (Hayward, Calif.). The results of the glioblastoma human miRNA OneArray Microarray v2 analysis were used to determine which miRs had significant differences in expression compared with normal donor miRs. Expressional differences in terms of multiples (−fold differences) were calculated with Microsoft Excel, and miRs with the most significant differences in expression levels were chosen for the miR target analysis using TargetScan (Release 5.1)(Friedman et al., 2009). miRs of interest were selected on the basis of putative targets and the degree of deviation from normal brain.

2. Real-Time PCR to Confirm Relative miRNA Expression Levels

Total RNA extracted from glioblastoma cells or gCSCs was used as the template for reverse transcription using the TaqMan reverse transcription kit (Applied Biosystems, Carlsbad, Calif.) in a thermocycler, per the manufacturer's instructions. Primers for reverse transcription and PCR were purchased for human miR-124, miR-21, U6 and U18 snRNAs (Applied Biosystems). U6 and U18 was used as an endogenous control. cDNA was used as the template for real-time PCR. U18 and miR-124 amplifications were run in triplicate using the TaqMan real-time PCR kit (Applied Biosystems) in the 7500 real-time PCR system (Applied Biosystems). Further reactions, substituting water for the cDNA template, were used as additional controls. Excel was used to calculate the mean levels of each miR and the U18 internal control. The relative expression levels of miR-124 were compared with those of the internal controls, and a bar graph was generated.

3. Glioma Tissue Microarray and In Situ Hybridization

This study was conducted according to LAB09-0463, which was approved by the institutional review board at MD Anderson and includes 235 patients with different glioma grades. The TMAs consisted of resected glioma tissues from glioblastoma (n=150), gliosarcoma (n=6), anaplastic astrocytoma (n=24), anaplastic mixed oligoastrocytoma (n=9), anaplastic oligodendroglioma (n=16), mixed oligoastrocytoma (n=5), oligodendroglioma (n=24), low-grade astrocytoma (n=1), subependymoma (n=2), and normal brain (cortex; n=19), and they have been previously described (Barnett et al., 2007). For TMA construction, two 1-mm cores were obtained per tumor sample. The time from resection to fixation was less than 20 minutes in all cases, in accordance with the Clinical Laboratory Improvement Amendments standard.

In situ hybridization was performed using the protocol developed by Nuovo et al (2009) with some minor adjustments. Digoxigenin-labeled, locked nucleic acid-modified probes for miR-124 (hsa-miR-124) and the positive control (U6, hsa/mmu/rno) were purchased from Exiqon (Vedbek, Denmark). In brief, 4-μm sections of the TMA blocks were placed in a heater at 59° C. overnight to attach cores to the silane-coated slide. Sections were deparaffinized with xylene (2×5 minutes), rehydrated with ethanol (100%, 50%, & 25% for 5 minutes each), and treated with diethylpyrocarbonate-treated water for 1 minute. Protease treatment was performed with pepsin solution (1.3 mg/ml) (Dako, Glostrup, Denmark) at 37° C. for 50 minutes. After a post-fixation step in 4% paraformaldehyde, hybridization of the locked nucleic acid probe was carried out in a Hybrite (Abbott Laboratories, Abbott Park, Ill.) at 60° C. for 5 minutes followed by 37° C. overnight (12-18 hours). A low-stringency post-hybridization wash was performed at 4° C. in standard sodium citrate containing 2% bovine serum albumin for 5 minutes, followed by incubation with anti-digoxigenin/alkaline phosphate conjugate antibodies (Enzo Diagnostics, Farmingdale, N.Y.) in a heater at 37° C. for 30 minutes. The blue color was developed by incubating the slide with nitroblue tetrazolium and bromchloroindolyl phosphate (Enzo Diagnostics) at 37° C. The colorimetric reaction was monitored visually and stopped by placing the slides in water when background coloring started to appear. The TMA was analyzed by the study neuropathologist. In the assessment of miR-124 expression in gliomas, intervening neurons in the infiltrating component were not considered positive.

4. miR-124 Transfection in gCSCs, Astrocytes and T-Cells

The precursor form of miR-124 (30 nM) and the scramble negative control were used to transfect gCSCs and T-cells using the siPORT NeoFX transfection agent (Applied Biosystems) or Nucleofector transfection kit (Lonza, Allendale, N.J.). Cells were incubated for 72 hours at 37° C. to determine cell surface marker expression and collect secreted cytokines. miR-124 expression was verified via RT-PCR after transfection. The morphologic characteristics of the gCSCs were documented at 48 hours after the transfection. A rescue experiment of miR-124 inhibition was accomplished by cotransfection with a plasmid expressing wild-type, constitutively active STAT3 without a miR-124 binding 3' UTR site (provided by Dr. Jinbo Yang).

5. In Vivo Experiments

The miR-124 duplex that mimics pre-miR-124a (sense: 5'-UAAGGCACGCGGUGAAUGCCA-3' (SEQ ID NO:4), antisense: 3'-UAAUUCCGUGCGCCACUUACG-5', (SEQ ID NO:5)) and the scramble control miRNA duplex (sense: 5'-AGUACUGCUUACGAUACGGTT-3' (SEQ ID NO:6), antisense: 3'-TTUCAUGACGAAUGCUAUGCC-5'(SEQ ID NO:7)) were synthesized (SynGen, San Carlos, Calif.). The sequence of murine miR-124 is identical to human miR-124 on the basis of NCBI blast data. The treatment cohorts consisted of 20 µg of the miR-124 duplex or scramble control in 10 µL of PBS mixed with the vehicle (80 µL PBS containing 10 µL lipofectamine 2000; Invitrogen) or the vehicle control (90 µl PBS+10 µl lipofectamine 2000). The dosing was identical for intratumoral delivery or intravenous infusion. Mice were maintained in the M.D. Anderson Isolation Facility in accordance with Laboratory Animal Resources Commission standards and handled according to the approved protocol 08-06-11831.

6. Syngeneic Subcutaneous Model

The murine glioma GL261 cell line was obtained from the National Cancer Institute-Frederick Cancer Research Tumor Repository. On the basis of PCR expression, miR-124 expression in GL261 cells was 350-fold less than in normal murine brain. These cells were cultured in an atmosphere of 5% $CO_2$ and 95% humidified air at 37° C. in Dulbecco's modified Eagle's medium (Life Technologies; Grand Island, N.Y.), supplemented with 10% fetal bovine serum (Atlanta Biologicals, Norcross, Ga.), 1% penicillin/streptomycin (Life Technologies, Grand Island, N.Y.), and 1% L-glutamine (Life Technologies). The GL261 glioma cell cultures were divided every 3 days to ensure logarithmic growth. To induce subcutaneous tumors, logarithmically growing GL261 cells were injected into the right hind flanks of 6-week-old C57BL/6J female mice or nude mice at a dose of $4 \times 10^5$ cells suspended in 100 µl of Matrigel basement membrane matrix (BD Biosciences). When palpable tumors formed (approximately 0.5 cm in diameter), the mice (n=10/group) were treated by local tumor injection or intravenous injection. Tumors were measured every other day. Mice that showed signs of morbidity, high tumor burden, or skin necrosis were immediately euthanized according to M.D. Anderson guidelines. Tumor volume was calculated with slide calipers using the following formula: $V=(L \times W \times H)/2$, where V is volume ($mm^3$), L is the long diameter, W is the short diameter, and H is the height. Likewise, miR-124 or scramble miR was delivered systemically via the tail vein every other day.

7. Syngeneic Intracranial Glioma Model

To induce intracerebral tumors in C57BL/6J mice, GL261 cells were collected in logarithmic growth phase, washed twice with PBS, mixed with an equal volume of 10% methyl cellulose in Improved modified Eagle's Zinc Option medium, and loaded into a 250-µl syringe (Hamilton, Reno, Nev.) with an attached 25-gauge needle. The needle was positioned 2 mm to the right of bregma and 4 mm below the surface of the skull at the coronal suture using a stereotactic frame (Kopf Instruments, Tujunga, Calif.), as previously described (Heimberger et al., 2003). The intracerebral tumorigenic dose for GL261 cells was $5 \times 10^4$ in a total volume of 5 µl. Mice were then randomly assigned to control and treatment groups (n=10/group) Animals were observed three times per week, and when they showed signs of neurological deficit (lethargy, failure to ambulate, lack of feeding, or loss of >20% body weight), they were compassionately killed. These symptoms typically occurred within 48 hours of prior to death. The brains were removed and placed in 4% paraformaldehyde and embedded in paraffin.

8. Genetically Engineered Murine Models

Vector Constructs.

RCAS-PDGFB generation has been previously described (Dai et al., 2001). RCAS-STAT3 was created by amplifying the sequence encoding the cDNA by PCR using specially designed primers to enable directional cloning into a Gateway entry vector. The proprietary Gateway LR recombination reaction between the entry vector containing STAT3 and a Gateway-compatible RCAS destination vector resulted in the RCAS-STAT3 vector, which was sequence verified.

DF-1 Cell Transfection.

DF-1 immortalized chicken fibroblasts were grown in Dulbecco's modified Eagle's medium with 10% fetal bovine serum in a humidified atmosphere of 95% air/5% $CO_2$ at 37° C. Live virus was produced by transfecting plasmid versions of RCAS vectors into DF-1 cells using FuGene6. These cells were replicated in culture.

Verification of STAT3 Expression in Vector.

Untransfected DF-1 cells were grown in culture, transfected with RCAS-STAT3, and allowed to replicate for two to three passages. Cells were fixed with 4% paraformaldehyde, and immunocytochemical labeling was performed using standard methods. A rabbit polyclonal antibody against STAT3 (1:100; Cell Signaling Technology, Beverly, Mass.) and goat anti-rabbit Alexa Fluor 594 fluorescent conjugate (1:500; Molecular Probes, Carlsbad, Calif.) were used for detection. Prolong Gold anti-fade reagent with 4'-6-diamidino-2-phenylindole (DAPI) was used for labeling cell nuclei. Staining was visualized with a Zeiss Axioskop 40 microscope. Expression was secondarily validated by Western blot analysis.

In Vivo Somatic Cell Transfer in Transgenic Mice.

The transgenic Ntv-a mice are mixtures of different strains, including C57BL/6, BALB/c, FVB/N, and CD1. To transfer genes via RCAS vectors, DF-1 producer cells transfected with a particular RCAS vector ($5 \times 10^4$ DF-1 cells in 1-2 µl of PBS) were injected into the frontal lobes of Ntv-a mice at the coronal suture of the skull using a Hamilton Gastight syringe. The mice were injected on postnatal days 1 or 2, when the number of Nestin+ cells producing TVA is the highest. The mice were killed 90 days after injection or sooner if they demonstrated morbidity related to tumor burden. Their brains were removed and analyzed for tumor formation. Histologic verification of tumor formation and determination of tumor grade were performed by a neuropathologist.

Animal Randomization.

Twenty-one days after introducing the glioma-inducing transgenes RCAS-PDGFB and RCAS-STAT3, littermates to the treatment or control group (n=9/group) were randomly assigned. Mice were treated intravenously on Monday, Wednesday, and Friday for 3 weeks. After 90 days, the animals were compassionately killed, the CNS was fixed, and the tumors were analyzed immunohistochemically.

9. Statistical Analysis

The distribution of each continuous variable was summarized by its mean, standard deviation, and range. The distribution of each categorical variable was summarized in terms of its frequencies and percentages. Continuous variables were compared between treatment groups by a two-sample t test. In the case of comparing two paired groups, a paired t test is conducted. Kaplan-Meier curves were used to estimate unadjusted time to event variables. Log-rank tests were used to compare each time-to-event variable between groups. P values of less than 0.05 (two-sided) were considered statistically significant. All statistical analyses were performed using the Statistical Package for the Social Sciences v.12.0.0 (SPSS, Chicago, Ill.) and SAS v. 9.1 (SAS Institute, Cary, N.C.). Error bars represent SD.

B. Results 1. miR-124 Expression in Gliomas

Figure 1B:
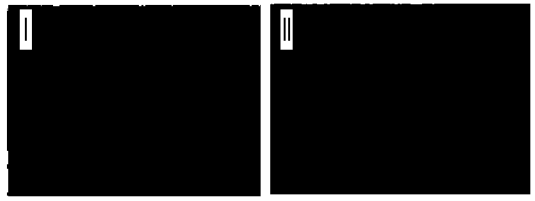
Figure 8A:
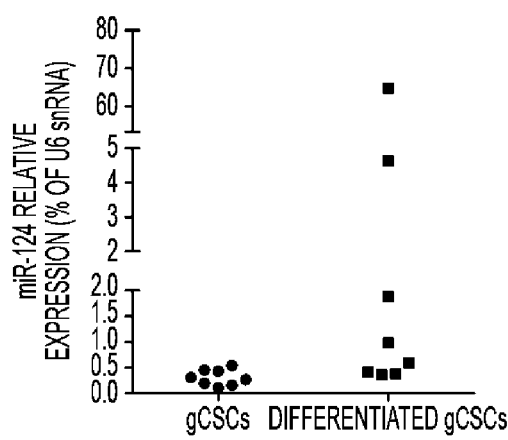
FIGS. 8A-B.
Figure 8B:
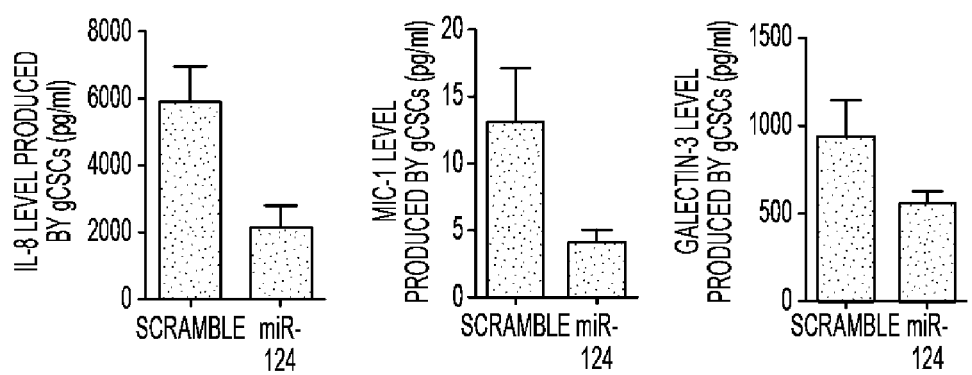

To determine the pattern of miR expression in glioblastoma relative to normal brain tissue, the Human miRNA OneArray Microarray v2 was used. miR-124 emerged as a leading candidate, with a mean 24.6-fold decrease in expression from that seen in normal brain tissue (Table 1). A subsequent analysis using reverse transcription-polymerase chain reaction (RT-PCR) confirmed that miR-124 was down regulated in glioblastoma GBM specimens (n=4), glioma cell lines (n=2), and gCSCs (n=4) compared with normal brain tissues (n=3) (FIG. 1A). When the gCSCs were placed under neural differentiation conditions, miR-124 expression levels were increased (FIG. 8). Because miR-124 was a leading candidate down regulated in glioblastoma, as observed by ourselves and others (27, 31), it determined whether it was decreased in other types of gliomas. Using a glioma tissue microarray and in situ hybridization, it was found that all glioma grades and types lacked miR-124 expression (FIG. 1B and Table 2). All cortex-containing neurons demonstrated positive expression of miR-124 (n=19). No differences in survival time among glioblastoma patients were found on the basis of the relative but negligible expression of miR-124 in The Cancer Genome Atlas data set.

TABLE 1

Altered miRNA expression of glioblastoma relative to normal brain

| miRNA | Relative downregulation | miRNA | Relative upregulation |
|---|---|---|---|
| miR-124 | 24.6 | miR-1273 | 3.7 |
| miR-3172 | 13.8 | miR-559 | 3.6 |
| miR-138 | 13.4 | miR-4286 | 3.2 |
| miR-3196 | 8.5 | miR-3152 | 3.1 |
| let-7b | 7.3 | miR-766 | 3 |
| let-7e | 6.9 | miR-542-3p | 2.7 |
| miR-1826 | 5.9 | miR-1302 | 2.7 |
| miR-1228* | 5.8 | miR-2355 | 2.7 |
| miR-4284 | 5.6 | miR-1285 | 2.6 |
| let-7d | 5.6 | miR-548c-5p | 2.5 |
| miR-3162 | 5.4 | miR-1281 | 2.3 |
| miR-874 | 5.2 | miR-1248 | 2.2 |
| let-7c | 5.2 | miR-1272 | 2.1 |
| miR-103 | 5 | miR-488* | 2.1 |
| miR-128 | 4.9 | miR-3192 | 2.1 |
| let-7a | 4.7 | miR-548d-5p | 2.1 |
| miR-26a | 4.5 | miR-3197 | 2.1 |
| miR-762 | 4.5 | miR-4323 | 2.1 |
| miR-7 | 4.2 | miR-3146 | 2 |

TABLE 2 miRNA expression incidence in gliomas

| Tumor pathologic type | WHO grade | % with miR-124 expression | N |
|---|---|---|---|
| Glioblastoma | IV | 0 | 150 |
| Gliosarcoma | IV | 0 | 6 |
| Anaplastic astrocytoma | III | 0 | 24 |
| Anaplastic mixed oligodendroglioma | III | 0 | 9 |
| Anaplastic oligodendroglioma | III | 0 | 16 |
| Mixed oligoastrocytoma | II | 0 | 5 |
| Oligodendroglioma | II | 0 | 24 |
| Low-grade astrocytoma | II | 0 | 1 |
| Subependymoma | I | 0 | 2 |

2. miR-124 Interacts with the STAT3 Pathway

To determine which miRs interact with STAT3, TargetScan was used to identify a group of miRs with conserved target sites in the STAT3 3'-UTR. Theoretically, these miRs can inhibit STAT3 expression and thus down regulate STAT3-mediated immune suppression in glioblastoma. The top-rated candidates were miR-124, miR-17, miR-125, and miR-129, with aggregate $P_{CT}$ scores of 0.85, 0.85, 0.84, and 0.58 (respectively) (Table 3).

TABLE 3

Predicted binding affinity of glioblastoma down-regulated miRNAs for STAT3

| miRNA | Conserved sites | | | Poorly conserved sites | | | Aggregate $P_{CT}$ |
|---|---|---|---|---|---|---|---|
| | Total | 8mer | 7mer | Total | 8mer | 7mer | |
| miR-124 | 1 | 1 | 0 | 0 | 0 | 0 | 0.85 |
| miR-17-5p | 2 | 0 | 2 | 1 | 0 | 1 | 0.85 |
| miR-125 | 1 | 1 | 0 | 0 | 0 | 0 | 0.84 |
| miR-129 | 0 | 0 | 0 | 3 | 1 | 2 | 0.58 |
| miR-29abc | 0 | 0 | 0 | 1 | 0 | 1 | 0.2 |
| miR-150 | 0 | 0 | 0 | 1 | 0 | 1 | 0.2 |
| miR-34a | 0 | 0 | 0 | 1 | 0 | 1 | 0.15 |
| miR-425 | 0 | 0 | 0 | 1 | 0 | 1 | 0.14 |
| miR-21 | 0 | 0 | 0 | 2 | 0 | 2 | 0.13 |
| miR-221 | 0 | 0 | 0 | 1 | 0 | 1 | 0.12 |
| miR-383 | 0 | 0 | 0 | 1 | 0 | 1 | 0.11 |
| miR-214 | 0 | 0 | 0 | 1 | 0 | 1 | 0.11 |

Figure 1C:
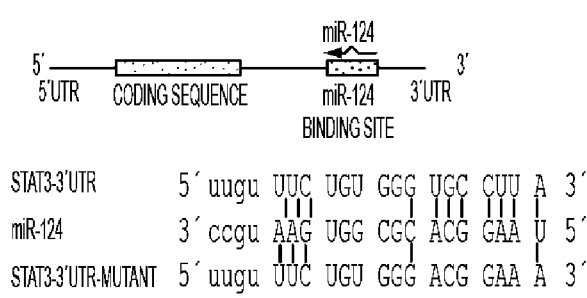
Figure 1D:
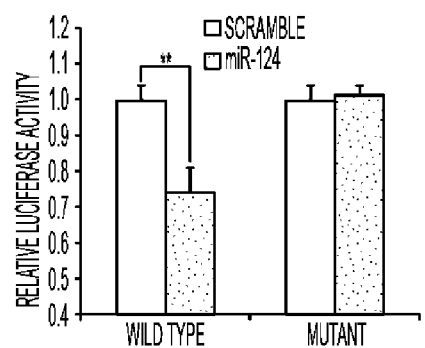
Figure 1E:
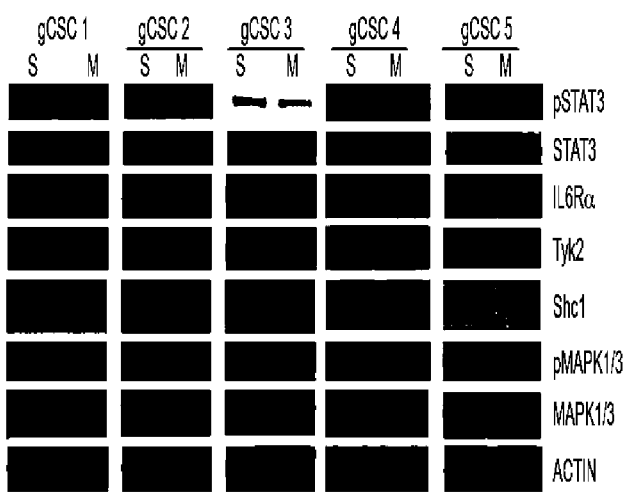

An additional analysis suggests that miR-124 is predicted to bind to STAT3. Therefore, on the basis of these cumulative bioinformatics data, a mechanistic and therapeutic evaluation of miR-124 was performed. Because the predicted binding sites of miR-124 to STAT3 are in a conserved, homologous region (FIG. 1C), it determined whether miR-124 directly inhibits STAT3 protein expression by binding to the 3'-UTR. miR-124-negative HeLa cells were transfected with pre-miR-124 plasmid or pre-miR-control plasmid. The 3'-UTR reporter activities of STAT3 were assessed by luciferase assays. miR-124 inhibited STAT3 luciferase activity in cotransfected HeLa cells (FIG. 1D), whereas directed mutational alteration of the miR-124 3'-UTR STAT3 binding site (FIG. 1C) resulted in complete abolishment of miR-124 inhibition of luciferase activity in cotransfected HeLa cells (FIG. 1D). Subsequently, both STAT3 and pSTAT3 expression at the protein level were inhibited by miR-124 within gCSCs as detected by Western blot (FIG. 1E).

Figure 9:
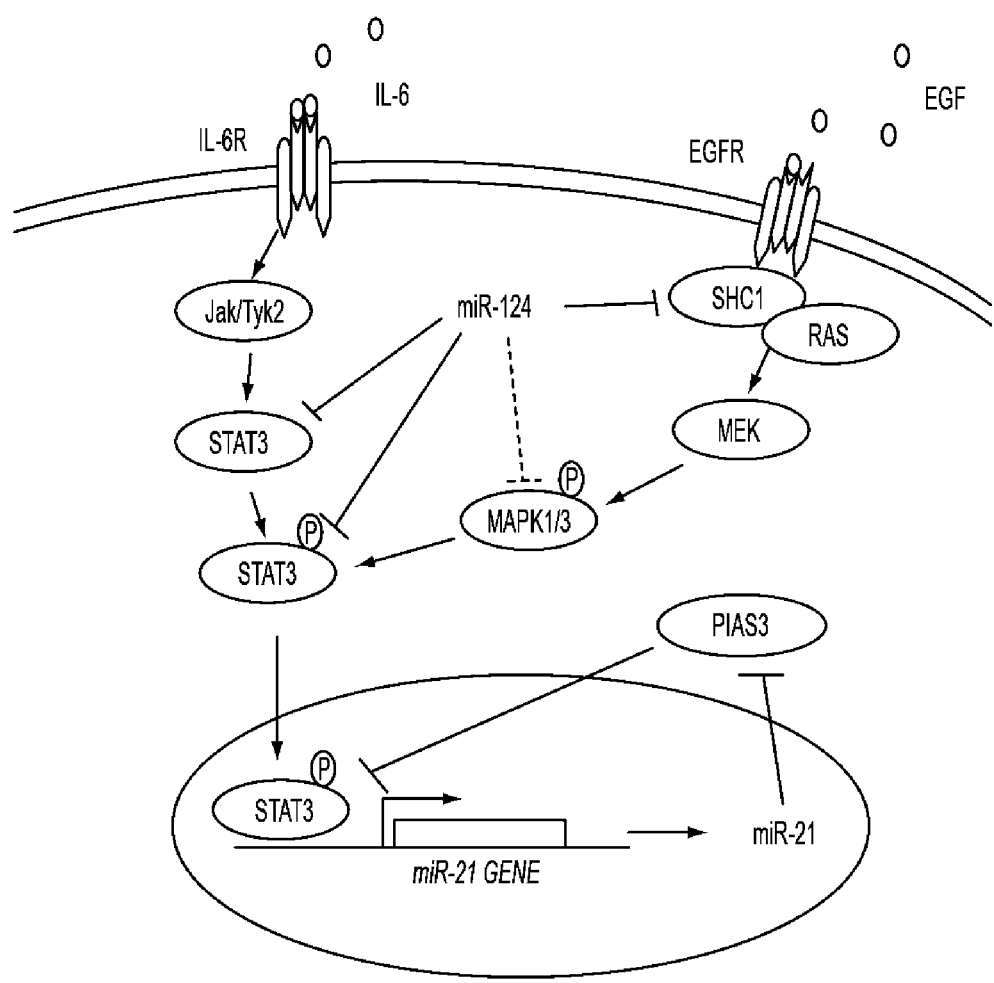
FIG. 9. Schema demonstrating how miR-124 can exert target effects on the STAT3 pathway in gCSC cells. STAT3 can be activated by a variety of ligands such as IL-6 or EGFR. miR-124 can not only down-modulate SHC1, STAT3, P-STAT3 in all tested gCSC cell lines but also, occasionally, pMAPK1/3, probably in a contextual fashion when the IL-6R ligand is not present and the gCSC is dependent on EGFR signaling.
Figure 10A:
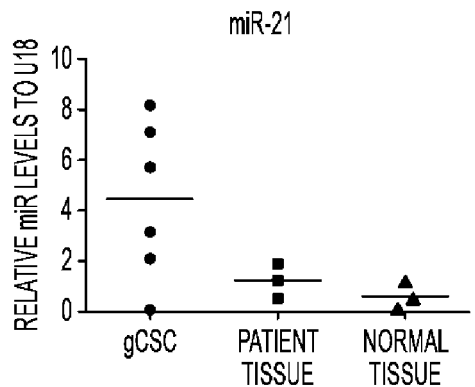
FIGS. 10A-C. miR-21 expression is higher in gCSCs and glioblastoma tumors than in normal brain and is inhibited by miR-124 overexpression.
Figure 10B:
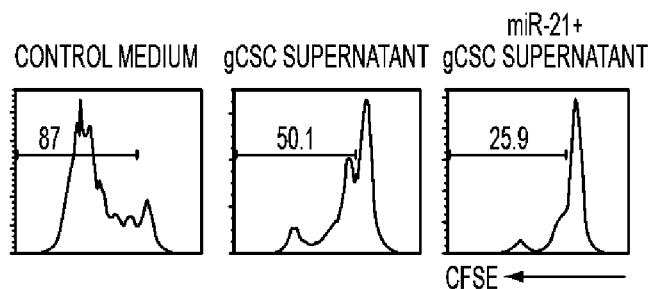
Figure 10C:
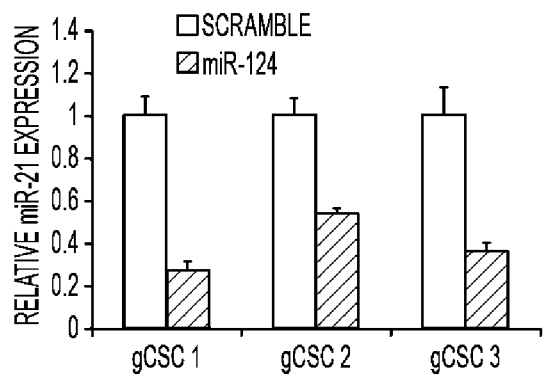

In addition to STAT3, TargetScan and other online software also suggest that miR-124 may target other components of the STAT3 signaling pathways including IL6Rα, Tyk2, Src homology 2 domain-containing transforming protein 1 (Shc1) and MAPK1 (Table 4). In order to test whether miR-124 suppresses these predicted targets, the effect of forced expression of miR-124 in five gCSCs isolated from different glioblastoma patients (FIG. 1E) was investigated. Shc1 is also a preferred target of miR-124 in gCSCs and is down regulated in all gCSCs treated with miR-124. pMAPK1/3 is down modulated in one gCSC cell line but this line is notable for the lack of IL-6Rα expression, suggesting that p-STAT3 activation may be due to alternative EGFR/MAPK1/3 dominant signaling. Although IL-6Rα, Tyk2, and MAPK1/3 are not preferred targets of miR-124 in gCSCs by Western blot, miR-124 can target at least two key components in the STAT3 signaling pathway (FIG. 9). To determine if miR-124 can down modulate targets downstream of p-STAT3 such as miR-21, miR-21 level in miR-124 overexpressing gCSCs by RT-PCR was measured and found that miR-21 expression was inhibited by miR-124 (FIG. 10).

analyzed using enzyme-linked immunosorbent assays (ELISAs) and cytokine and chemokine arrays. Here, lower levels of IL-8 (scramble: 5844±1108 pg/ml versus miR-124: 2115±672 pg/ml; n=4, $P<0.05$), galectin-3 (scramble: 933±214 pg/ml versus miR-124: 555±72 pg/ml; n=4, $P<0.01$), and MIC-1 (scramble: 13±4 pg/ml versus miR-124: 4±1 pg/ml; n=4, $P<0.05$) (FIG. 8) but not of VEGF were found. Cytokine and chemokine array data revealed a modest decrease in levels of TGF-$\beta_2$, macrophage migration inhibitory factor, Serpin E1, CX3CL1, CXCL10, CXCL16, and chemokine C—C motif-2, when miR-124 was overexpressed in gCSCs, but these findings were not statistically significant.

To determine whether miR-124 transfection reverses the functional gCSC-mediated immune inhibition of T-cells, anti-CD3/CD28 naïve CD4+ T-cells from healthy donors' PBMCs in the presence of gCSC medium were activated, 3-day gCSC-conditioned medium from gCSCs transfected with scramble control, miR-124, and miR-124 plus STAT3. The medium from scrambled miRNA-transfected gCSCs inhibited T-cell proliferation by 63.5±13.8% versus 33.0±10.1% in miR-124-transfected gCSCs (n=4, $P=0.023$) (FIG. 2B). Moreover, fewer apoptotic T-cells were induced by medium from miR124-transfected gCSCs than by medium from scramble-transfected gCSCs (FIG. 2C). Next, it was determined whether miR-124 could diminish forkhead box P3 (FoxP3)+Treg generation induced from naïve CD4+ T-cells, mediated by gCSC-conditioned medium.

TABLE 4

Target Scan predicted miR-124 binding sites of the molecules within the STAT3 signaling pathway

| | Conserved Sites | | | Poorly Conserved Sites | | | | Total context Score | Aggregate Pct |
|---|---|---|---|---|---|---|---|---|---|
| | Total | 8mer | 7mer-m8 | 7mer-1A | Total | 8mer | 7mer-m8 | 7mer-1A | | |
| STAT3 | 1 | 1 | | | | | | | −0.04 | 0.92 |
| IL-6Rα | 1 | 1 | | | 1 | 1 | | | −0.3 | 0.8 |
| Tyk2 | 1 | 1 | | | | | | | −0.33 | <0.1 |
| Shc1 | 1 | | 1 | | | | | | −0.19 | 0.87 |
| MAPK1 | 1 | | 1 | | | | | | −0.06 | 0.95 |

3. miR-124 Reverses gCSC-Mediated Immune Suppression

Figure 2D:
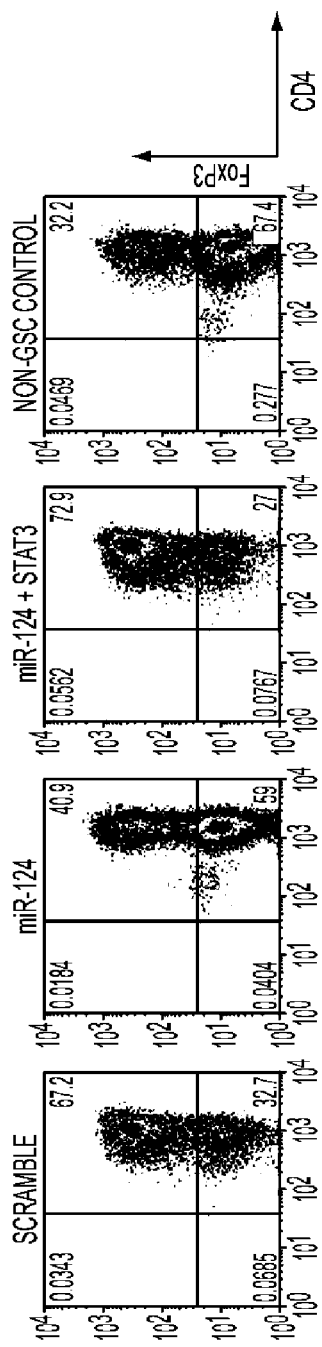
Figure 2E:
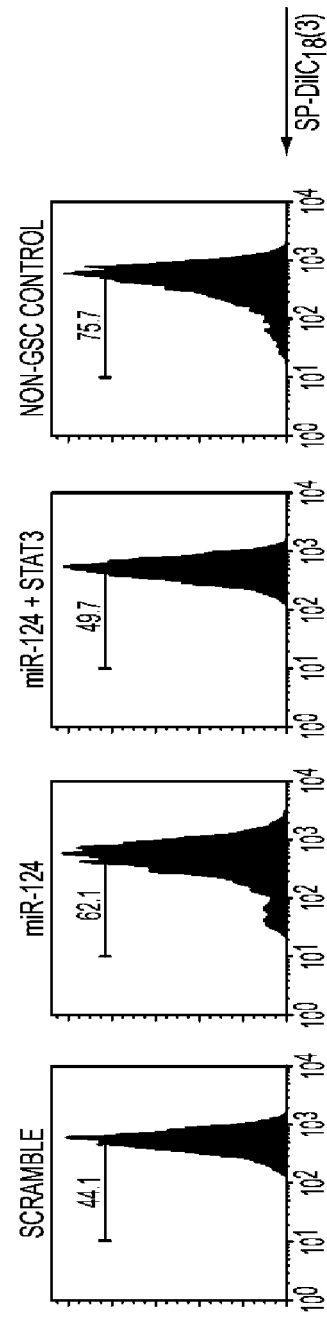

To determine the phenotypic consequences of up regulating miR-124, human immune-suppressive gCSCs (13) were transiently transfected with precursor miRs and confirmed the up regulation of miR-124 by RT-PCR. The miR-124 expression was increased in the range of 5-20,000 fold among different gCSCs. After 24 hours, gCSCs demonstrated increased adherence to the bottom of the plate, which was more pronounced after 48 hours. Specifically, the typical neurosphere morphology of the gCSCs was altered to become petri dish-attached with an elongated configuration and with contact inhibition (FIG. 2A). In contrast, transfection of astrocytes with miR-124 did not alter morphology, proliferation, apoptosis or cell cycle status. To characterize their immunological phenotype, gCSCs were assessed for their expression of major histocompatibility complex (MHC) I, MHC II, CD40, CD80, CD86, and B7-H1, by RT-PCR and flow cytometry after transfection with miR-124. No changes were found in MHC I, MHC II, CD40, CD80, B7-H1 or CD86 mRNA and protein expression levels. To determine what immune-suppressive soluble factors are affected by miR-124, the conditioned medium of miR-124- or scramble (control)-transfected gCSCs were Indeed, the medium from miR-124-transfected gCSCs led to decreased FoxP3+ T-cell generation compared with scrambled miRNA-transfected gCSCs (FIG. 2D). Moreover, these were functional Tregs, as assessed by autologous CD4+ T-cell proliferation in coculture assays (FIG. 2E). Furthermore, all the effects mediated by miR-124 were reversed by cotransfection of wild-type, constitutively active STAT3 lacking a miR-124 sensitive 3'-UTR fragment (FIG. 2B, C, D, E). In contrast, miR-21 enhanced gCSC-mediated immune suppression as assessed by suppression of T-cell proliferation (FIG. 10).

Figures 3A, 3B, 3C, 3D:
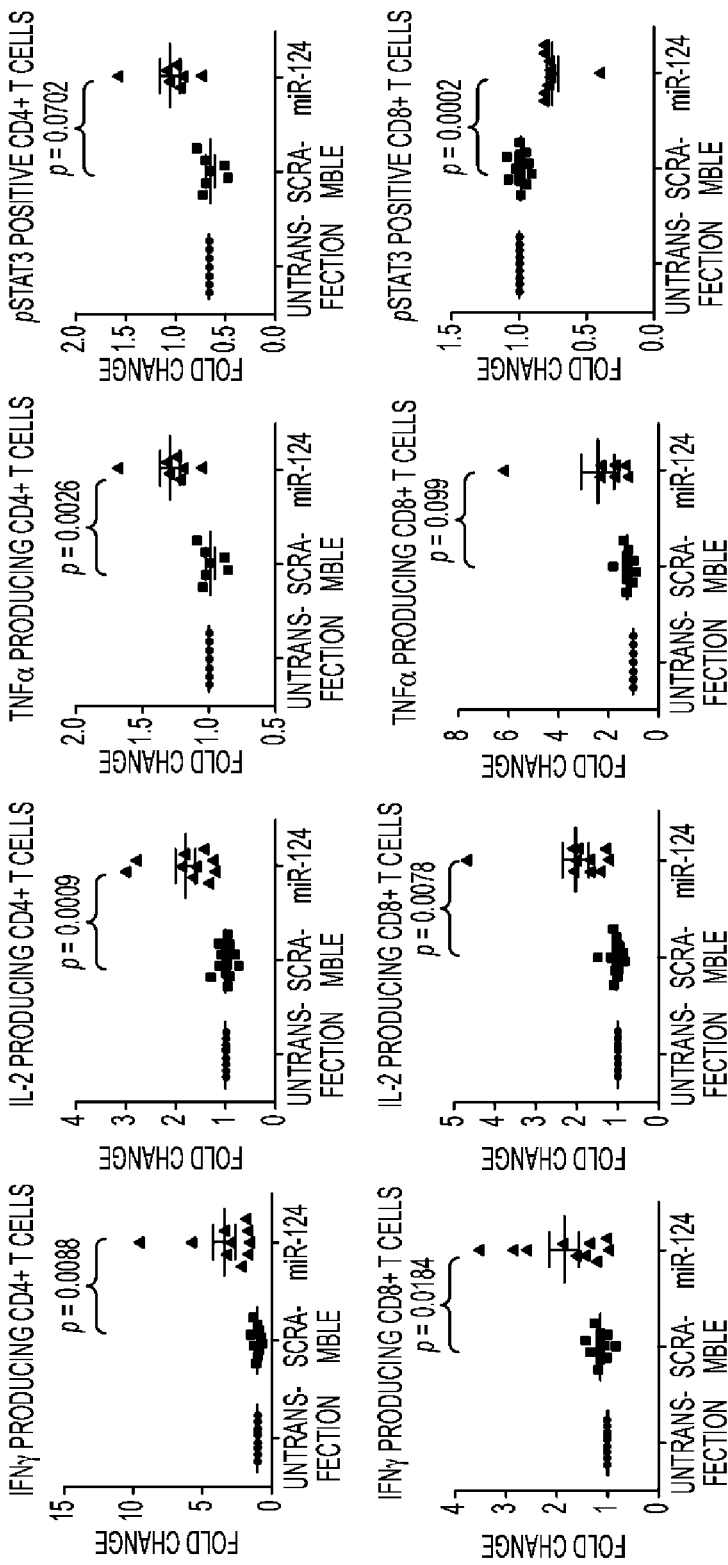
FIGS. 3A-D. miR-124 enhances T-cell effector cytokine production in glioblastoma patients. PBMCs were isolated from the freshly drawn blood of glioblastoma patients undergoing resection, transfected with miR-124 or scramble control oligonucleotides, and sequentially stimulated with anti-CD3/anti-CD28 antibodies for T-cell proliferation. miR-124 administration significantly enhanced effector cytokine responses, such as IFN-γ (n=10) (FIG. 3A), IL-2 (n=10) (FIG. 3B), and TNF-α (n=7) (FIG. 3C), in both CD4+ T and CD8+ T-cells of PBMCs from glioblastoma patients. miR-124 up regulation suppressed pSTAT3 activity in CD8+ T-cells (n=9) and to a lesser degree in the CD4+ T-cells (n=9) (FIG. 3D). Each symbol represents PBMCs from different patients without transfection or with transfection with either the scramble control or miR-124.

Because miR-124 can modify the immune-suppressive function of gCSCs, it was determined if it could exert a direct effect on the immune effector function in immunosuppressed glioblastoma patients. PBMCs were obtained from patients newly diagnosed with glioblastoma during tumor resection. The baseline miR-124 expression in glioblastoma patient's T-cells (n=4) and normal donors (n=4) is undetectable when determined by RT-PCR. The T-cells were stimulated and simultaneously transfected with the scrambled control oligonucleotides or with miR-124. Levels of IL-2, tumor necrosis factor (TNF)-α, and interferon (IFN)-γ were significantly increased in miR-124-transfected CD4+ T-cells and CD8+ T-cells (FIG. 3). In parallel, it was also observed that miR-124 overexpression in healthy donor peripheral blood T-cells enhances production of effector cytokines, such as IFN-γ, TNF-α, and IL-12, from CD4+ and CD8+ T-cells.

4. miR-124 Inhibits In Vivo Glioma Growth

Figure 4A:
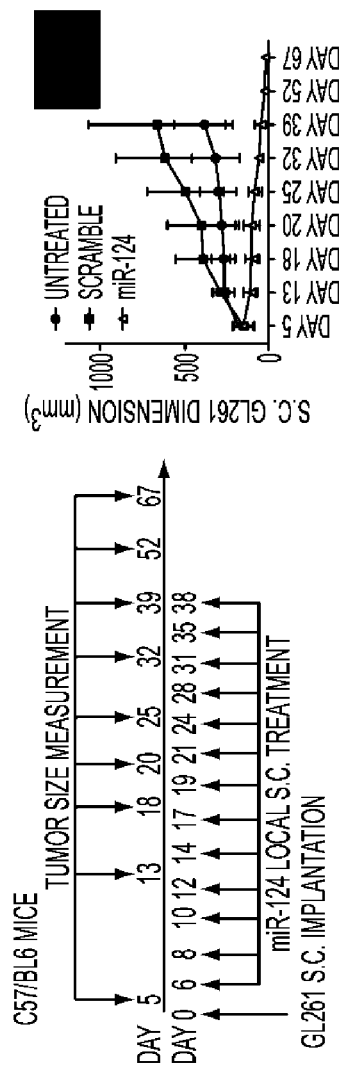
FIGS. 4A-F. miR-124 exerts potent efficacy to suppress subcutaneous GL261 tumors in a syngeneic mouse model.
Figure 4B:
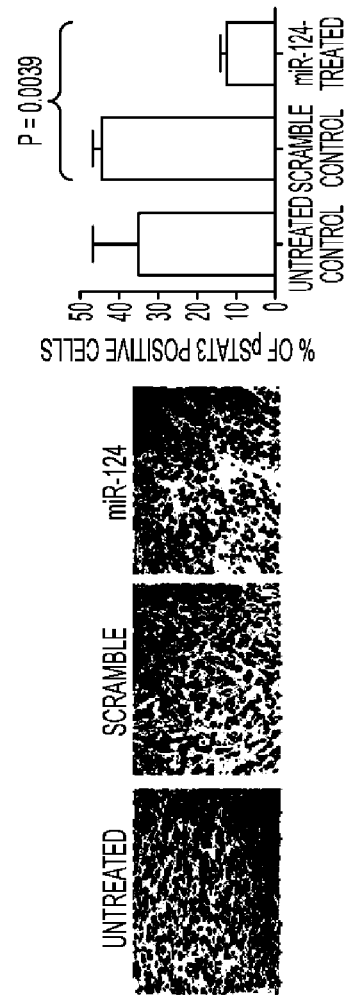

Given miR-124's role in modulating the STAT3 pathway and immune responses, whether miR-124 could exert a therapeutic effect in vivo was determined next. To assess the in vivo antitumor efficacy of miR-124, GL261 murine glioma cells were implanted into immune competent C57BL/6 mice and treated them with miR-124 or scramble control (n=10 per group). After the subcutaneous GL261 tumors had grown to a palpable size, miR-124 duplex or scramble control was administered. Subcutaneous tumor growth progressed in all the C57BL/6J mice treated with the scramble control. In contrast, in the miR-124-treated group, the tumor volume was markedly suppressed (P=0.01) (FIG. 4A). Gliomas started to shrink as soon as miR-124 was administered; moreover, the tumors continued to regress even after miR-124 treatment was discontinued. In contrast, tumors kept growing aggressively in scramble microRNA-treated and untreated tumor-bearing mice groups. An immunohistochemical analysis revealed that p-STAT3 glioma expression levels were markedly inhibited in the miR-124-treated cohort (P=0.0039) (FIG. 4B).

Figure 4C:
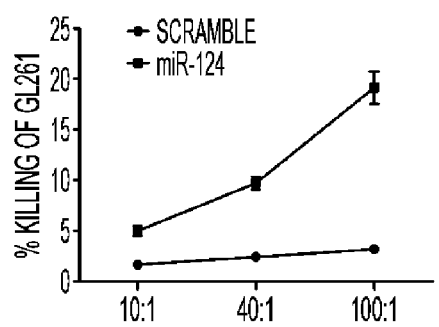
Figure 4D:
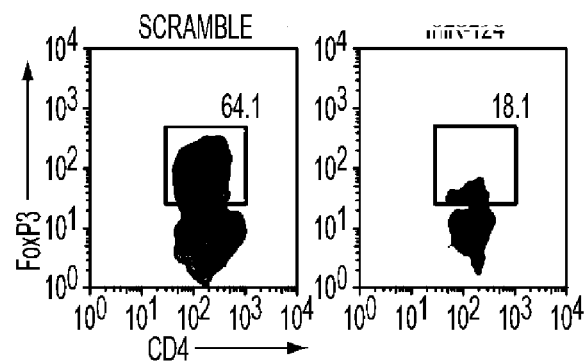
Figure 4E:
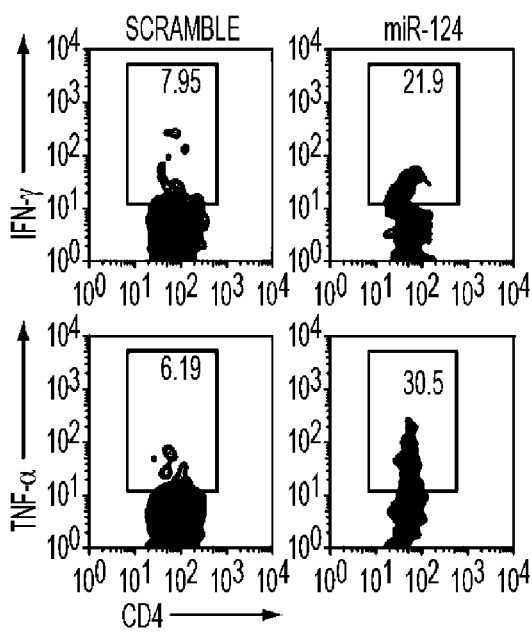
Figure 4F:
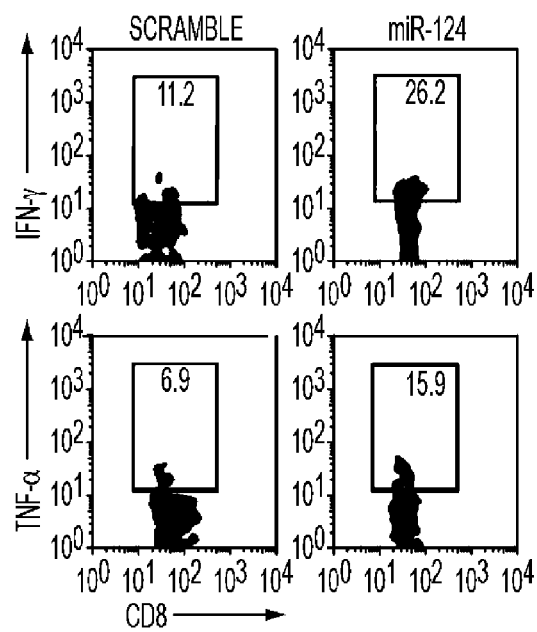
Figure 11:
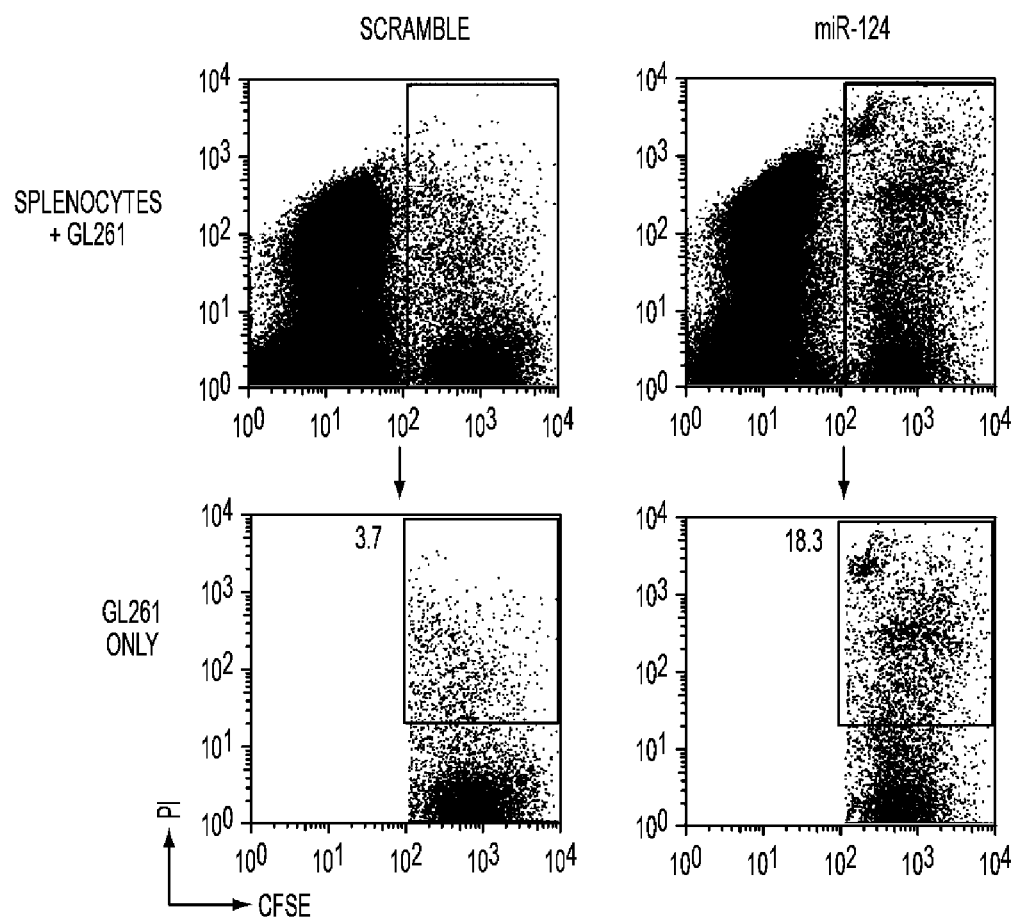
FIG. 11. Ex vivo splenocytes from miR-124 treated intracranial GL261 mice have markedly increased cytotoxicity at 48 hours after coculture with GL261 cells compared to splenocytes from scramble control oligonucleotide-treated GL261-bearing mice. The ratio of splenocytes to GL261 cells is 100:1. Representative dot plots of duel PI- and CFSE-labeled GL261 cells with splenocytes and the associated gating strategy are shown to demonstrate how the target cells (GL261) are identified and quantified.

To determine whether enhanced immunological tumor cytotoxicity was correlated with miR-124's efficacy in vivo, the immune cytotoxic responses directed toward GL261 glioma cells were evaluated. Splenocytes from tumor-bearing mice treated with miR-124 duplex or scramble miRNA were isolated and cocultured with CFSE-labeled GL261 target cells for 48 hours. The immune cells from the tumor-bearing mice treated with miRNA-124 increased the cytotoxic clearance of the GL261 target cells relative to that in scramble-treated mice (P<0.05) (FIG. 4C and FIG. 11). Ex vivo GL261 tumor tissues from miR-124- or scramble microRNA-treated tumor-bearing mice were analyzed and found that the percentage of FoxP3+ Tregs in the tumor microenvironment was reduced to 19.0±8.8% in the miR-124-treated group (n=3) compared with 64.7±5.4% in the scramble-treated group (n=3) (P=0.0015) (one representative FACS plot shown as FIG. 4D). No significant decrease in the number of FoxP3+ Tregs in the spleen or lymph nodes of miR-124-treated tumor-bearing mice was observed relative to control-treated mice, indicating that miR-124's Treg modulatory effects were confined to the tumor. To determine whether miR-124 mediates an enhanced immune activation of effector T-cells in the tumor microenvironment, the production of effector cytokines such as IFN-γ and TNF-α in tumor-infiltrating T-cells was determined Consistent with the enhanced antitumor activity in the miR-124-treated group, a marked increase in effector cells (i.e., producing IFN-γ or TNF-α) was found in the glioma microenvironment, including CD4+ T-cells (FIG. 4E; IFN-γ: from 7.7±2.0% to 21.6±3.3%, P=0.0032; TNF-α: from 6.4±1.7% to 29.1±7.4%, P=0.0066) and CD8+ T-cells (FIG. 4F; IFN-γ: from 10.9±3.3% to 26.0±4.0%, P=0.007; TNF-α: from 6.4±1.7% to 16.4±1.7%, P=0.0019).

5. The Therapeutic Effect of miR-124 is Immune Mediated

Figure 5A:
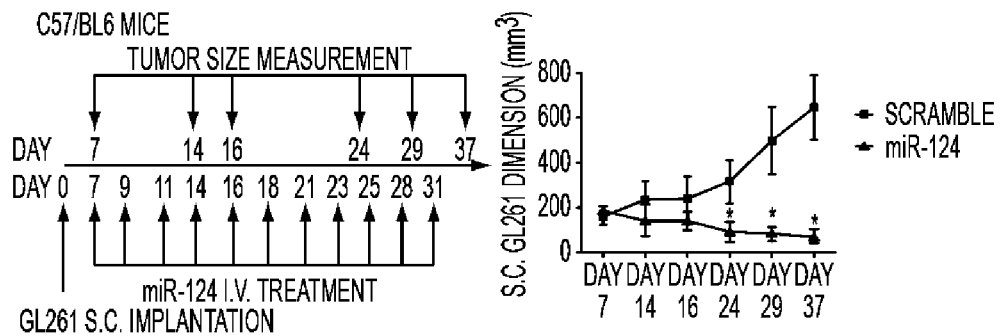
FIGS. 5A-D. The therapeutic effect of miR-124 is lost in immune-incompetent models.
Figure 5B:
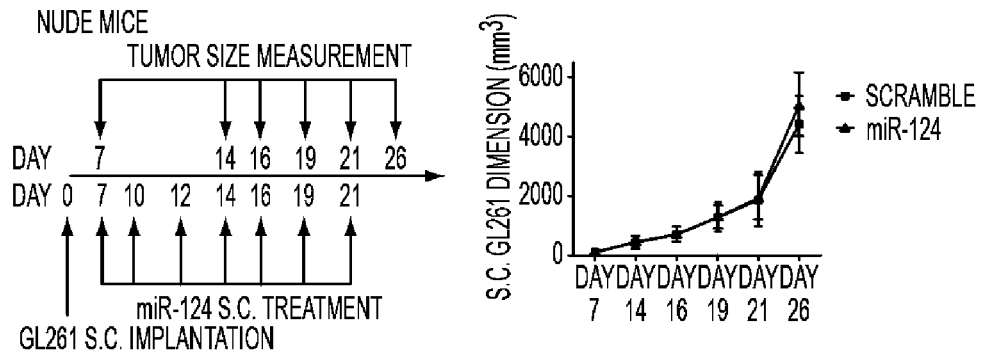
Figure 5C:
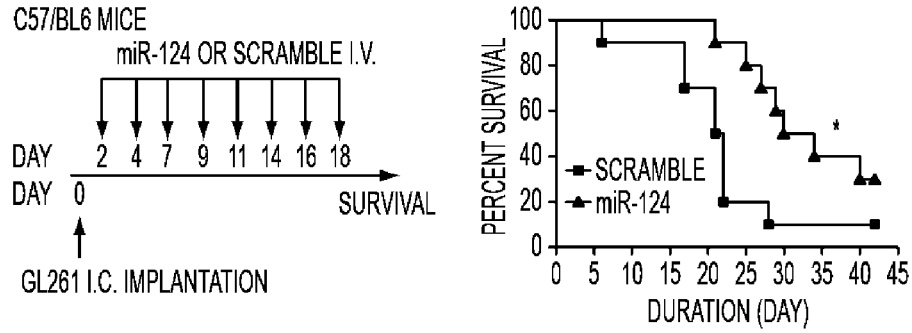
Figure 5D:
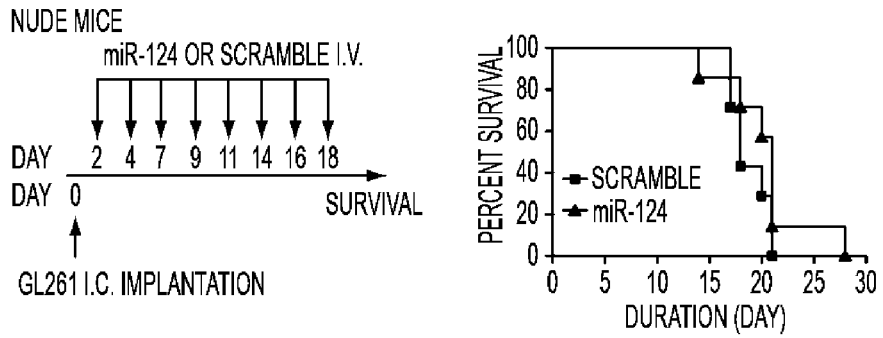

Although, the miR-124 had a therapeutic effect when injected directly into the tumor, this is unlikely to be a viable therapeutic approach for patients. Therefore, intravenous miR-124 administration was tested in established murine glioma models. Confirming the results of the direct delivery approach, intravenous administration of miR-124 led to marked inhibition of glioma growth in vivo (FIG. 5A). To determine whether this therapeutic effect was secondarily mediated by the immune system, GL261 murine glioma cells were implanted in immune-incompetent (nude) mice and treated them with miR-124 or scramble control. Intratumoral treatment was initiated when the tumors grew to a palpable size. In the immune-incompetent animal background, miR-124 failed to exert a therapeutic effect, indicating that miR-124 mediates in vivo activity via the immune system (FIG. 5B). To determine whether treatment with miR-124 was effective against established intracerebral tumors, miR-124 was administered to C57BL/6J mice with intracerebral tumors from GL261 cells, starting after tumor cell implantation. The median survival duration for the scramble control group was 21.5 days. For mice treated with miR-124, the median survival duration was 32 days (P=0.02) (FIG. 5C). When the experiment was repeated in an immune-incompetent model system, therapeutic efficacy was once again lost (FIG. 5D).

6. The Immune Therapeutic Efficacy of miR-124 Depends on T-Cells

To further investigate which T-cell compartment mediates miR-124's in vivo antitumor activity, CD4+ or CD8+ T-cells in GL261 tumor-bearing mice were depleted with neutralizing antibodies while treating those mice with miR-124 or scramble RNA oligonucleotides. The depletion of both CD4+ T-cells and CD8+ T-cells completely abrogated the anti-glioma efficacy of miR-124 (FIG. 6A), indicating that CD4+ and CD8+ T-cells are critical immune cell components mediating miR-124 therapeutic efficacy in vivo. In order to determine whether CD3+ T-cells are directly targeted during intravenous administration of miR-124, CD3+ T-cells were isolated from the peripheral blood, spleens and GL261 tumors and measured the expression of miR-124 by quantitative RT-PCR. There is minimal baseline expression of miR-124 in the T-cells from non-tumor bearing and GL261-bearing mice (FIG. 12). After in vivo miR-124 treatment, there is an increase in the miR-124 expression levels in both the peripheral blood T-cells and within the glioma-infiltrating T-cells. This coincided with decreased intracellular p-STAT3 expression (FIG. 12).

Next, CD3+ T-cells were isolated, transfected with miR-124 or scramble control, and expanded their numbers in vitro for 48 hours before adoptively transferring these cells into GL261 tumor-bearing mice. This miR-124 transfection inhibited p-STAT3 activity in the adoptively transferred T cells (FIG. 6B). Consistent with miR-124-enhanced T-cell effector function (as shown in FIG. 3) and the miR-124 therapeutic effects relying on T-cells (as shown in FIG. 6A), it was found that GL261 gliomas regressed upon adoptive transfer of miR-124-transfected T-cells but not with control scramble-transfected T-cells (FIG. 6C), further demonstrating the pivotal role of the immune system in miR-124-mediated antitumor effects. To investigate the in vivo cellular mechanisms of adoptively miR-124-transfected T-cell treatment, the percentage of infiltrating CD4+ T-cells, CD8+ T-cells and FoxP3+ Tregs in the GL261 tumors 6 days after treatment with the miRNA-transfected CD3+ T-cells was determined Within the glioma microenvironment, there was an increase in the CD4+ T-cell infiltration from 2.6±0.9% in the scramble-control transfected CD3+ T-cell treated group to 7.4±1.9% in the miR-124-transfected CD3+ T-cell treated group (P=0.04, n=3 per group), a decrease in FoxP3+ Tregs from 26.9±5.9% to 7.0±0.3% in the respective groups (P=0.014), but no change in the absolute numbers of CD8+ T-cell infiltration. Similar to the findings in FIGS. 4E and F, there was a marked increase in immune effector cells within the glioma microenvironment after treatment with the miR- 124-transfected T-cells; specifically, in the CD4+ T-cell compartment (IFN-γ: from 3.7±2.2% in the scramble-control transfected CD3+ T-cells to 22.5±6.2% in the miR-124-transfected CD3+ T-cells, P=0.023; TNF-α: from 4.1±1.9% to 17.2±2.6%, P=0.0076). Although there was no increase in the absolute number of CD8+ T-cells, the effector status of the CD8+ T-cells within the glioma microenvironment was enhanced (IFN-γ: from 1.4±0.7% to 7.3±1.8%, P=0.0018; TNF-α: from 5.2±0.8% to 15±4.4%, P=0.043).

7. miR-124 Modulates T Helper Cell Differentiation

Figure 13:
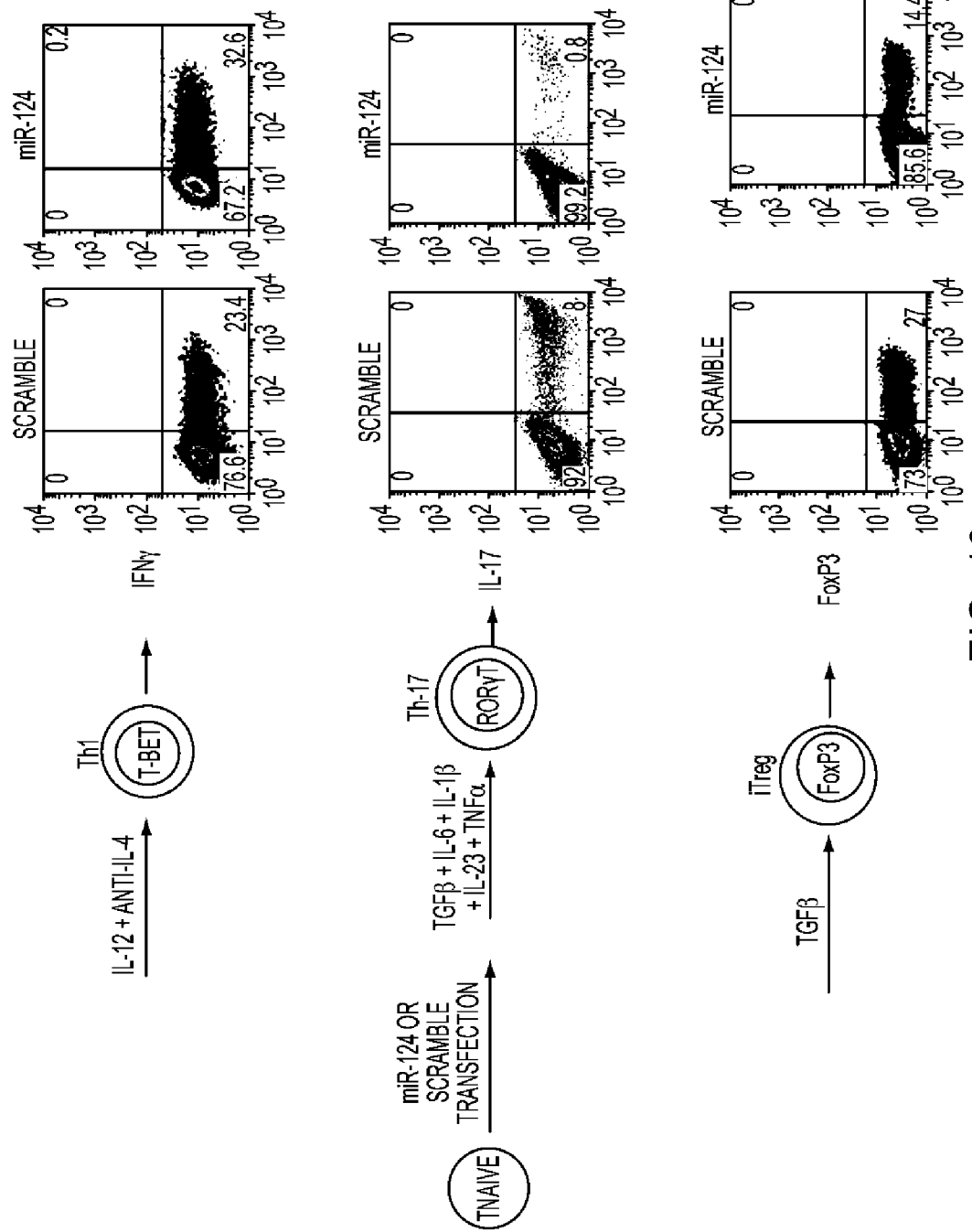
FIG. 13. miR-124 modulates Th1, Th17, and inducible Treg differentiation. CD4+CD45RA+CD45RO-naïve T-cells were isolated from healthy donor PBMCs and stimulated with plate-bound anti-CD3 and soluble anti-CD28 under Th1, Th17, and inducible Treg polarization conditions before miR-124 transfection. After 3 rounds of T-cell stimulation and polarization, cytokine production in the different Th populations was quantified by intracellular cytokine FACS. One representative set of data was shown, but similar results were obtained from two additional independent experiments.

To further investigate whether Th1 and Th17 differentiation are responsive to modulation with miR-124, CD4+ CD45RA+CD45RO-naïve T-cells were activated with plate-bound anti-CD3 and soluble anti-CD28 under Th1, Th17, and inducible Treg polarization conditions before miR-124 transfection. IL-17A+Th17 cells and FoxP3+ Treg induction was inhibited when miR-124 was overexpressed, whereas miR-124 promoted differentiation of IFN-γ+Th1 cells (FIG. 13).

8. miR-124 Exerts a Therapeutic Effect in STAT3-Expressing Genetically Engineered Murine Models The limitation of evaluating therapeutic strategies in clonotypic models has been previously noted (Huse et al., 2009); a genetically engineered murine model was created that expresses STAT3 (Doucette et al., 2012). newborn Ntv-a mice were injected with RCAS-STAT3 and RCAS-PDGFB vectors to reproducibly and consistently obtain high-grade gliomas, with the defining histologic features of microvascular proliferation, necrosis, and invasion (FIG. 7A) and lacking miR-124 expression (FIG. 7B). Similar to the findings in glioma patients, miR-124 expression in these induced gliomas was also markedly diminished. To determine whether treatment with miR-124 was also efficacious in this model system, Ntv-a mice were treated with miR-124, starting on day 21 after tumor induction. No behavioral or neurological abnormalities of the mice were noted during treatment. The median survival duration in the control group was 26 days. In mice treated with miR-124, the median survival duration was 39 days (P=0.04) (FIG. 7C). Necropsies of glioma-bearing Ntv-a mice revealed that the miR-124-treated cohort had a lower incidence of high-grade gliomas, as determined by the study neuropathologist, on the basis of the characteristic features of necrosis and neovascular proliferation (FIG. 7D). Furthermore, there was no evidence of demyelination, macrophage infiltration, or lymphocytic infiltration in the non-tumor bearing areas of the CNS that would indicate the induction of autoimmunity Systemic administration of miR-124 resulted in lower p-STAT3 expression in the gliomas than in scrambled miRNA and untreated controls (FIG. 7E).

These experiments demonstrate that miRNA approaches can be exploited for immune therapeutic purposes against malignancies. A significant confounding factor in the translational implementation of miR-based approaches has been adequate delivery to the target tumor cells. To circumvent this, a miRNA that could reverse tumor-mediated immune suppression—specifically, a key molecular hub, STAT3—resulting in immunological recognition and clearance of the malignancy was selected. This disclosure also describes a strategy for identifying potential miRNA immune therapeutics that may be applicable to other types of malignancies by sequentially: 1) screening for down-modulated miRNAs using tumor microarrays; 2) determining the scope of potential use in humans by in situ hybridization of tissue microarrays; 3) screening and selecting the miRNA candidates that target immunosuppressive pathways and/or mechanisms; and 4) evaluating mechanism and therapeutic effect within immune competent model systems. While the STAT3 target was used as a proof of principal, other immunosuppressive targets such as CTLA-4, PD-1, and transforming growth factor-β could be used. Several other candidate miRNAs identified in the human glioblastoma miRNA microarray expression library likely target several of these as well and are also being evaluated for their potential as therapeutic agents in a complementary or alternative fashion with miR-124.

The findings support the immune modulatory effects of miR-124. First, in vivo therapeutic efficacy was ablated in immune-incompetent murine model systems. Second, miR-124 transfection reduced the immune-suppressive properties in gCSCs, including inhibiting secretion of immune-suppressive cytokines such as galectin-3 (which is downstream from the STAT3 pathway (Wei et al., 2010) and induces T-cell apoptosis, promotes tumor growth, and induces Tregs), MIC-1 (which inhibits macrophage production of antitumor TNF-α), and IL-8 (which induces immune chemotaxis and is a potent promoter of angiogenesis). Furthermore, inhibition of T-cell proliferative responses and effector functions by the gCSCs was reversed upon transfection with miR-124. The restoration of T-cell IFN-α effector functions with miR-124 is consistent with a previous report that STAT3 negatively regulates IFN-α (Murray, 2006). Third, miR-124 treatment of T-cells from immune-suppressed glioblastoma patients induced potent effector responses, including IL-2 and IFN-γ production. Fourth, the immune responses in the glioma microenvironment in miR-124-treated murine models demonstrated an enhancement of proinflammatory effector CD4 and CD8 T-cells, with diminished Treg intratumoral trafficking. Finally, ex vivo glioma cytotoxicity assays from miR-124-treated mice demonstrated enhanced glioma killing. Cumulatively, these data are consistent with those of previous studies that demonstrated that modulating the STAT3 pathway in the immune cell population is sufficient to mediate efficacious antitumor immune responses (Kortylewski et al., 2005).

STAT3 signaling has been shown to be a key regulator of microglia/macrophage—mediated immune-suppression (Wu et al., 2010). MiR-124 is low or undetectable in these cells; thus miR-124 administration may abolish or reverse their immune suppression by down-regulating STAT3 activity. Although this study focused on adaptive anti-tumor immune responses, it cannot exclude that part of the therapeutic effect was mediated via innate immunity Other investigators have shown that the peripheral administration of miR-124 in an experimental murine autoimmune encephalomyelitis model caused deactivation of macrophages, reduced activation of myelin-specific T cells and markedly suppressed the disease (Ponomarev et al., 2011). This discrepancy can be explained by the contextual target—i.e. miR-124 targets overactive C/EBP-α-PU.1 signaling in the context of induced autoimmunity versus STAT3 signaling in the glioma microenvironment with the resulting contrasting immune functional differences.

When data from The Cancer Genome Atlas were used to compare miR-124 expression and survival in patients with glioblastoma, no differences in patient outcome were identified; however, the miR-124 expression levels were negligible in these patients, and the marginal differences are probably attributable to the submitted specimens containing intervening miR-124-expressing infiltrating neurons. Given miR-124's role in neuronal development, it was not unexpected to find it expressed in the normal CNS as assessed by in situ hybridization. miR-124 expression was lost across all grades and types of gliomas, suggesting not only that this loss is an early event in glioma initiation and development but also that miR-124 therapeutic approaches will be useful in a variety of gliomas.

On the basis of multiple predictive binding algorithms, luciferase expression assays, and mutational analyses, miR-124 appears to down regulate the expression of STAT3, including the activated form, p-STAT3. This finding was further supported by the results of in vitro studies that demonstrated p-STAT3 inhibition in human gCSCs and immune cells and in vivo in the local glioma microenvironment. These data are also consistent with a recent publication demonstrating that miR-124 binds to the STAT3 3'-UTR in the rat cardiomyocyte (Cai et al., 2012). However, miR-124 also targets other components of the STAT3 signaling pathway such as Shc1. Although IL-6Rα has been proved to be a target of miR-124 in hepatocarcinoma cell lines (Hatziapostolou et al., 2011), this was not the case in any of the gCSCs, indicating that miR-124 has differential targets in various cells or tissues. Shc1 is not present in normal brain but is expressed in all grades of gliomas (Magrassi et al., 2005). In glioma patients, the loss of miR-124 may result in the expression of Shc1, which assembles the EGFR/MAPK1/3 signaling complex, thereby enhancing the activation of this signaling pathway. Because Shc1 is upstream of MAPK1/3 in the EGFR/MAPK1/3 signaling pathway, the reduced p-MAPK1/3 level might be due to the down regulation of Shc1 by miR-124. However, down modulation of Shc1 in most of the gCSCs did not correlate with down modulation of p-MAPK1/3. In the one gCSC that demonstrated reduced p-MAPK1/3 expression, the IL-6Rα expression was absent, indicating a potential greater reliance on the EGFR/MAPK1/3 signaling pathway and illustrates that although miR-124 inhibits p-STAT3, inhibition of other components of the signaling axis are contextual and hierarchical.

Other than by immune regulation, miR-124 may also reduce gliomagenesis via multiple mechanisms, including inducing gCSC differentiation, targeting multiple oncogenic signaling pathways (such as NFATc and PIK3CA), and repressing tumor cell proliferation (Lujambio et al., 2007), if sufficient levels of miR-124 are able to enter the CNS. The data in the miR-124-treated Ntv-a glioma model demonstrated a decreased incidence of high-grade glioma, probably secondary to the diminished p-STAT3 expression in the local tumor microenvironment. This finding confirms those of previous studies that have linked miR-124 to gliomagenesis.

An advantage of intravenous administration of miR-124 is the ease of translational implementation as opposed to siRNA approaches that have required ex vivo transduction of the cancer cells (Scuto et al., 2011), direct tumor delivery (Bjorge et al., 2011), knock-out in the hematopoietic cell population (Kortylewski et al., 2005), or conjugation to CpG to target the immune population (Kortylewski et al., 2009). Moreover, it is possible that the physiological expression of miR-124 in normal brain tissues confers tolerance to exogenous administration of this miRNA, thus minimizing toxicity. Indeed, no evidence of CNS toxicity or induced autoimmunity in treated mice was observed. Alternatively, because miR targets "networks" as opposed to a singular target, as is the case with siRNA, other unidentified therapeutic targets may be contributing to the beneficial in vivo effects observed with the miR-124. Specifically, miR-124 has been previously shown to target a variety of mRNAs (Lim et al., 2005) and it was found that it can also target miR-21, which is regulated by STAT3 (Loffler et al., 2007). miR-21 has been shown to be significantly elevated in glioblastomas and can regulate multiple genes associated with preventing glioma cell apoptosis (Chan et al., 2005) and enhancing migration and invasion (Gabriely et al., 2008). miR-21 inhibition can inhibit the growth of glioblastoma cells in vitro (Zhou et al., 2010) and in vivo (Gaur et al., 2011; Corsten et al., 2007). Thus, a component of the observed in vivo therapeutic effect could be secondary to the modulation of miR-21 by miR-124.

In summary, these findings show that systemic delivery of immune-modulatory miRNAs may be used as anticancer therapeutic modality Immune modulatory miRNAs may be used in combination and delivered in the context of nanoparticles, liposomes or exosomes or used to modify cellular vaccine strategies. Because the STAT3 pathway has been shown to mediate resistance to chemotherapeutics by modulating miR-17 (Dai et al., 2011), miR-124 may also have a therapeutic role in the setting of treatment failure. Screening miRNA expression in tumors used in personalized medicine approaches.

Example 2 miR-142-3p Inhibits the M2 Macrophage and Exerts Therapeutic Efficacy Against Murine Glioblastoma A. Materials and Methods 1. Isolation of Human Glioblastoma-Infiltrating Macrophages and CD14+Monocytes Tumors were confirmed as glioblastoma (World Health Organization grade IV) by a board-certified neuropathologist. Tumors were washed in RPMI medium and dissected to remove blood products and surrounding non-tumor brain tissue. Tumor tissue was broken down into smaller pieces and digested for 2 hours using a cancer cell isolation kit (Panomics, Santa Clara, Calif.). The cells were suspended in RNAlater solution (Ambion, Austin, Tex.) in RNase-free tubes and stored at 4° C. overnight; after 24 hours, they were transferred to −20° C. until needed for total RNA extraction. Total RNA from normal brain tissues was obtained from Biochain (Hayward, Calif.).

After the glioblastomas were placed into single cell suspension, the glioblastoma-infiltrating macrophages were also isolated based on further refinement of the glioma-infiltrating macrophage isolation protocol by performing CD11b+MACS positive selection after Percoll gradient centrifugation to achieve over 95% purity (Hussain et al., 2006). Human PBMCs were prepared from healthy donor blood (n=4) (Gulf Coast Blood Center, Houston, Tex.) and from glioblastoma patients undergoing resection (N=4) at The University of Texas MD Anderson Cancer Center (Houston, Tex.) by centrifugation on a Ficoll-Hypaque density gradient (Sigma-Aldrich, St. Louis, Mo.). Human CD14+ monocytes were purified from the PBMCs by anti-CD14 microbeads magnetic cell sorting, according to the manufacturer's instructions (Miltenyi Biotec, Cambridge, Mass.). The purity and viability of the monocytes were >90%.

2. Isolating of RNA and Comparative Analysis

Extraction was performed using the mirVana kit (Ambion, Grand Island, N.Y.). After extraction, the RNA samples were checked for purify and quality via an Agilent Bioanalyzer before being submitted for human miRNA array (Sanger miRBase v15, 1,087 human miRNAs) analysis and whole genome microarray analysis (30,275 human genes) provided by the Phalanx Biotech Group (Belmont, Calif.). The results of the analysis were used to determine which miRNAs had significant "fold" differences in expression of: 1) glioblastoma relative to normal brain; 2) glioblastoma-infiltrating macrophages relative to patient matched monocytes; 3) glioblastoma-infiltrating macrophages relative to normal donor monocytes; and 4) glioblastoma monocytes relative to normal donor monocytes, calculated using Microsoft Excel. The miRNAs with the most significant differences in expression levels were then chosen for the miRNA target analysis using multiple bioinformatics prediction tools, including TargetScan 6.2, PicTar, miRanda, and miRDB.

3. Monocyte M1 Versus M2 Differentiation

The M1/M2 in vitro induction protocol was adapted from previous reports (Krausgruber et al., 2011; Sierra-Filardi et al., 2011). Briefly, M1 and M2 macrophages were obtained after 5 days of culture of human CD14+ monocytes in RPMI-1640 medium with L-glutamine (Corning Cellgro, Manassas, Va.) supplemented with 10% heat-inactivated FBS (Sigma-Aldrich) and GM-CSF (50 ng/ml for M1) or M-CSF (100 ng/ml for M2; Peprotech, Rocky Hill, N.J.). Phenotypic markers of MHCII, CD11b, CD14, CD45, CD68, CD80, CD86, CD163 and CD206 were confirmed by FACS analysis.

4. Real-Time PCR to Confirm Relative miR-142 Expression Levels

Total RNA extracted from monocytes was used as the template for reverse transcription using the TaqMan real-time PCR kit (Applied Biosystems, Carlsbad, Calif.) in the 7500 real-time PCR system (Applied Biosystems). Primers for reverse transcription were purchased for human miR-142-3p and U18 (Applied Biosystems). U18 was used as an endogenous control and cDNA was used as the template for real-time PCR. Further reactions, substituting water for the cDNA template, were used as additional controls. U18 and miR-142-3p amplifications were run in triplicate. Microsoft Excel was used to calculate the mean levels of each miR and the U18 internal control. The relative expression levels of miR-142-3p were compared with those of the internal controls, and bar graphs were generated.

5. Luciferase Assay

To determine whether miR-142-3p can bind to TGFβR1 3'-UTR, lipofectamine 2000 transfection reagent (Invitrogen, Grand Island, N.Y.) was used to co-transfect HeLa reporter cells with the TGFβR1 3' UTR-luciferase reporter plasmid (pMirTarget, Origene, Rockville, Md.) and the miR-142-3p expression plasmid (or the scramble control plasmid; GeneCopoeia, Rockvile, Md.). The luciferase assay was performed using the Dual-Luciferase® reporter assay system (E1910, Promega, Madison, Wis.) and the firefly luciferase activity was normalized to *renilla luciferase* activity. The interaction between miR-142-3p and its target were measured by comparing the results of the co-transfection of the TGFβR13' UTR-luciferase reporter and the miR-142-3p plasmids with those of the 3' UTR-luciferase reporter plasmid and the scramble control plasmid.

6. Transfection of miR-142-3p Precursor/Inhibitor into Monocytes

The miR-142-3p precursor, inhibitor, and matching negative controls were purchased from Ambion. Lipofectamine 2000 transfection reagent (Invitrogen) was used for the transfection of human CD14+ monocytes according to the manufacturer's instructions. Briefly, $10^6$ freshly MACS-sorted human CD14+ monocytes were incubated in a 12-well plate containing 800 µL of either M1 or M2 differentiation medium without antibiotics for 2 hours. The miRNA precursor/inhibitor/matching control (100 pmol) and 2 µL of lipofectamine 2000 reagent in 198 µL Opti-MEM I medium were mixed gently and then incubated for 20 min at room temperature. The final concentration of miRNA was 100 nM, and the transfection efficiency was confirmed by qRT-PCR.

7. Macrophage Apoptosis Assay

After the transfection of the miR-142-3p precursor and matching negative controls with lipofectamine 2000 transfection reagent, CD14+ monocytes were cultured in either the M1 or M2 differentiation medium. After 24 h and 48 h, the cells were harvested and labeled with Annexin V-PE and 7-amino-actinomycin D according to the manufacturer's instructions (BD Pharmingen, San Diego, Calif.). The total cell apoptosis was analyzed by flow cytometry within 1 hour. To ascertain the relationship between TGFβR1 blockade and apoptosis, untransfected M1 or M2-committed monocytes were incubated with titrated concentrations of two TGFβR1 inhibitors, SB431542 (Chen et al., 2008) and LY-364947 (Hardee et al., 2012) (EMD Millipore; Billerica, Mass.) for 48 hours. SB431542 is a specific inhibitor of the TGF-β superfamily type I activin receptor-like kinase receptors ALK4, ALK5 and ALK7 (Inman et al., 2002) whereas LY-364947 has been shown to have cross reactivity with VEGF (Vogt et al., 2011). Moreover, M1 or M2-committed monocytes were also transfected with two different TGFβR1 siRNAs (set #1 sense: GGCAUCAAAAUGUAAUUCUtt (SEQ ID NO:8), antisense: AGAAUUACAUUUUGAUGC-Ctt (SEQ ID NO:9), final concentration: 100 nM; set #2 sense: CCAUUGAUAUUGCUCCAAAtt (SEQ ID NO:10), antisense: UUUGGAGCAAUAUCAAUGGta (SEQ ID NO:11), final concentration: 5 nM) with matched controls (Ambion) by Lipofectamine 2000 transfection reagent (Invitrogen). The knockdown efficiency of TGFBR1 mRNA was confirmed by qRT-PCR.

8. In Vivo Experiments

The miR-142-3p duplex that mimics pre-miR-142-3p (sense: 5'-UGUAGUGUUUCCUACUUUAUGGAU-3' (SEQ ID NO:12), antisense: 5'-CCAUAAAGUAG-GAAACACUACAAA-3' (SEQ ID NO:13)) and the scramble control miRNA duplex (sense: 5'-AGUACUGC-UUACGAUACGGTT-3' (SEQ ID NO:14), antisense: 5'-CCGUAUCGUAAGCAGUACUTT-3' (SEQ ID NO:15)) were synthesized (Avetra Bioscience, San Carlos, Calif.). The sequence of murine miR-142-3p is identical to human miR-142-3p on the basis of NCBI blast data. The treatment cohorts consisted of 20 µg of the miR-142-3p or scramble control in 48 µL of phosphate-buffered saline (PBS) mixed with the vehicle (40 µL PBS containing 10 µL lipofectamine 2000) or the vehicle control (90 µL PBS+10 µL lifofectamine 2000). Mice were maintained in the M.D. Anderson Isolation Facility in accordance with Laboratory Animal Resources Commission standards and handled according to the approved protocol 08-06-11831.

9. Syngeneic Subcutaneous Model

The murine glioma GL261 cell line was obtained from the National Cancer Institute-Frederick Cancer Research Tumor Repository. These cells were cultured in a humidified atmosphere of 5% $CO_2$ and 95% air at 37° C. in Dulbecco's Modified Eagle's medium (Life Technologies; Grand Island, N.Y.) supplemented with 10% fetal bovine serum and 1% penicillin/streptomycin/L-glutamine (Mediatech, Manassas, Va.). The GL261 glioma cell cultures were passaged every 3 days to ensure logarithmic growth. To induce subcutaneous tumors, logarithmically growing GL261 cells were injected into the right hind flanks of 6-week-old C57BL/6J female mice or nude mice at a dose of $1 \times 10^6$ cells suspended in 100 µL of matrigel basement membrane matrix (BD Biosciences, San Jose, Calif.). When palpable tumors formed that were approximately 0.5 cm in diameter, the mice (n=5/group) were treated by either local tumor injection or intravenous administration. Tumors were measured twice per week. Mice that showed signs of morbidity, high tumor burden, or skin necrosis were immediately euthanized according to M.D. Anderson guidelines. Tumor volume was calculated with slide calipers using the following formula: V=(L×W×H)/2, where V is volume (mm$^3$), L is the long diameter, W is the short diameter, and H is the height.

10. Syngeneic Intracranial Clonotypic Glioma Model

To induce intracerebral tumors in C57BL/6J mice, GL261 cells were collected in logarithmic growth phase, washed twice with PBS, mixed with an equal volume of 10% methyl cellulose in improved modified Eagle's medium (zinc option; Life Technologies, Inc., Gaithersburg, Md.), and loaded into a 250-μl syringe (Hamilton, Reno, Nev.) with an attached 25-gauge needle. The mice were anesthetized with ketamine (100 mg/kg) and xylazine (10 mg/kg), and the needle was positioned 2 mm to the right of bregma and 4 mm below the surface of the skull at the coronal suture using a stereotactic frame (Kopf Instruments, Tujunga, Calif.), as previously described (Heimberger et al., 2003). The intracerebral tumorigenic dose for GL261 cells was 5×10$^4$ in a total volume of 5 μl. Mice were then randomly assigned to scramble control (n=6) or the miR-142-3p treatment group (n=7) Animals were observed and weighted three times per week, and when they showed signs of neurological deficit (lethargy, failure to ambulate, lack of feeding, or loss of >20% body weight), they were compassionately euthanized. These symptoms typically occurred within 48 hours of death. Their brains were removed and placed in 4% paraformaldehyde and embedded in paraffin. The intracerebral tumorigenic dose for GL261 cells was 5×104 in a total volume of 5 μl. Mice were randomly assigned to scramble control or the miR-142-3p treatment group Animals were observed and weighed three times per week, and when they showed signs of neurological symptoms, they were compassionately euthanized. Their brains were removed, placed in 4% paraformaldehyde and embedded in paraffin.

11. Genetically Engineered Murine Models

Vector constructs. RCAS-PDGFB generation has been previously described (Dai et al., 2001). DF-1 immortalized chicken fibroblasts were grown in Dulbecco's modified Eagle's medium with 10% fetal bovine serum in a humidified atmosphere of 95% air/5% CO2 at 37° C. Live virus was produced by transfecting plasmid versions of RCAS vectors into DF-1 cells using FuGene6. These cells were replicated in culture.

In vivo Somatic Cell Transfer in Transgenic Mice. The transgenic Ntv-a mice are mixtures of different strains, including C57BL/6, BALB/c, FVB/N, and CD1. To transfer genes via RCAS vectors, DF-1 producer cells transfected with a particular RCAS vector (1×10$^5$ DF-1 cells in 1-2 μl of PBS) were injected into the frontal lobes of Ntv-a mice at the coronal suture of the skull using a Hamilton Gastight syringe. The mice were injected on postnatal days 1 or 2, when the number of Nestin+ cells producing TVA is the highest. The mice were killed 90 days after injection or sooner if they demonstrated morbidity related to tumor burden. Their brains were removed and analyzed for tumor formation.

Animal Randomization. Twenty-one days after introducing the glioma-inducing transgenes RCAS-PDGFB and RCAS-BCL2, littermates were randomly assigned to the treatment or control group (n=9/group). Mice were treated intravenously on Monday, Wednesday, and Friday for 3 weeks.

12. Immunohistochemistry

Formalin-fixed, paraffin-embedded 4 μm sections of the glioma were first deparaffinized in xylene and rehydrated in ethanol. Endogenous peroxidase was blocked with 0.3% hydrogen peroxide/methanol for 10 min at room temperature. Then, the ThermoScientific PTModule (Thermo Fisher Scientific, Fremont, Calif.) with citrate buffer (pH 6.0) was used for antigen retrieval. Immunohistochemical staining was performed using the Lab Vision Immunohistochemical Autostainer 360 (Thermo Fisher Scientific, Fremont, Calif.). The staining was visualized using an avidin-biotin complex technique with diaminobenzidine (Invitrogen, Carlsbad, Calif.) as the chromogenic substrate and hematoxylin as the counterstain. To detect expression of the macrophage-restricted cell surface glycoprotein F4/80, a purified anti-mouse F4/80 (1:50; Biolegend, San Diego, Calif.) antibody was used. Two independent observers (L-YK, X-Y L) quantitatively evaluated F4/80 expression by analyzing the tumors using high-power fields (max: ×40 objective and ×10 eyepiece) of each specimen. The observers were blinded to the treatment cohorts and the analysis was secondarily reviewed again by the neuropathologist (GNF). The correlation between miR-142-3p treated mice survival and corresponding F4/80 positive cell percentages was fitted with linear regression using GraphPad Prism (La Jolla, Calif.).

13. Isolation of Human Glioblastoma-Infiltrating Macrophages and CD14+ Monocytes Informed consent was obtained from each subject. Tumors were confirmed as glioblastoma (World Health Organization grade IV) by a board-certified neuropathologist. Tumor tissue was washed in RPMI medium, broken down into smaller pieces and digested for 2 hours using a cancer cell isolation kit (Panomics, Santa Clara, Calif.). The technique for isolating central nervous system macrophages based on CD11b expression and Percoll gradient centrifugation in mice (Stupp et al., 2005; miR-142 manu) was adapted for isolating human glioblastoma infiltrating macrophages by our group (Hussain et al., 2006) and consisted of CD11b+MACS positive selection after Percoll gradient centrifugation to achieve over 95% purity. These purified glioblastoma-infiltrating macrophages express CD14 (Hussain et al., 2006). Matched peripheral monocytes and monocytes from the healthy donors were obtained with anti-CD14 [a general marker of monocytes and monocyte-derived macrophages (Wu et al., 2010)] microbead magnetic cell sorting, according to the manufacturer's instructions (Miltenyi Biotec, Cambridge, Mass.). CD14+ monocytes have previously been shown to be induced to the M2 phenotype, similar to glioblastoma-infiltrating macrophages, by supernatants from glioblastoma cancer stem cells (Gabriely et al., 2008).

14. Isolating of RNA and Comparative Analysis

After extraction using the mirVana kit (Ambion, Grand Island, N.Y.), the RNA samples from infiltrating macrophages, peripheral monocytes and total glioblastoma specimens were checked for purify and quality via an Agilent Bioanalyzer before being submitted for human miRNA array (Sanger miRBase v15, 1,087 human miRNAs) analysis and whole genome microarray analysis (30,275 human genes) provided by the Phalanx Biotech Group (Belmont, Calif.). This microarray data has been submitted to the NCBI GEO database (assession number is GSE51332). Total RNA from normal brain tissues was obtained from Biochain (Hayward, Calif.). The results of the analysis were used to determine which miRNAs had significant "fold" differences in expression of: 1) glioblastoma relative to normal brain; 2) glioblastoma-infiltrating macrophages relative to patient matched monocytes; 3) glioblastoma-infiltrating macrophages relative to normal donor monocytes; and 4) glioblastoma monocytes relative to normal donor monocytes, calculated using Microsoft Excel. The miRNAs with the most significant differences in expression levels were then chosen for the miRNA target analysis using multiple bioinformatics prediction tools, including TargetScan 6.2, PicTar, miRanda, and miRDB.

15. Human gCSCs gCSCs were cultured in Dulbecco's modified Eagle's medium F-12 containing 20 ng/ml of epidermal growth factor, basic fibroblast growth factor (both from Sigma, St. Louis, Mo.), and B27 (1:50; Invitrogen, Carlsbad, Calif.) as a neural stem cell-permissive medium (neurosphere medium) and passaged every 5-7 days. The characteristics of these cells, including the cytogenetics, limiting dilution assays, tumorigenicity, CD133 expression, and immune-suppressive properties have been previously published (Gabriely et al., 2008; Iliopoulos et al., 2010).

16. Monocyte to M1 Versus M2 Macrophage Differentiation

The M1/M2 in vitro induction protocol was adapted from previous reports (Wang et al., 2012; Hui et al., 2010). Briefly, M1 and M2 macrophages were obtained after 5 days of culture of human CD14+ monocytes in RPMI-1640 medium with L-glutamine (Corning Cellgro, Manassas, Va.) supplemented with 10% heat-inactivated FBS (Sigma-Aldrich) and GM-CSF (50 ng/ml for M1) or M-CSF (100 ng/ml for M2; Peprotech, Rocky Hill, N.J.). Phenotypic markers of immune status (MHC, CD45, CD80 and CD86) monocyte-macrophage lineage (CD14), macrophage (CD11b, CD68), and M2 differentiation (CD163) were confirmed by FACS analysis.

17. Phagocytotic Assay

The phagocytic activity of the M1/M2 macrophages was determined by measuring the uptake of fluorescent pHrodo Red E. coli bioparticles (Life Technologies, Carlsbad, Calif.). Briefly, the fluorescent bioparticles were resuspended in uptake buffer at a concentration of 1 mg/ml and sonicated to homogeneously disperse the particles. Then the medium of pre-seeded M1/M2 macrophages in 96-well plates (105 cells per well) was removed and replaced with the bioparticle suspension. After 2 hours of incubation at 37° C., the fluorescence intensity was measured by a fluorescence plate reader (BMG LabTech GmbH, Ortenberg, Germany) at 580 nm. The net phagocytosis is calculated by subtracting the appropriate negative/blank control fluorescent intensity from the experimental wells.

18. Western Blot

M1 and M2 macrophages were harvested on day 5 after transfection with pre-miR-142-3p and then lysed in RIPA cell lysis buffer supplemented with a protease inhibitor cocktail (P8340, Sigma-Aldrich) and a phosphatase inhibitor (P5726, Sigma-Aldrich). Protein concentration was determined with the BCA protein assay kit (Pierce). Twenty micrograms of protein of each sample were separated by 4-15% sodium dodecyl sulfate (SDS)-polyacrylamide gels (Bio-Rad) and electro-transferred to nitrocellulose membranes, and subjected to immunoblot analysis with antibodies to ITGB8 (1:500, Sigma-Aldrich), α-Tubulin (1:2000, Sigma-Aldrich), ITGAV (1:500, Santa Cruz, Dallas, Tex.), TGFβ2 (1:1000, Santa Cruz), SMAD4 (1:1000, Santa Cruz), TGFβR1 (1:1000, Santa Cruz), NF-κB (1:1000, Cell Signaling, Danvers, Mass.), β-Actin (1:1000, Cell Signaling), p-SMAD2/3 (1:1000, Cell Signaling), p-Akt (1:1000, Cell Signaling), p-TAK1 (1:1000, Cell Signaling) and RhoA (1:1000 Cell Signaling). Autoradiography of the membranes was performed using Amersham ECL Western-blotting detection reagents (Amersham Biosciences, Piscataway, N.J.).

19. ELISA

Supernatant medium conditioned by macrophages transfected with miR-142-3p or scramble control was measured for TGF-β2 using ELISAs (DuoSet ELISA kits, R&D Systems). The supernatants were collected after 48 hours and 5 days in culture and stored at −20° C. Before qualification, the supernatants were pre-treated with 1N HCl to activate the immunoreactive form, and then added in triplicate to appropriate capture antibody-coated plates. After the plates were washed, horseradish peroxidase-conjugated detection antibody was added. The substrate used for color development was tetramethylbenzidine. The optical density was measured at 450 nm with a microplate reader (Spectra Max 190; Molecular Devices, Sunnyvale, Calif.) and cytokine concentrations were quantified with SoftMax Pro software (Molecular Devices).

20. Luciferase Assay

To determine whether miR-142-3p can bind to TGFBR1 3'-UTR, the lipofectamine 2000 transfection reagent (Invitrogen, Grand Island, N.Y.) was used to co-transfect HeLa cells with the TGFBR1 3' UTR-luciferase reporter plasmid (BlueHeron, Bothell, Wash.), pRL-TK renilla luciferase plasmid (Promega, Madison, Wis.), and the miR-142-3p precursor. The luciferase assay was performed using the Dual-Luciferase® reporter assay system (Promega, Madison, Wis.) and the firefly luciferase activity was normalized to renilla luciferase activity. The interaction between miR-142-3p and its target were measured by comparing the firefly luciferase activity in the presence or absence of miR-142-3p which was normalized by the renilla luciferase activity.

21. Macrophage Apoptosis Assay

After the transfection, CD14+ monocytes were cultured in either the M1 or M2 differentiation medium. After 48 hours, the cells were harvested and labeled with Annexin V-PE and 7-amino-actinomycin D according to the manufacturer's instructions (BD Pharmingen, San Diego, Calif.). The total cell apoptosis was analyzed by flow cytometry within 1 hour. To ascertain the relationship between TGFBR1 blockade and apoptosis, untransfected M1 or M2-committed macrophages were incubated with titrated concentrations of two TGFBR1 inhibitors, SB431542 (Chan et al., 2011; Wu et al., 2012) and LY-364947 (Inoue et al., 2012; Namlos et al., 2012) (EMD Millipore, Billerica, Mass.) for 48 hours. M1 or M2-committed macrophages were transfected with two different TGFBR1 siRNAs (set #1 sense: GGCAU-CAAAAUGUAAUUCUtt (SEQ ID NO:16), antisense: AGAAUUACAUUUUGAUGCCtt (SEQ ID NO:17), final concentration: 100 nM; set #2 sense: CCAUUGAUAUUG-CUCCAAAtt (SEQ ID NO:18), antisense: UUUGGAG-CAAUAUCAAUGGta (SEQ ID NO:19), final concentration: 5 nM) with matched controls (Ambion). The knockdown efficiency of TGFBR1 mRNA was confirmed by qRT-PCR.

22. Pharmacokinetic Study

Non-tumor bearing C57BL/6J mice (n=3 per time point) were administered miR+ lipofectamine 2000 i.v. once and subsequently terminated at 0, 15 minutes, 1, 4, 8 and 24 hours. The liver, peripheral blood mononuclear cells and serum were subsequently analyzed for miR expression by quantitative PCR. A noncompartmental analysis was performed using industry standard software (WinNonLin 6.3, Pharsight) to estimate the pharmacokinetic parameters for each individual animal. The following parameters were estimated for each animal: apparent elimination half-life (T1/2, calculated as ln(2)/lambdaz, lambdaz being the first order rate constant associated with the terminal portion of the time-concentration curve as estimated by linear regression of time vs. log concentration), area under the time-concentration curve from time zero to the last observed concentration (AUC0-obs, calculated by the linear trapezoidal rule), and area under the time-concentration curve from time zero extrapolated to infinity (AUC0-inf, calculated by adding the last observed concentration divided by lambda z to the AUC0-obs). Mean parameters were then calculated from individual animal estimates.

23. Ex Vivo Immune Functional Analysis

GL261 tumor-bearing mice were treated with miR-142-3p or scramble control as previously described. After 3 days, the blood, lymph nodes and spleens were harvested and single cell suspensions were obtained. For M1 and M2 marker analysis, the cells were surface stained with CD11b, permeabilized with Cytofix/Cytoperm (BD Pharmingen), and then stained with FITC conjugated anti-IL-6, anti-IFN-γ or anti-TNF-α (BD Pharmingen). Control isotype antibodies were used to establish gating and were analyzed using FlowJo software (TreeStar). For analysis of CD8+ T-cell effector function, GL261 tumor-bearing mice were treated for two weeks, and CD8+ T cells were purified from the splenocytes by negative selection using CD8+ T cell enrichment microbeads (BD Biosciences). For intracellular cytokine staining, the T-cells were stimulated for 6 hours in the presence of 50 ng/ml phorbol myristate acetate (PMA), 500 ng/ml ionomycin (Sigma-Aldrich), and 2 μM monensin (GolgiStop, BD Sciences), permeabilized, and then stained using either PE-conjugated IFN-γ antibody, IL-2, or TNF-α (BD Pharmingen). For ex vivo cytotoxicity assay, the ratios of CD8 T-cells to 2 μM CSFE-labeled GL261 target cells were 1:1, 5:1, 10:1 and 20:1. Viability of CFSE-labeled GL261 cells was assessed using propidium iodide staining and a FACS Calibur flow cytometer (BD Biosciences).

24. Mature Dendritic Cell Analysis

Single cell suspensions were prepared from the spleens of miR-142-3p or scramble control treated GL261 tumor-bearing mice. Splenocytes were stained with the PE-labeled anti-mouse dendritic cell marker (33D1) and the APC-labeled anti-MHCII (I-A/I-E) (eBioscience) and acquired on a FACS Calibur (Becton Dickinson) to determine the percentage of 33D1+MHCII+ mature dendritic cells.

25. Statistical Analysis

Linear mixed models were fit to assess tumor growth after adjusting for treatment effect and taking into account the associations among repeated measures within each subject. Kaplan-Meier curves were used to estimate overall survival (OS) distributions. Log rank tests were used to compare OS between groups. All computations were carried out in SAS version 9.3 (SAS Institute, Cary, N.C.) and TIBCO Spotfire S+ version 8.2 (Somerville, Mass.).

Figure 14A:
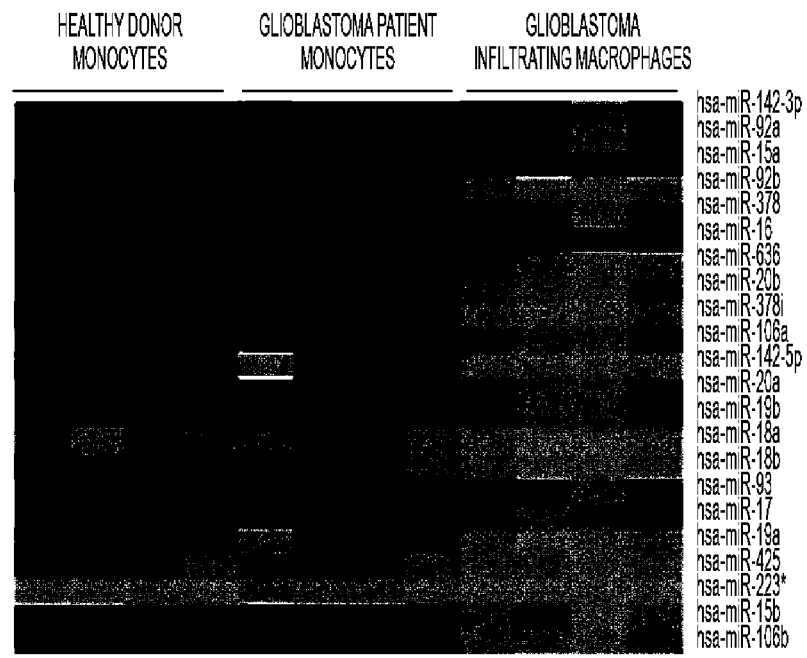
FIGS. 14A-B. miR-142-3p Expression in Gliomas.
Figure 14B:
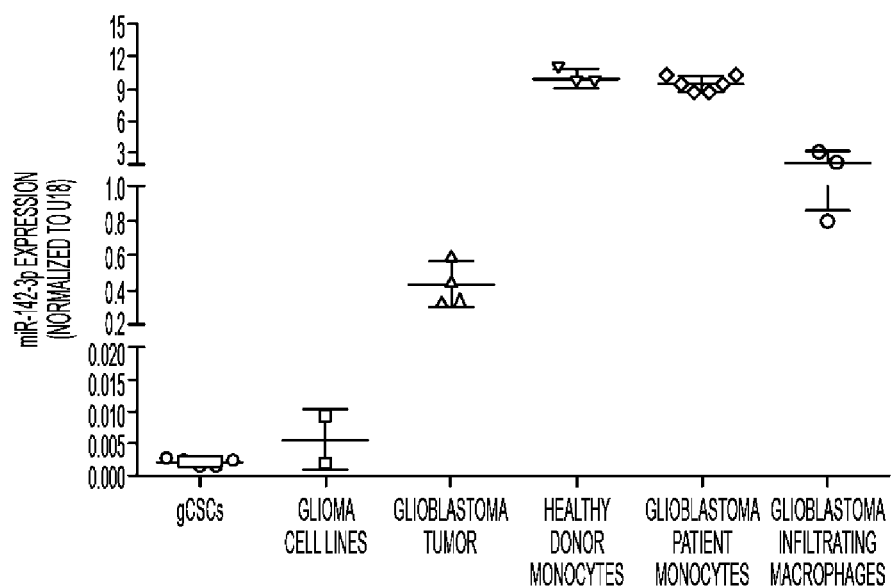

B. Results 1. miR-142-3p Expression is Down-Modulated in Monocyte-Derived Glioblastoma-Associated Macrophages Although monocyte-derived glioblastoma-infiltrating macrophages have been well investigated for their immune suppressive properties, the relationship of this most abundant immune cell population within the glioblastoma microenvironment to miRNA dysregulation has not been evaluated to date. Utilizing the Human miRNA OneArray Microarray v2 to assess miRNA expression profiling, the miRNA expression profile in glioblastoma-infiltrating macrophages was matched to that of monocytes from the peripheral blood, and significantly modulated miRNAs were identified. With a mean 4.9-fold decrease relative to the level in matched peripheral monocytes, miR-142-3p emerged as a leading candidate (FIG. 14A and Table 5). On a microarray study of total miRNA, down regulation of miR-142-3p down-regulation wasn't observed in glioblastoma tissue relative to normal brain tissue (Table 6). This may be explained by the subsequent quantitative RT-PCR analysis, which revealed that despite the fact that miR-142-3p expression is detected in total glioblastoma tumor tissues, glioblastoma cell lines (such as U-87 MG and U251) or glioma cancer stem cells (gCSCs) seldom express this miRNA. On the contrary, non-tumor cells such as monocytes are the main source of miR-142-3p, but the miR-142-3p is down regulated within the glioblastoma-infiltrating macrophages relative to peripheral blood monocytes (FIG. 14B). Of note, there was no significant difference of miR-142-3p expression in peripheral monocytes from patients with glioblastoma compared to healthy donors.

TABLE 5 miRNA expression in glioblastoma-infiltrating macrophages relative to that in peripheral blood monocytes

| miRNA | Relative down regulation | miRNA | Relative up regulation |
|---|---|---|---|
| hsa-miR-142-3p | 5.0 | hsa-miR-4792 | 8.6 |
| hsa-miR-92a | 4.9 | hsa-miR-574-5p | 6.4 |
| hsa-miR-15a | 4.4 | hsa-miR-34a | 6.4 |
| hsa-miR-92b | 3.8 | hsa-miR-4290 | 6.0 |
| hsa-miR-378 | 3.8 | hsa-miR-3149 | 5.7 |
| hsa-miR-16 | 3.7 | hsa-miR-4455 | 5.6 |
| hsa-miR-636 | 3.7 | hsa-miR-32* | 5.6 |
| hsa-miR-20b | 3.6 | hsa-miR-1273f | 4.7 |
| hsa-miR-378i | 3.6 | hsa-miR-4634 | 4.6 |
| hsa-miR-106a | 3.6 | hsa-miR-3653 | 4.1 |
| hsa-miR-142-5p | 3.6 | hsa-miR-634 | 4.1 |
| hsa-miR-20a | 3.5 | hsa-miR-2116* | 3.9 |
| hsa-miR-19b | 3.4 | hsa-miR-4323 | 3.9 |
| hsa-miR-18a | 3.3 | hsa-miR-1273e | 3.8 |
| hsa-miR-18b | 3.3 | hsa-miR-532-3p | 3.7 |
| hsa-miR-93 | 3.3 | hsa-miR-4508 | 3.6 |
| hsa-miR-17 | 3.3 | hsa-miR-92b* | 3.4 |
| hsa-miR-19a | 3.3 | hsa-miR-4713-5p | 3.3 |
| hsa-miR-425 | 3.3 | hsa-miR-30c-1* | 3.3 |
| hsa-miR-223* | 3.2 | "hsa-miR-4492/4508" | 3.3 |

TABLE 6

Expression of miRNAs in glioblastoma relative to normal brain

| miRNA | Relative down regulation | miRNA | Relative up regulation |
|---|---|---|---|
| hsa-miR-124 | 24.6 | hsa-miR-1273 | 3.7 |
| hsa-miR-3172 | 13.8 | hsa-miR-559 | 3.6 |
| hsa-miR-138 | 13.4 | hsa-miR-4286 | 3.2 |
| hsa-miR-3196 | 8.5 | hsa-miR-3152 | 3.1 |
| let-7b | 7.3 | hsa-miR-766 | 3 |
| let-7e | 6.9 | hsa-miR-542-3p | 2.7 |
| hsa-miR-1826 | 5.9 | hsa-miR-1302 | 2.7 |
| hsa-miR-1228* | 5.8 | hsa-miR-2355 | 2.7 |
| hsa-miR-4284 | 5.6 | hsa-miR-1285 | 2.6 |
| let-7d | 5.6 | hsa-miR-548c-5p | 2.5 |
| hsa-miR-3162 | 5.4 | hsa-miR-1281 | 2.3 |
| hsa-miR-874 | 5.2 | hsa-miR-1248 | 2.2 |
| let-7c | 5.2 | hsa-miR-1272 | 2.1 |
| hsa-miR-103 | 5 | hsa-miR-488* | 2.1 |
| hsa-miR-128 | 4.9 | hsa-miR-3192 | 2.1 |

TABLE 6-continued

Expression of miRNAs in glioblastoma relative to normal brain

| miRNA | Relative down regulation | miRNA | Relative up regulation |
|---|---|---|---|
| let-7a | 4.7 | hsa-miR-548d-5p | 2.1 |
| hsa-miR-26a | 4.5 | hsa-miR-3197 | 2.1 |
| hsa-miR-762 | 4.5 | hsa-miR-4323 | 2.1 |
| hsa-miR-7 | 4.2 | hsa-miR-3146 | 2 |
| hsa-miR-142-3p | 1.2 | | |

2. miR-142-3p Expression in M1 vs. M2 Macrophages

Glioblastomas actively recruit macrophages to the tumor site and induce them to adopt a tumor-supportive M2 phenotype capable of mediating immunosuppression and promoting invasion (Wu et al., 2010). Based on the observation of miR-142-3p down-regulation in glioblastoma-infiltrating macrophages, the miR-142-3p expression in the proinflammatory M1 subset and immunosuppressive M2 subsets were clarified. Peripheral human CD14+ monocytes from healthy donors were isolated and incubated them in complete RPMI medium supplemented with recombinant human GM-CSF or M-CSF to induce M1 and M2 macrophages, respectively. After 5 days of in vitro induction, the two subsets were obtained and verified based on their morphological, phenotypic, and phagocytic characteristics. Specifically, the M1 macrophages appeared more round, whereas the M2 macrophages assumed a more elongated phenotype as previously described (FIG. 15A) (Hashimoto et al., 1999). Moreover, the M2 macrophages expressed lower levels of CD11b, CD86, and MHC II than the M1 macrophages but had higher levels of CD163 (FIG. 15B) and exhibited more dynamic phagocytosis (P<0.001, n=6, FIG. 15C), consistent with prior reports (Chihara et al., 2012; Heusinkveld et al., 2011). The down-regulation of miR-142-3p during monocyte to macrophage differentiation was confirmed by qRT-PCR assay; however, this alteration was more profound in the immune suppressive M2 macrophages (p<0.05, FIG. 15D).

3. miR-142-3p Interacts with the TGF-β Pathway

Figure 20A:
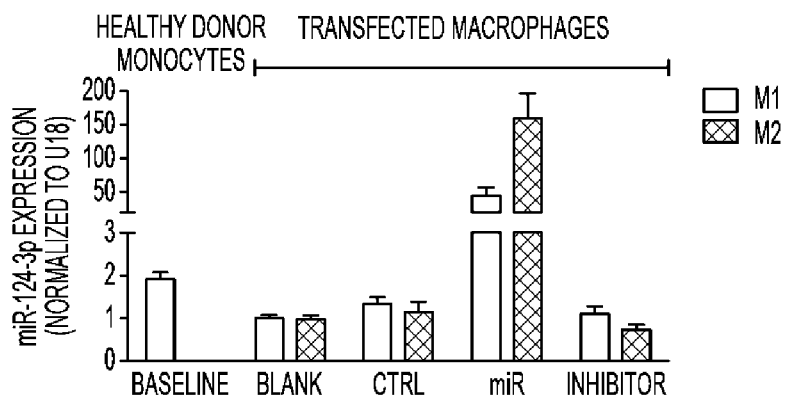
FIGS. 20A-C.
Figure 20B:
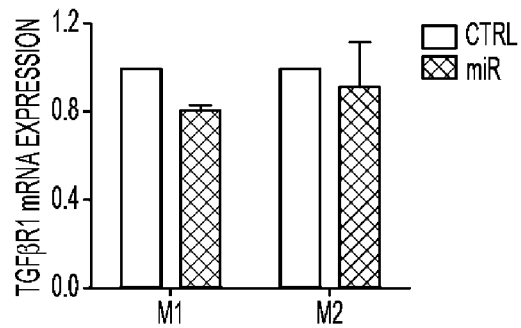
Figure 20C:
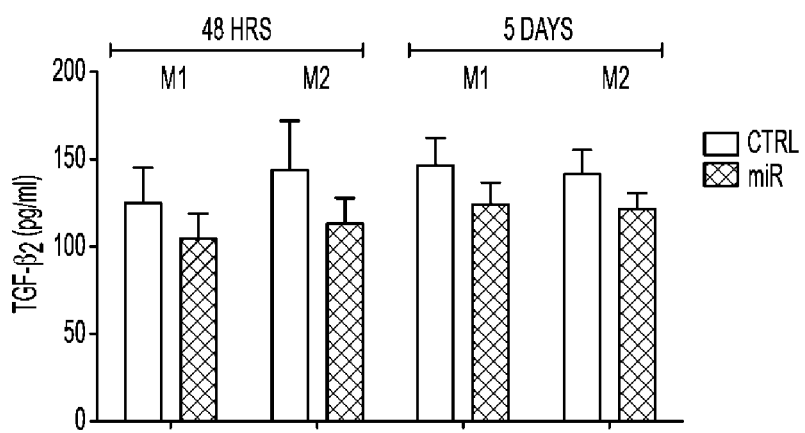

Multiple bioinformatics tools (TargetScan 6.2, PicTar, miRanda and miRDB) were used to identify potential target genes of miR-142-3p. A cluster of TGF-β pathway genes with conserved target sites in their 3'-UTRs were identified, including TGFB2/3, TGFBR1, and TAB2. The TGF-β pathway is well known for its potent role in immunosuppression and tumorigenesis including polarization of tumor-promoting M2 macrophages (Flavell et al., 2010). Thus, the effect of miR-142-3p on the expression of the TGF-β pathway in the monocyte-derived M1 and M2 subsets was investigated. After transfection with miR-142-3p, the human CD14+ monocytes were polarized to the M1 and M2 subsets using standard ex vivo culture techniques described above. The miR-142-3p overexpression was confirmed compared to blank and scramble control transfected cells using qRT-PCR (FIG. 20A). In the miR-142-3p-overexpressing cells, the mRNA level of TGFβR1 mRNA remained unchanged (FIG. 20B); whereas the TGFβR1 protein levels were repressed in the M2 macrophages as shown by Western blot (FIG. 16A) indicating that miR-142-3p mediates its effect on the TGFβR1 pathway by post-transcriptional regulation rather than by targeting mRNA degradation. TGF-β2 cytokine secretion was not inhibited by miR-142-3p in either the M1 or M2 macrophages (FIG. 20A-B). Furthermore, anti-miR-142-3p treatment resulted in slightly increased TGFβR1 protein levels in the M2 macrophages (FIG. 16A) signifying that miR-142-3p TGF-β pathway regulation is contextual and cell specific. Other predicted targets of miR-142-3p such as ITGB8, ITGAV, and TGFβ2 were not found to be inhibited in either the M1 or M2 macrophage populations (FIG. 16A). Furthermore, we detected the activation of the TGFBR1 downstream protein, SMAD2, after stimulation of M1 and M2 cells with TGFβ1. As expected, p-SMAD2 was inhibited by miR-142-3p only in M2 macrophages but not in the M1 macrophages after stimulation with TGFβ-1 (FIG. 16B). TGFBR1 SMAD-independent targets such as p-AKT and RhoA were not appreciably altered by miR-142-3p. p-TAK1 was not observed to be expressed in either M1 or M2 populations.

4. TGF-b Stimulus Assay-Smad2/3/4-pSmad2/3/4 Pending

To further prove that miR-142-3p binds to TGFβR1, a luciferase expression assay was conducted, including mutating the predicted miR-142-3pTGFβR13'-UTR binding site (FIG. 16B). In co-transfected HeLa cells, TGFβR1 luciferase activity was significantly inhibited by miR-142-3p, whereas directed mutational alteration of the miR-142-3p TGFβR13'-UTR binding site resulted in partial abolishment of luciferase activity (FIG. 16C). However, in co-transfected M2 cells, directed mutational alteration of the miR-142-3p TGFβR13'-UTR binding site resulted in complete abolishment of luciferase activity (FIG. 16D) emphasizing that TGFβR1 is under the regulation of miR-142-3p in M2 macrophages.

Figure 21A:
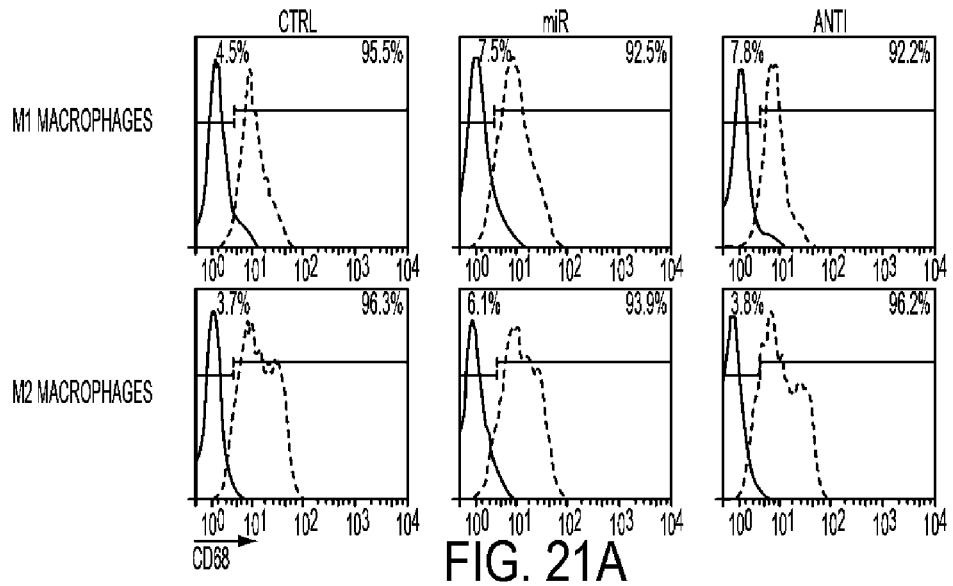
FIGS. 21A-C.
Figure 21B:
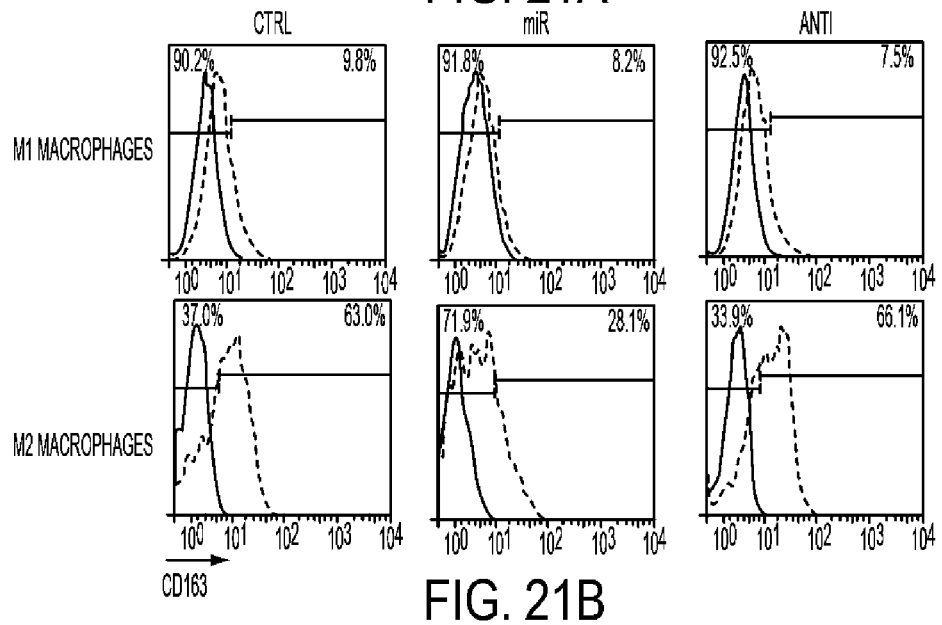
Figure 21C:
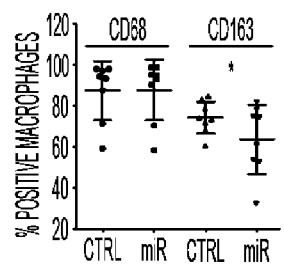

5. Overexpression of miR-142-3p Minimally Induces a Phenotypic Shift from M2 to M1 Macrophages The miR-142-3p overexpression alters the monocyte-derived macrophage phenotype and function was assessed next. CD68, a general macrophage marker, and CD163, a M2 specific marker (Jensen et al., 2009; Pander et al., 2011; Puig-Kroger et al., 2009), were selected to evaluate the phenotypic shift. After the miR-142-3p or inhibitor transfection, CD68 levels of both the M1 and M2 macrophages were unchanged (ctrl: 87.8±5.1% versus miR: 87.8±5.1%, P=0.9987, n=8, FIGS. 21A and 21C), suggesting that miR-142-3p doesn't influence monocyte to macrophage differentiation. Although inconsistently observed, CD163 expression was down-regulated upon the overexpression of miR-142-3p, indicating this miR can modestly modulate the M1/M2 shift and push macrophage differentiation to the pro-inflammatory M1 subset (ctrl: 74.6±2.8% versus miR: 63.9±6.0%, P=0.02, n=8, FIGS. 22B and 22C).

Figure 17A:
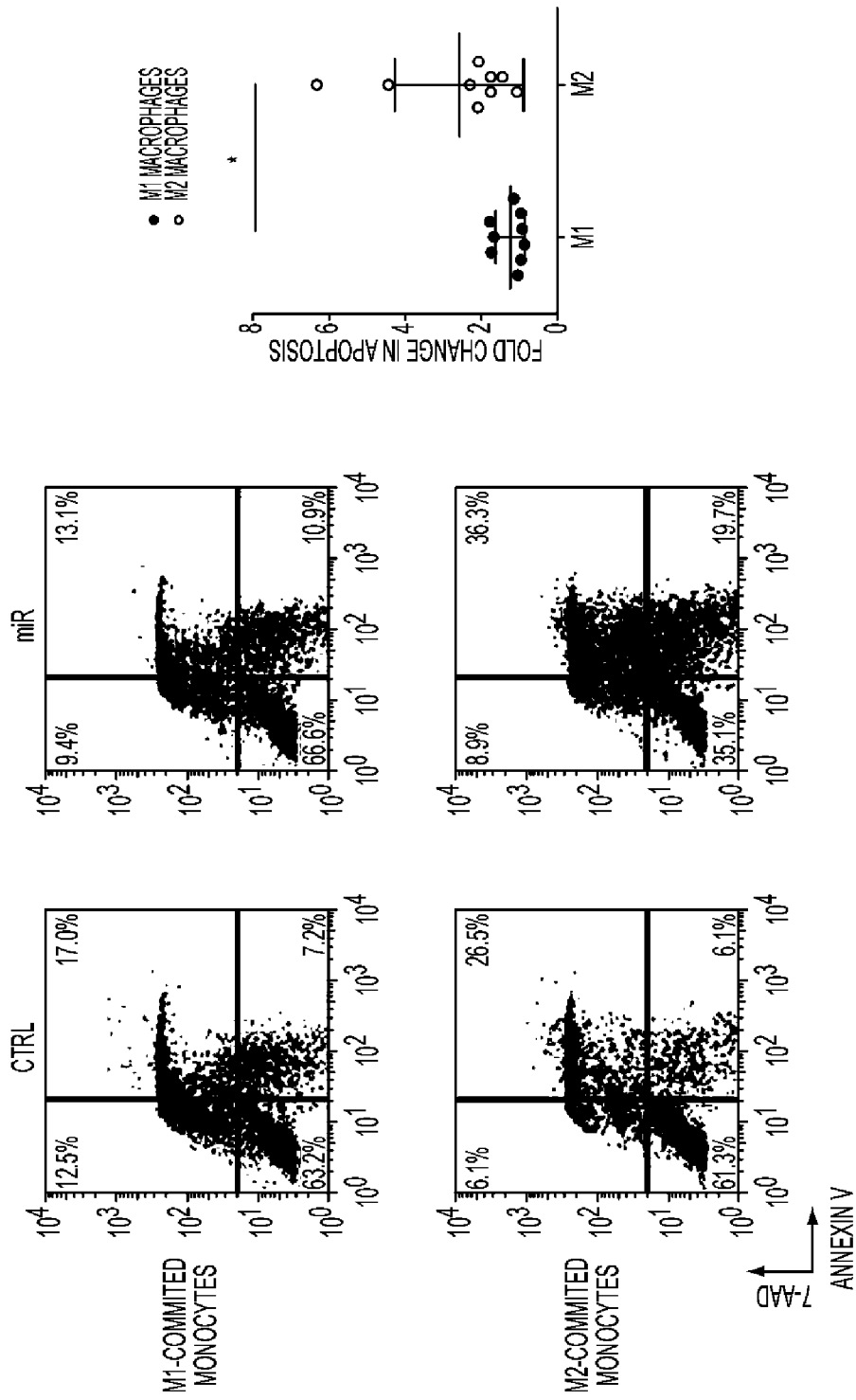
FIGS. 17A-B. miR-142-3p Transfection and TGFβR1 blockade Induces Selective Apoptosis in M2 Macrophages.
Figure 17B:
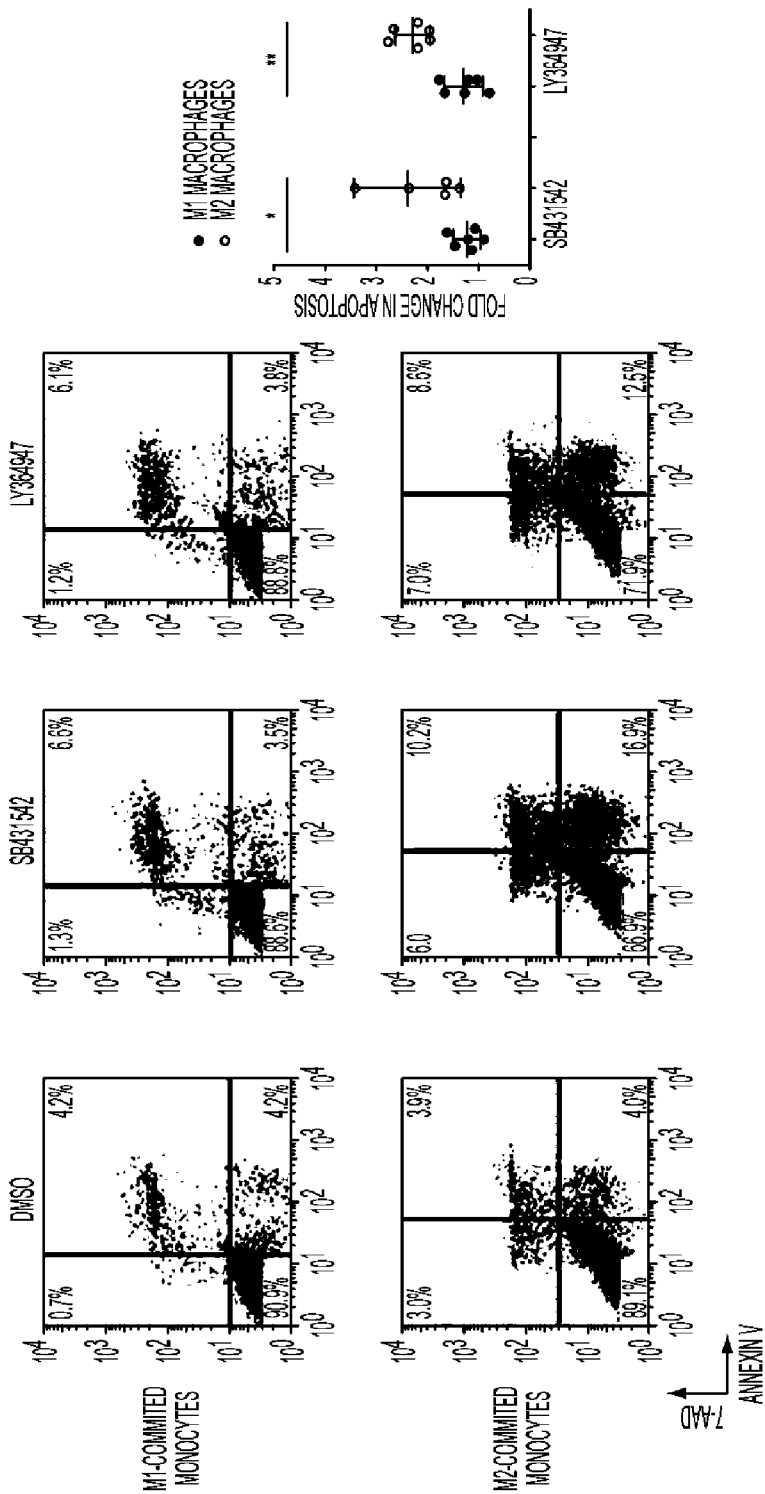
Figure 22A:
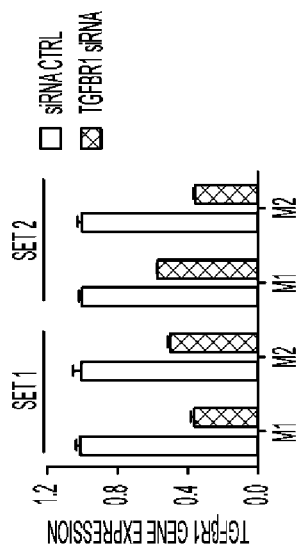
Figure 22B:
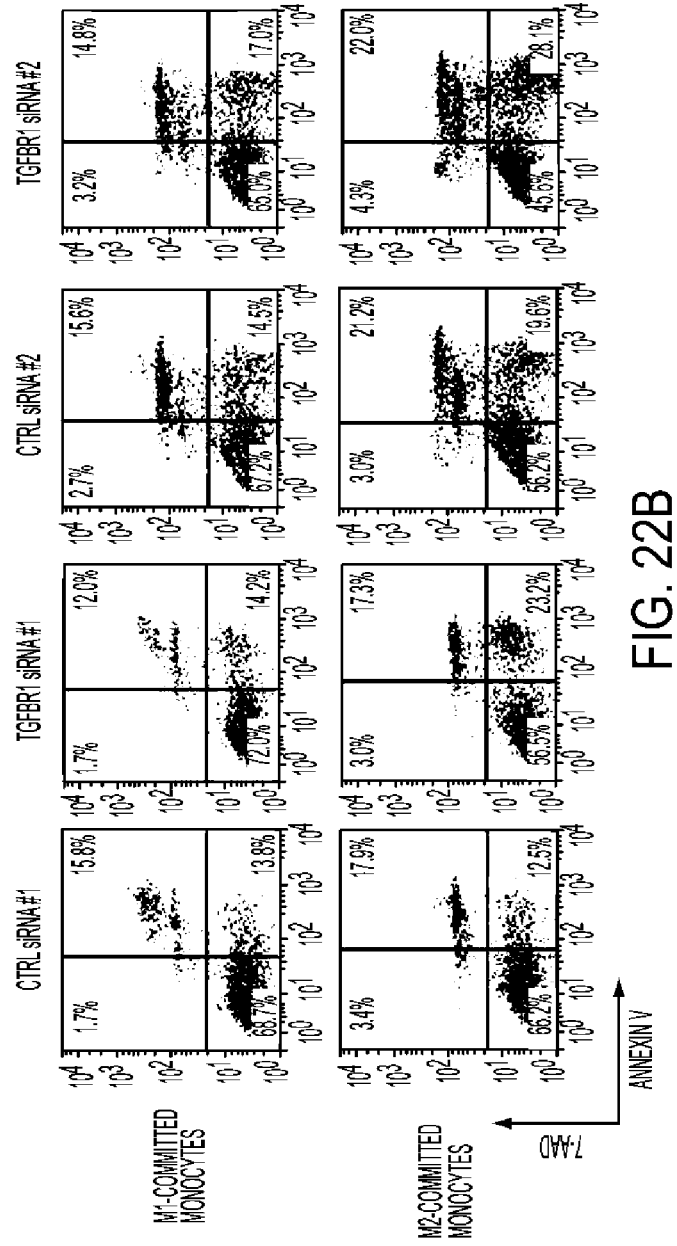
Figure 23B:
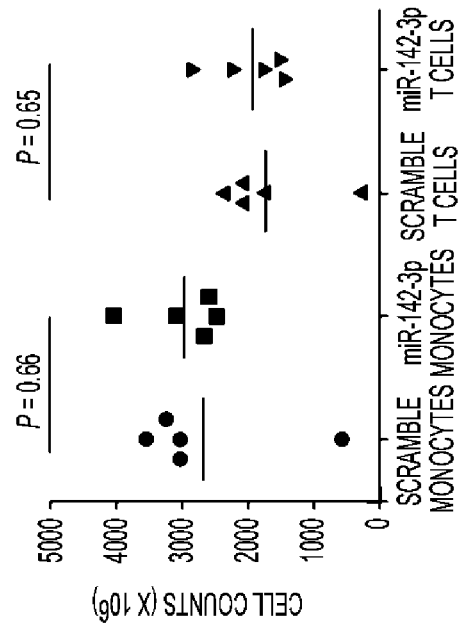
FIGS. 23A-B.
Figure 23A:
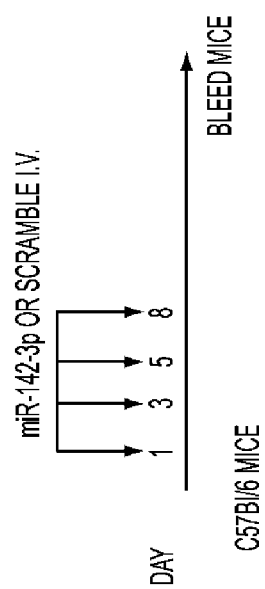

6. miR-142-3p Overexpression Induces Selective Apoptosis in M2 Macrophages Via TGF-β Blockade During in vitro culture of the monocytes and differentiated macrophages with miR-142-3p, a significant decrease in the relative cell number of the M2 macrophages was observed. Specifically, there was more early-(Annexin V$^+$ 7-AAD$^-$) and late-apoptosis/cellular death (Annexin V$^+$ 7-AAD$^+$) induced in M2-relative to M1 committed-monocytes at 48 hours after miR-142-3p transfection. The fold of change induced by miR-142-3p overexpression in M2 macrophages was 2.58±0.56, compared to 1.24±0.13 in the M1 macrophages (P=0.02, FIG. 17A). Because TGF-β has been shown to have a role in autocrine/paracrine growth of cells (Muraoka et al., 2002), TGFβR1 blockade in the M2 cells was investigated next, which may have autocrine dependency on this pathway, would induce selective apoptosis. Therefore, both M1- and M2-committed monocytes were treated with the TGFβRI inhibitors SB431542 and LY364947 to mimic the blockade potentially triggered by miR-142-3p transfection. Again, more apoptosis was observed within M2-committed monocytes treated with either antagonist than in the M1-committed monocytes (P=0.04 and 0.001, respectively; FIG. 4B). Moreover, knockdown of the TGFβR1 mRNA levels in M1/M2-committed macrophages with specific TGFβR1 siRNAs (FIG. 23A), induced preferential apoptosis in the M2 subset (FIG. 23B). All these data indicate that miR-142-3p overexpression induces selective apoptosis in M2 macrophages by blockade of the TGF-β receptor signaling pathway. Of note, this appears to be cell type specific since transfection of gCSCs with miR-142-3p did not induce significant apoptosis (FIG. 22D).

7. miR-142-3p Inhibits In Vivo Glioma Growth

Figure 18A:
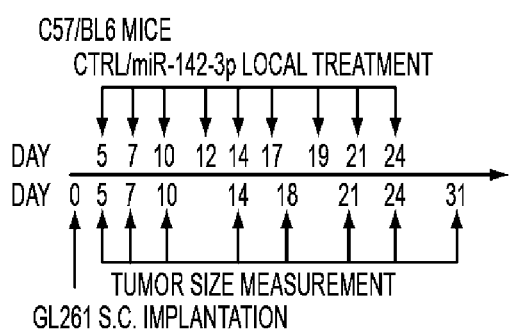
FIGS. 18A-D. miR-142-3p Inhibits In Vivo Glioma Growth. The treatment schema (FIG. 18A) and volume of subcutaneous (s.c.) GL261 tumors (FIG. 18B) in C57BL/6J mice treated intravenously with scramble control and miR-142-3p starting on day 5 (n=5 per group). Linear mixed models were fit to assess tumor growth and F-test was used. Standard deviations are shown. n=5/group, *P=0.03. The in vivo experiment was duplicated with similar results. Treatment schema (FIG. 18C) and graph of the Kaplan-Meier estimate of survival time in C57BL/6J mice implanted with intracerebral (i.c.) GL261 gliomas (FIG. 18D), which showed that miR-142-3p improved survival in the miR-142-3p-treated group relative to the scramble controls. Log rank tests were used to compare overall survival between groups. n=10/group. *P=0.03.
Figure 18B:
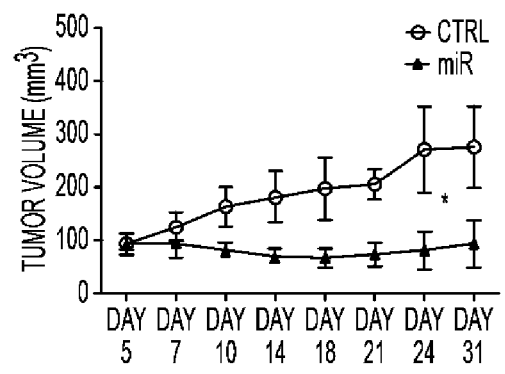

Considering the role of miR-142-3p in inducing M2 apoptosis by disruption of TGF-β receptor signaling pathway, miR-142-3p could exert an anti-tumor effect in vivo was investigated next. GL261 murine glioma cells were implanted subcutaneously into immune competent C57BL/6 mice. After the tumor mass had grown to a palpable size, either a scrambled miRNA sequence or miR-142-3p was administered locally (n=5 per group, FIG. 18A). As shown in FIG. 5B, aggressive tumor growth was observed in the scramble control group. In contrast, glioma growth was inhibited during the 3-week course of miR-142-3p treatment (P=0.03). All the mice were euthanized upon completion of the treatment course, and the tumor tissues were resected for H&E staining to confirm tumor formation. Subcutaneous tumors were found in only one out of five mice treated with the miR-142-3p duplex.

Figure 18C:
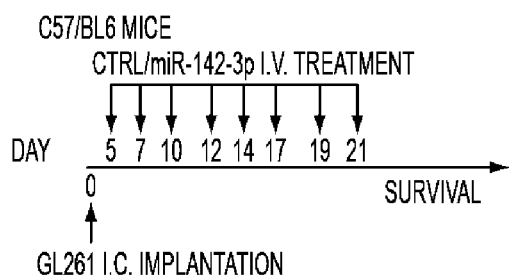
Figure 18D:
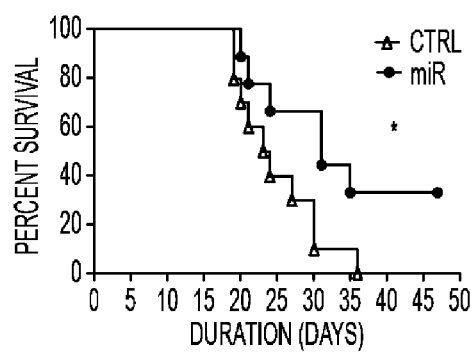

To determine whether miR-142-3p treatment can exert a similar anti-tumor effect against established intracerebral glioma, C57BL/6J mice harboring intracranial GL261 tumors were treated with miR-142-3p intravenously for 3 weeks (n=10 per group, FIG. 18C). The median survival duration for the scramble control group was 23.5 days, which was extended to 31 days for mice treated with miR-142-3p (P=0.03) (FIG. 18D). During the treatment course, no behavioral or neurological abnormalities were observed in the mice. Necropsies of glioma-bearing mice by the study neuropathologist demonstrated no evidence of demyelination, macrophage infiltration, or lymphocytic infiltration in the non-tumor-bearing areas of the CNS that would indicate the induction of autoimmunity The limitation of evaluating therapeutic strategies in clonotypic models has been previously noted (Huse et al., 2009). In a genetically engineered murine model system of high-grade glioma, it has been previously found that the gliomas have a marked influx of macrophages (Kong et al., 2010). Therefore, newborn Ntv-a mice were injected with RCAS-Bcl-2 and RCAS-PDGFB vectors and subsequently treated them with scramble control or miR-142-3p (FIG. 18E). The median survival duration in the control group was 24 days. In mice treated with miR-142-3p, the median survival duration was 32 days (P=0.03) (FIG. 18F).

8. miR-142-3p Inhibits In Vivo Glioma-Infiltrating Macrophages

Figure 19B:
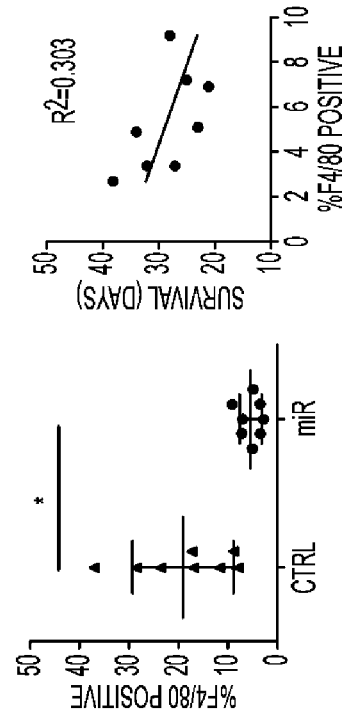
FIGS. 19A-D: miR-142-3p Inhibits Glioma-infiltrating Macrophages. Treatment schema (FIG. 19A) and graph of the Kaplan-Meier estimate of survival time (FIG. 19B) demonstrating improved survival in miR-142-3p-treated Ntv-a mice transfected with the RCAS-PDGFB and RCAS-Bcl-2 transgenes compared with scramble control. Log rank tests were used to compare overall survival between groups. n=9/group.*P=0.03.
Figure 19D:
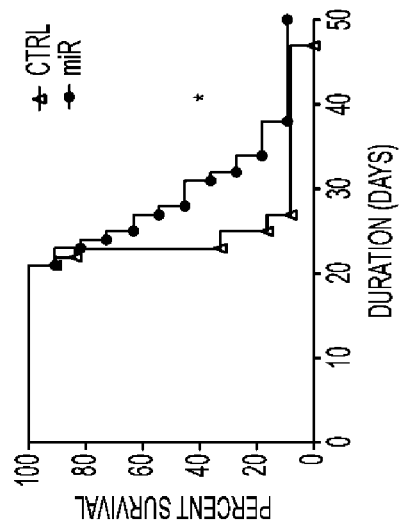
Figure 19A:
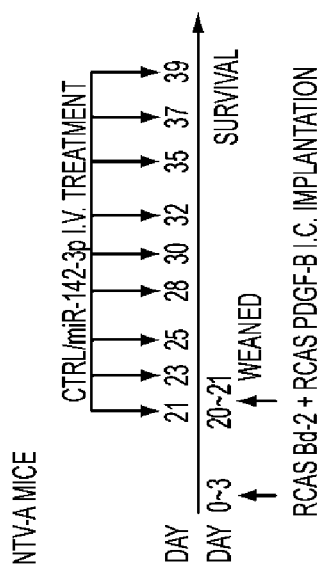
Figure 19C:
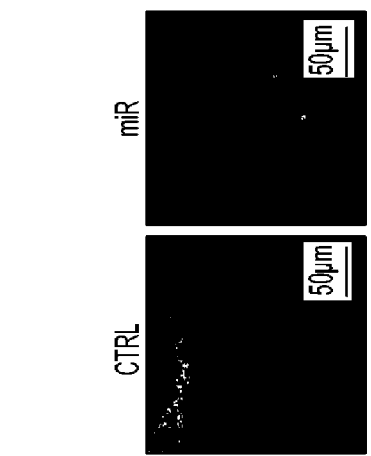
Figure 24A:
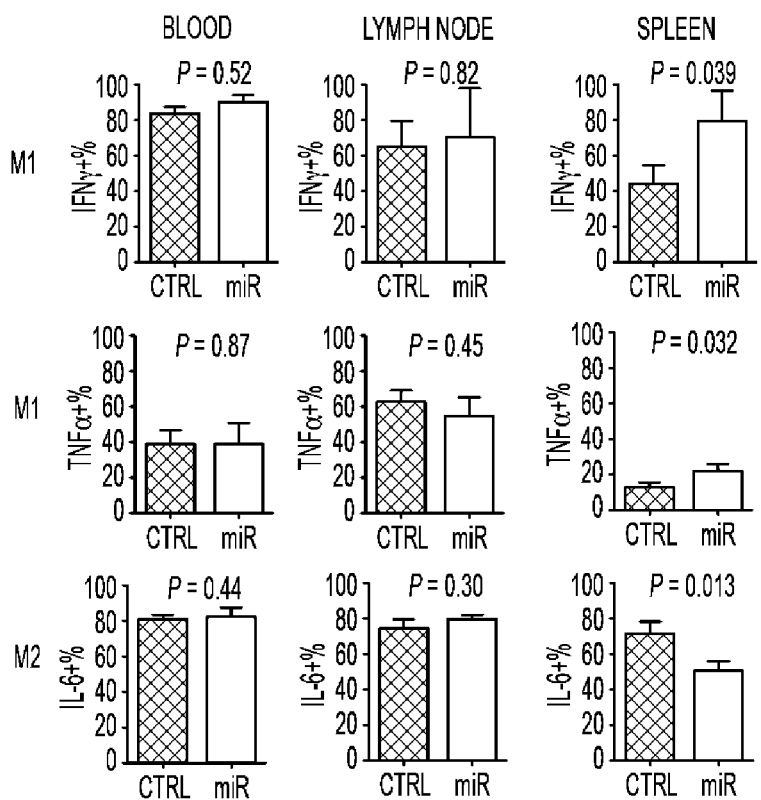
Figure 24B:
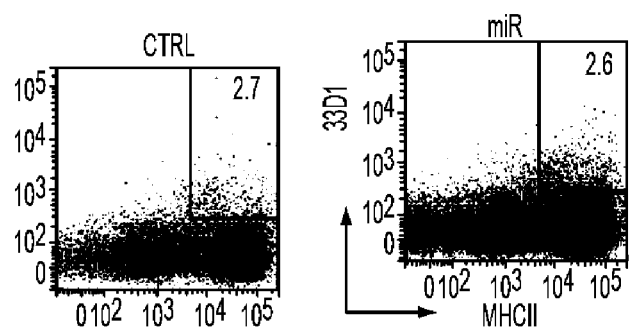

Systemic administration of miR-142-3p resulted in lower macrophage glioma infiltration compared to gliomas treated with scrambled miRNA (FIG. 19A). A negative linear correlation between infiltrating F4/80+ macrophages and survival duration in miR-treated animals was observed ($R^2$=0.303, FIG. 19B). More specifically, in a genetically engineered Ntv-a murine model system of high-grade glioma, miR-142-3p treated mice also had extended survival (median survival: 32 days versus 24 days, P=0.03, n=9, FIG. 19A and FIG. 19B). This model system has robust glioma-infiltrating macrophages (21) and treatment with miR-142-3p resulted in lower F4/80+ macrophage infiltration compared to the control group (FIG. 19C). A negative linear correlation was established between the infiltrating F4/80+ macrophages and survival in the miR-142-3p-treated mice (R2=0.303, FIG. 19D), indicating that miR-142-3p is exerting a therapeutic effect by modulating glioma-infiltrating macrophages. miR-142-3p suppressed CD11b+ macrophages elaborating IL-6 consistent with M2 skewed cells by 28% (P=0.01) and enhanced CD11b+ macrophages elaborating IFN-γ consistent with M1 skewed cells by 83% (P=0.03) within the spleen. In contrast, miR142-3p did not affect the functional M1 and M2 composition in blood and lymph nodes (FIG. 24A). However, there was no direct effect of miR142-3p on dendritic cell expansion, CD8+ effector responses as reflected by the production of effector cytokines such as IFN-γ, TNF-α and IL-2, or T-cell mediated tumor cytotoxicity (FIGS. 24B, 24C and 24D).

To the knowledge of the inventors, this is the first study describing a subtractive approach to identify the preferential expression profile of miRNAs within a specific immune population—the tumor-associated, immune suppressive, alternatively activated macrophage (M2) relative to its monocyte precursor. This subtractive screening strategy was intended to classify those miRNAs that are down regulated by the tumor microenvironment that should have biological roles in either the monocyte to macrophage differentiation state, skewing to or maintenance of the M2 phenotype, or play roles in M2-mediated immune suppression. As a result of the screening process, miR-142-3p emerged as a preferentially down-regulated leading candidate in glioma-associated macrophages. Although miR-142-3p has been shown to have a role in regulating immune suppression in the T cell compartment, its biological role in the tumor-associated M2 macrophage has not been previously described. Without wishing to be bound by any theory, these results support the idea that over expression of miR-142-3p induces selective apoptosis in the M2 macrophage population due to the inhibition of autocrine dependent TGFBR1. The specificity of miR-142-3p for TGFBR1 was predicted by multiple binding algorithms and confirmed by luciferase reporting assays, and mutational analyses.

It has been previously demonstrated that glioma cancer stem cells can induce M2 macrophages3 and that this population is a negative prognosticator in genetically engineered murine model systems of high-grade gliomas (Kong et al., 2010). The specific targeting of the M2 immune population in vivo for therapeutic intent is widely recognized as being desirable. Prior indirect targeting strategies have included inhibiting macrophage differentiation and cytokine production (Alavena et al., 2005), macrophage secretion of MMP-9 (Giraudo et al., 2004), or macrophage trafficking to the tumor microenvironment (Robinson et al., 2003). On the basis of multiple predictive binding algorithms, luciferase reporting assays, and mutational analyses, it has been show that miR-142-3p targets the TGFβR1 pathway. This finding was further supported by the results of in vitro studies that demonstrated preferential TGFβR1 pathway inhibition by miR-142-3p in M2 cells and diminished macrophage infiltration within the glioma microenvironment. It has been found that miR-142-3p induces selective apoptosis in the M2 macrophage population due to the inhibition of TGFβR1. This induction of selective M2 apoptosis by inhibiting the TGFβR1 pathway was further validated with small molecule SB431542 and LY-364947, which are inhibitors of TGFβR1 and by siRNA of TGFβR1. Although LY-364947 also has inhibitory effects on VEGF (Vogt et al., 2011), which can induce macrophage to M2 skewing under selective conditions (Linde et al., 2012), preponderant evidence relying on the more specific TGFβR1 blockade data (i.e. SB431542 and siRNA), indicates that the induced M2 macrophage apoptosis is secondary to inhibition of its dependent TGFβR1 pathway. Although autocrine growth dependence on TGF-β has been shown in cancer cells (Muraoka et al., 2002), these observations can now be extended to the immune suppressive M2 macrophage. Thus, the demonstrated mechanism of direct targeting of the M2 macrophage by disrupting autocrine TGFβR1 stimulation is also novel and not previously described.

In vivo targeting of TGFβR1, especially in the circulating monocytes as they become differentiated to the M2 macrophages in glioma-bearing mice, exerted a therapeutic effect against malignant gliomas in a variety of model systems. In vivo therapeutic efficacy has not been demonstrated with other TGFβR1-targeted therapeutics including the small molecules (Bouquet et al., 2011; Halder et al., 2005; Hjelmeland et al., 2004). The therapeutic effect of miR-142-3p in vivo directly correlated with a decreased glioma macrophage infiltration—specifically the M2 population. The exploitation of the immune system to mediate the therapeutic effects of miRNA, such as miR-142-3p, can circumvent previous limitations of miRNA delivery, including getting past the blood-brain-barrier. Furthermore, circulating immune cells are the first point of contact to administrated miRNAs—affording an opportunity to directly modulate their functional activity. Despite a therapeutic effect of miR-142-3p against established intracerebral gliomas was evident, therapeutic "cures" were not frequently observed, especially in the heterogeneous, genetically engineered murine models. The heterogeneity of immune suppressive mechanisms and pathways exploited by malignant gliomas is widely acknowledged and documented. Thus, to target TGFβR1 alone would not be anticipated to result in a cure in clinic. Patients that have glioblastomas with an enrichment of M2 in the local tumor microenvironment may be particularly response to treatment with miR-142-3p.

Treatment with miR142-3p was well tolerated and there was no evidence of CNS toxicity or induced autoimmunity during administration of miR-142-3p to mice was observed, including demyelination and macrophage/lymphocyte infiltration in the normal, non-tumor-bearing brain. Although miR-142-induces preferential apoptosis in the M2 population, the peripheral monocyte counts of treated mice was not affected by miR-142-3p systemic administration, probably secondary to the pre-existing expression of miR-142-3p in these cells and their lack of dependency on the TGFβR1 pathway. Moreover, an oncogenic effect of miR-142-3p in human T-cell acute lymphoblastic leukemia has been reported (Lv et al., 2012); however, any significant differences in lymphocyte counts between the miR-142-3p-treated and control mice in the peripheral blood were observed. Reconciliation of these results suggests that miR-142-3p plays differential roles (oncopromoter versus oncosuppressor) in different malignancies.

In this study, the following approach to identify miRNA immune therapeutics using a two-step process was used: 1) screen miRNA expression from tumor-associated immune cells relative to normal immune cell, and 2) select and prioritize potential candidates on the basis of binding to immunosuppressive pathways or mechanisms. Several of the alternative candidates identified in the human miRNA microarray expression library may have roles in modulating Treg induction pathways and expression of TGF-β, IL-10, CTLA-4, and PD-1. Other candidate miRNAs in this study are being evaluated for their potential as therapeutic agents and could be used in a complementary or alternative fashion with miR-142-3p. Additionally, miRNAs would be easier and cheaper to produce than antibodies and are not confined to targets on the cell surface membrane. As has already been shown the proof of principal that miRNAs can reverse tumor-mediated immune suppression; reciprocally, it is obvious, that miRNAs could be identified by screening the immune cells from patients with autoimmune diseases relative to normal subjects then selecting the down regulated miRNAs that block pro-inflammatory responses. This miRNA identification strategy can be used to identify cancer therapeutics; alternately, this approach may be used to identify novel therapeutics for autoimmune disorders.

Example 3 miR-138 Exerts Anti-Glioma Efficacy by Targeting Immune Checkpoints

A. Materials and Methods

1. Human Glioblastoma Cancer Stem Cells and Glioma Cell Lines

The gCSCs were derived as previously described (Bao et al., 2006) and were characterization based on the criterion of in vivo tumorigenic potential, pluripotent potential, limiting dilution assays and cytogenetic characterization which is consistent with our previously published reports (Wei et al., 2010; Wu et al., 2010). The gCSCs were cultured in vitro with neurosphere medium consisting of Dulbecco's modified Eagle's medium/F-12 medium containing 50 ng/mL of both epidermal growth factor (EGF) and fibroblast growth factor 2 (FGF-2). The murine glioma GL261 cell line was obtained from the National Cancer Institute-Frederick Cancer Research Tumor Repository and maintained in Dulbecco's modified Eagle medium (Life Technologies; Grand Island, N.Y.), supplemented with 10% fetal bovine serum (Atlanta Biologicals, Norcross, Ga.), 1% penicillin/streptomycin (Life Technologies), and 1% L-glutamine (Life Technologies). The cells were split every 3 days to ensure logarithmic growth. The cells were harvested, washed and then stained for 30 minutes at 4° C. as described above for the ex vivo glioblastoma tumors.

2. Isolating Total RNA from Glioblastoma

Tumors were pathologically confirmed as glioblastoma (World Health Organization grade IV) by a board-certified neuropathologist. Tumors were washed in RPMI medium and dissected to remove blood products and surrounding non-tumor brain tissue. The total tissue was broken down into smaller pieces and digested for 2 hours using a cancer cell isolation kit (Panomics). The cells were suspended in RNAlater solution (Ambion, Austin, Tex.) in RNase Free tubes and stored at 4° C. overnight; after 24 hours, they were transferred to −20° C. until needed for total RNA extraction. Extraction was performed using the mirVana kit (Ambion). Once extracted, RNA levels were analyzed for concentrations and purity using UV/Vis spectroscopy at 230, 260, and 280 nm.

3. miR Comparison in Glioblastoma and Normal Brain Tissue

Total RNA extracted from patients was sent to Phalanx Biotech Group (Belmont, Calif.) for microRNA and mRNA-gene expression analyses. Total RNA of normal brain tissues was obtained from Biochain (Hayward, Calif.). The results of the glioblastoma miR analysis were used to determine which miRs had significant differences in expression compared with normal donor miRs. Fold differences were calculated with Microsoft Excel. MiRs with the most significant differences in expression levels were chosen for the miR target analysis using TargetScan (Release 5.1) and RNA22 (FIGS. 25A-D). miRs of interest were selected on the basis of putative targets and the degree of deviation from normal monocytes.

4. Glioma Tissue Microarrays

This analysis was conducted according to the MD Anderson approved LAB09-0463, which includes one set of tumor microarrays (TMA) of patients with different glioma grades and pathologies and is designated "glioma" TMA and includes WHO grade IV glioblastomas (n=53), WHO grade III anaplastic astrocytomas (n=17), WHO grade II low-grade astrocytomas (n=3), WHO grade II oligodendrogliomas (n=16), WHO grade III anaplastic oligodendrogliomas (n=15), WHO grade II mixed oligoastrocytomas (n=6), WHO grade III anaplastic mixed oligoastrocytomas (n=12), and WHO grade IV gliosarcomas (n=7) and has been previously described (Barnett et al., 2007). A second glioblastoma-specific TMA was constructed under PA12-0136 and contains 99 glioblastomas. For TMA construction, two 1-mm cores were obtained per tumor sample. The rationale for using a TMA was to facilitate an analysis of the largest number of tumor samples possible. The study neuropathologist (G.N.F.) gathered the tissue sections from the archived paraffin blocks and confirmed the tumor pathologic type. The time from resection to fixation was less than 20 minutes in all cases, in accordance with the Clinical Laboratory Improvement Amendments standard.

In situ hybridization was performed using the protocol developed by Nuovo et al (Nuovo et al., 2009), with some minor adjustments as we have previously described (Wei et al., 2013). Digoxigenin-labeled, locked nucleic acid-modified probes for miR-138 (hsa-miR-138) and the positive control (U6, hsa/mmu/rno) were purchased from Exiqon (Vedbek, Denmark) and were used for detecting miR-138 expression on the TMA. The colorimetric reaction was monitored visually and stopped by placing the slides in water when background coloring started to appear. The TMA was analyzed by the study neuropathologist (G.N.F.). In the assessment of miR-138 expression in gliomas, intervening neurons in the infiltrating component were not considered positive.

5. miR Relative Expression Survival Analysis

Complete data for 383 glioblastoma patients that included expression of miR-138 and PD-L1, together with survival data, was downloaded from The Cancer Genome Atlas (TGCA). The Kaplan-Meier survival curve data was plotted for the top 50% versus bottom 50% miR-138 expression and top 20% versus lowest 20% expression using GraphPad Prism5 (GraphPad Software, Inc., La Jolla, Calif.).

6. PD-L1 Expression in Glioblastomas

The glioblastoma TMA was de-paraffinized in xylene and rehydrated in ethanol. We used a commercial Abcam (Cambridge, Mass., USA) polyclonal anti-PD-L1 antibody. The slides were de-paraffinized in xylene and rehydrated in ethanol. Antigen retrieval was carried out for 30 minutes in citric acid buffer (pH 6.0). Endogenous peroxidase activity was blocked with immersion in 0.3% hydrogen peroxide in methanol for 30 minutes. Slides were blocked with 1:100 normal goat serum for 20 minutes at room temperature and then they were incubated with the primary antibody at a 1:200 dilution at 4 degrees overnight. The slides were incubated with a goat anti-rabbit secondary antibody at 1:200 for one hour, and then with the avidin/biotin complex (Vectastain ABC kit, Vector Laboratories, Burlingame, Calif., USA) at 1:100 for one hour. Visualization was performed with the chromagen DAB (Sigma-Aldrich Corp., St Louis, Mo., USA), slides were counterstained with hematoxylin, dehydrated and mounted. The TMA was inspected under 200× magnification and the positive stained cells were quantified under the direct supervision of the study neuropathologist.

To secondarily validate these findings, glioblastoma surgery specimens were processed within 4 h after resection. To detect PD-L1 expression on ex vivo glioblastoma cells by flow cytometry analysis, the 10F.9G2 clone was used (Biolegend, San Diego, Calif.). Briefly, the tumor was mechanically dissociated, enzymatically digested for one hour in Liberase™, passed sequentially through 100 and then 70 micron filters, incubated in red cell lysis buffer for 15 minutes, then spun, blocked and then stained with the PD-L1 antibody or isotype control for 20 minutes at 4° C. Data acquisition was performed using the Beckman Coulter Gallios flow cytometer (Beckman Coulter, Brea, Calif.). Analysis was performed using FlowJo software.

7. Luciferase Assay

To determine whether miR-138 can bind to CTLA-4 3'-UTR and or PD-1 3'UTR, H9 (ATCC, Manassas, Va.) cells were co-transfected with the designated luciferase reporter plasmid (pMirTarget, Origene, Rockville, Md.) and miR-138 expression plasmid or scramble control plasmid (GeneCopoeia) with Lipofectamine 2000 transfection reagent (Invitrogen). A control set of H9 cells were transfected with the luciferase reporter plasmid without the addition of a 3' UTR to evaluate for off-target effects of miRNA-138 on the reporter plasmid itself. *Renilla luciferase* reporter plasmid was included as an internal control for transfection efficiency. The interaction between miR-138 and its target were measured by comparing the results of the co-transfection of the CTLA-4 3' UTR, or PD-1 3'-UTR-luciferase reporter and miR-138 plasmids with those of the 3' UTR-luciferase reporter plasmid and the scramble control plasmid. We also transfected HeLa reporter cells and performed the same analysis with mutant CTLA-4 and PD-1 3' UTR luciferase reporter plasmids. For each mutant, we changed 5 base-pairs; one mutant each was generated for the miR-138 binding site of PD-1, one mutant was created for each of the miR-138 binding sites of CTLA-4, and one mutant was created with all three binding sites mutated. The luciferase assay was performed using the Dual-Luciferase® reporter assay system (Promega, E1910). Firefly luciferase activity was normalized by *renilla luciferase* activity.

8. In Vivo Experiments

The miR-138 duplex that mimics pre-miR-138 (sense: 5'-AGCUGGUGUUGUGAAUCAGGCCGU-3' (SEQ ID NO:20), antisense: 5'-GGCCUGAUUCACAACACCA-GCUGC-3'(SEQ ID NO:21)) and the scramble control miRNA duplex (sense: 5'-AGUACUGCUUACGAUACG-GTT-3' (SEQ ID NO:22), antisense: 5'-CCGUAUCGUAAGCAG UACUTT-3' (SEQ ID NO:23)) were synthesized (SynGen, San Carlos, Calif.). The sequence of murine miR-138 is identical to human miR-138 on the basis of NCBI blast data. The treatment cohorts consisted of 2 µL miR-138 or scramble control (10 µg/µL)+ 48 µL of phosphate-buffered saline (PBS) mixed with the vehicle (40 µL PBS+10 µL lipofectamine 2000) or the vehicle control (90 µL PBS+10 µL lipofectamine 2000). Mice were maintained in the MD Anderson Isolation Facility in accordance with Laboratory Animal Resources Commission standards and conducted according to the approved protocol 08-06-11831.

9. Syngeneic Subcutaneous Model

The B16 cells were kindly provided by Dr. Willem Overwijk (the University of Texas M.D. Anderson Cancer Center, Houston, Tex.) and were maintained in RPMI 1640 medium supplemented with 10% FBS at 370 C in a humidified atmosphere of 5% CO2 and 95% air. The murine glioma GL261 cell line was obtained from the National Cancer Institute-Frederick Cancer Research Tumor Repository and maintained in Dulbecco's modified Eagle medium (Life Technologies; Grand Island, N.Y.), supplemented with 10% fetal bovine serum (Atlanta Biologicals, Norcross, Ga.), 1% penicillin/streptomycin (Life Technologies), and 1% L-glutamine (Life Technologies). The cells were split every 3 days to ensure logarithmic growth.

To induce subcutaneous tumors, logarithmically growing GL261 cells were injected into the right hind flanks of 6-week-old C57BL/6J female mice or nude mice at a dose of 1×106 cells suspended in 100 µl of PBS diluted matrigel basement membrane matrix (BD Biosciences) (PBS:Matrigel=2:1). When approximately 0.5 cm palpable tumors formed, the mice (n=5/group) were treated by local tumor or intravenous injection. Tumors were measured twice a week. Mice that showed signs of morbidity, high tumor burden, or skin necrosis were immediately euthanized according to MD Anderson guidelines. Tumor volume was calculated with slide calipers using the following formula: $V=(L \times W \times H)/2$, where V is volume ($mm^3$), L is the long diameter, W is the short diameter, and H is the height.

10. Syngeneic Intracranial Glioma Model

To induce intracerebral tumors in C57BL/6J mice and athymic nude mice, GL261 cells or B16 cells were injected into the cerebrum. These cells were collected in logarithmic growth phase, washed twice with PBS, mixed with an equal volume of 10% methyl cellulose in Improved modified Eagle's medium Zinc Option medium, and loaded into a 250-µl syringe (Hamilton, Reno, Nev.) with an attached 25-gauge needle. The needle was positioned 2 mm to the right of bregma and 4 mm below the surface of the skull at the coronal suture using a stereotactic frame (Kopf Instruments, Tujunga, Calif.), as we previously described (Heimberger et al., 2003). The intracerebral tumorigenic dose for GL261 cells was 5×104 and for B16 was 5×102 in a total volume of 5 µl. Mice were then randomly assigned to control and treatment groups (n=10/group for GL261, n=6-7/group for B16). Animals were observed three times per week, and when they showed signs of neurological deficit (lethargy, failure to ambulate, lack of feeding, or loss of >20% body weight), they were compassionately euthanized. These symptoms typically occurred within 48 hours of death. The brains were removed and placed in 4% paraformaldehyde and embedded in paraffin.

11. Genetically Engineered Murine Model of Glioma

We have previously described the use of immune competent Ntv-A mice with RCAS-PDGFB+RCAS-Bcl-2 induced high-grade gliomas for testing immune therapeutics (Kong et al., 2010). Briefly, the transgenic Ntv-a mice are mixtures of different strains, including C57BL/6, BALB/c, FVB/N, and CD1. PDGFB and Bcl-2 are transferred into the cerebral hemispheres of mice by injection of RCAS vectors containing these genes at the coronal suture on postnatal days 1 or 2. The mice are randomized to treatment starting on day 21 with anti-CTLA-4 antibody (clone 9H10), isotype control, miR-138, or scramble control. The miR-138 treatment was injected on Monday, Wednesday and Friday for three weeks, while the anti-CTLA-4 was delivered by intraperitoneal injections on day 21, 24 and 27 as previously described (Fecci et al., 2007). The mice were monitored for morbidity from tumor burden, and were euthanized if present. If not, all mice were euthanized at 90 days, the brains were removed, and analyzed for tumor formation and grading by the study neuropathologist.

12. Immunohistochemistry of Treated Gliomas

Formalin-fixed, paraffin-embedded sections of the treated and untreated GL261-implanted brains and the Ntv-A mice harboring gliomas were deparaffinized in xylene and rehydrated in ethanol. Antigen retrieval was performed by immersing the sections in a citrate-buffered solution (pH 6.0), heating them in the microwave for 2 minutes, then maintaining heat by placement in a steamer for 30 minutes. The samples were then cooled to room temperature. Endogenous peroxidase was blocked with 0.3% hydrogen peroxide/methanol for 30 min at room temperature. After blocking with a protein block serum-free solution (DAKO, Carpinteria, Calif.), diluted antibody anti-FoxP3 antibody (eBioscience) was applied. The samples were then washed and incubated with the appropriate secondary antibody for one hour. They were then washed and incubated with streptavidin for one hour, and then each sample was developed using the SigmaFAST DAB kit (Sigma-Aldrich, St Louis, Mo.). Color development was stopped by gently dipping the slides in distilled water. The nuclei were then counterstained with hematoxylin.

13. Isolation of Human CD4+ T Cells

Human PBMCs were prepared from blood donated by healthy volunteers and glioblastoma patients undergoing resection at The University of Texas MD Anderson Cancer Center (Houston, Tex.). The PBMCs were isolated by centrifugation on a Ficoll-Hypaque density gradient (Sigma-Aldrich, St. Louis, Mo.) and the CD4+ T cells were purified by negative selection microbead magnetic cell sorting according to the manufacturer's instructions (BD Biosciences, San Jose, Calif.).

14. miR-138 Transfection in T Cells

CD4+ T cells purified from healthy donor PBMCs at 0.5 million/ml were plated on anti-CD3/anti-CD28 antibody (BD Biosciences, San Jose, Calif.) pre-bound 24-well plates for 48 hours for TCR activation and cell proliferation either with or without the addition of 5 ng/ml TGF-β. CD4+ cells were then harvested, washed and transfected with miR-138 or scramble RNA expressing vectors (GeneCopoeia, Rockville, Md.) via the Nucleofector human T cells transfection kit (Lonza, Allendale, N.J.; program: T-023).

15. Functional Analysis of T Cells

CD4+ cells transfected with miR-138 or scramble RNA-expressing vectors, with or without activation by TGF-β, as above, were plated into 96 well plates in 100 ul samples. Cells were surface stained with antibodies to PD-1 (conjugated to PercP, from eBioscience) and CTLA-4 (conjugated to PE, from BD) and permeabilized for intracellular staining of FoxP3 (conjugated to APC, from eBioscience). Samples were then evaluated by flow cytometry. The samples were gated for live cells, and the expression of PD-1, CTLA-4 and FoxP3 were evaluated. For ICOS determinations, CD4+ cell enrichment, transfection, activation and plating were as above. Cells were then permeabilized for ICOS staining (conjugated to APC, eBioscience 17-9948-42) and evaluated by flow cytometry.

16. Real-Time PCR to Confirm Relative miR-138 Expression Levels

Total RNA extracted from T cells, including those transfected with miR-138, was used as the template for reverse transcription using the TaqMan reverse transcription kit (Applied Biosystems, Carlsbad, Calif.) in a thermocycler per the manufacturer's instructions. Primers for reverse transcription were purchased for human miR-138 and U18 (Applied Biosystems). U18 was used as an endogenous control. cDNA was used as the template for real-time PCR. U18 and miR-138 amplifications were run in duplicate using the TaqMan real-time PCR kit (Applied Biosystems) in the 7500 real-time PCR system (Applied Biosystems). Further reactions, substituting water for the cDNA template, were used as additional controls. Excel was used to calculate the mean levels of each miR and the U18 internal control. The relative expression levels of miR-138 were compared with those of the internal controls.

17. Statistics

Survival differences on Kaplan-Meier curves were calculated in the GraphPad Prism5 software using the Log-rank (Mantel-Cox) test.

B. Results 1. miR-138 Expression in Glioblastoma

To determine the pattern of miR expression in glioblastoma relative to normal brain tissue, we used the Human miRNA OneArray Microarray v2 (Wei et al., 2013). The identified down-regulated miRs were then screened for potential targeting to the immune checkpoints CTLA-4 and PD-1 using RNA22. miR-138 emerged as a leading candidate with a mean 13.4-fold decrease in expression from normal brain tissue and with three binding sites in the 3' UTR of CTLA-4 and one within in PD-1. A subsequent analysis using reverse transcription-polymerase chain reaction (RT-PCR) confirmed that miR-138 was absent or minimally expressed in glioblastoma specimens (mean=0.20; range: 0.003 to 0.65; n=3) and glioma cell lines (mean=0.28; range: 0.10 to 0.45; n=4) relative to normal brain tissues (mean=3.9; range: 1.7 to 7.0; n=3). Using a glioma tumor microarray and in situ hybridization, heterogeneous expression of miR-138 was found amongst all glioma grades and pathological subtypes (Table 7). No difference in survival time among glioblastoma patients was found on the basis of the relative expression of miR-138 in The Cancer Genome Atlas data set (FIGS. 29A-B) consistent with data from a previously published report (Chan et al., 2012).

TABLE 7 miR-138 Expression in Gliomas

|  | n | WHO grade | − | + | ++ | +++ |
|---|---|---|---|---|---|---|
| Mixed oligoastrocytoma | 6 | II | 0 | 50 | 50 | 0 |
| Oligodendroglioma | 25 | II | 0 | 48 | 48 | 4 |
| Low-grade astrocytoma | 3 | II | 0 | 100 | 0 | 0 |
| Anaplastic oligodendroglioma | 16 | III | 5 | 57 | 25 | 13 |
| Anaplastic mixed oligodendroglioma | 12 | III | 0 | 25 | 58 | 17 |
| Anaplastic astrocytoma | 40 | III | 12 | 58 | 28 | 2 |
| Gliosarcoma | 11 | IV | 0 | 46 | 54 | 0 |
| Glioblastoma | 87 | IV | 8 | 53 | 31 | 8 |

2. miR-138 Inhibits Tregs by Targeting Immune Checkpoints

Figure 25A:
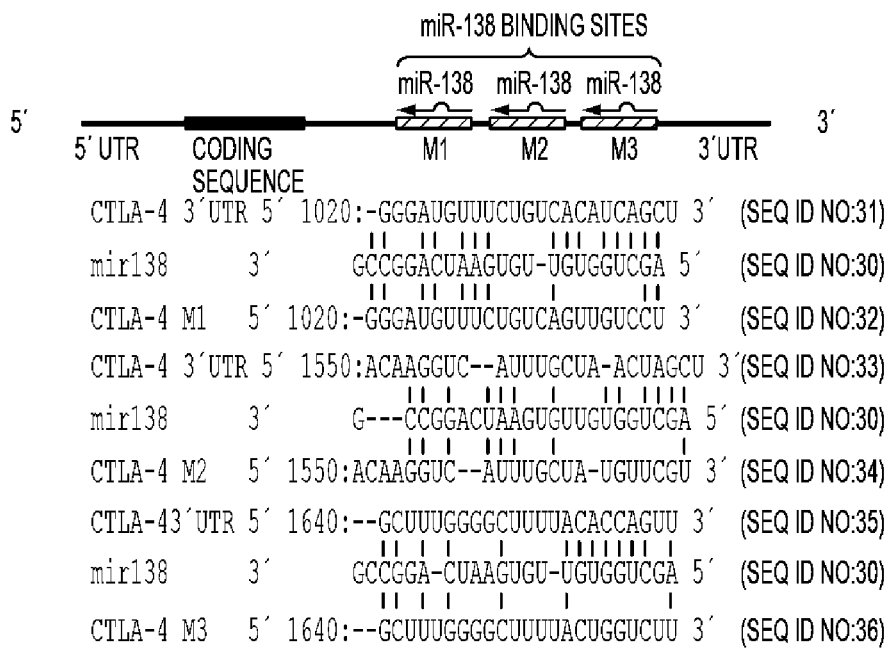
FIGS. 25A-C: miR-138 binds the 3' UTR of CTLA-4 and PD-1.
Figure 25B:
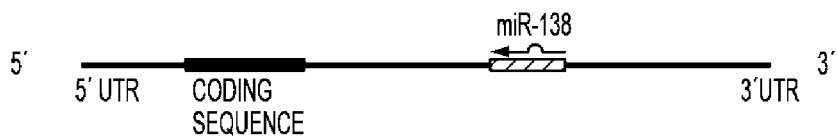
Figure 25C:
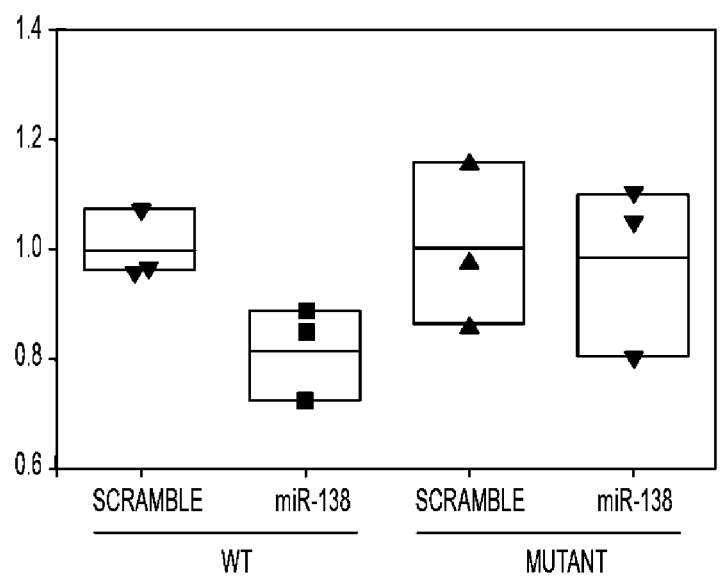

To validate the targets prove that miR-138 binds to the immune checkpoint molecules, luciferase expression assays were conducted including mutating the predicted CTLA-4 and PD-1 3'-UTR binding sites of miR-138 (FIG. 25A-B). PD-1 luciferase activity was significantly inhibited by 18±5.0% by miR-138; whereas mutational alteration of the miR-138 PD-1 3'-UTR binding site abolished the inhibitory effect of the miR-138 on PD-1 expression (FIG. 25C).

Figure 26A:
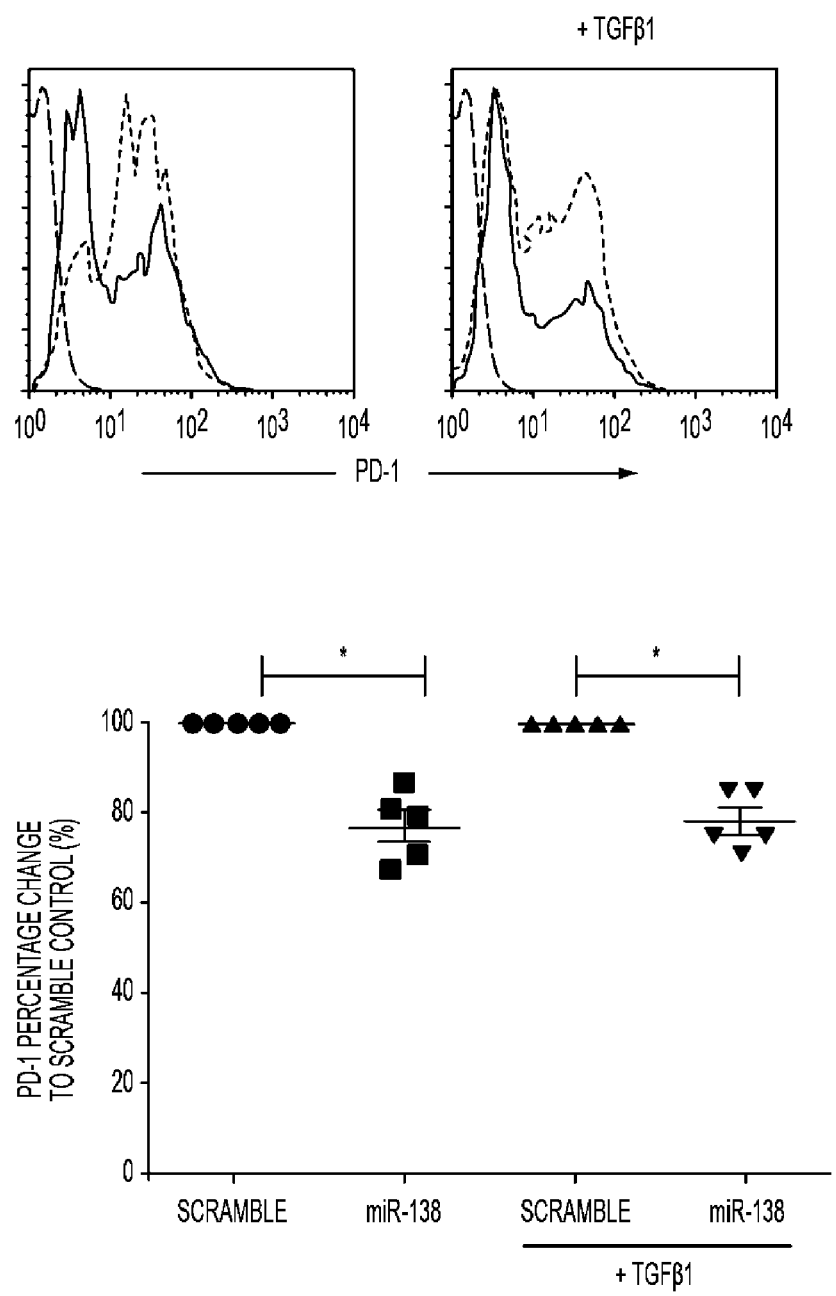
FIGS. 26A-C: miR-138 inhibits human checkpoint expression in Tregs. Healthy donor human CD4+ T cells were stimulated by anti-CD3/CD28 Abs for 48 h in the absence or presence of TGF-β to induce CTLA-4, PD-1 and FoxP3+ Tregs and subsequently transfected with miR-138 or scramble control. MiR-138 down modulated the expression of PD-1 (FIG. 26A), CTLA-4 (FIG. 26B) and FoxP3 (FIG. 26C) in CD4 T cells. Solid grey filled histogram is isotype control, dashed histogram is scramble control and solid black line is miR-138. Representative histograms are shown as above and summary data dot plots are shown below in which each dot represents the analysis of one human donor's peripheral CD4+ T cells (n=5). * indicates P<0.05.
Figure 26B:
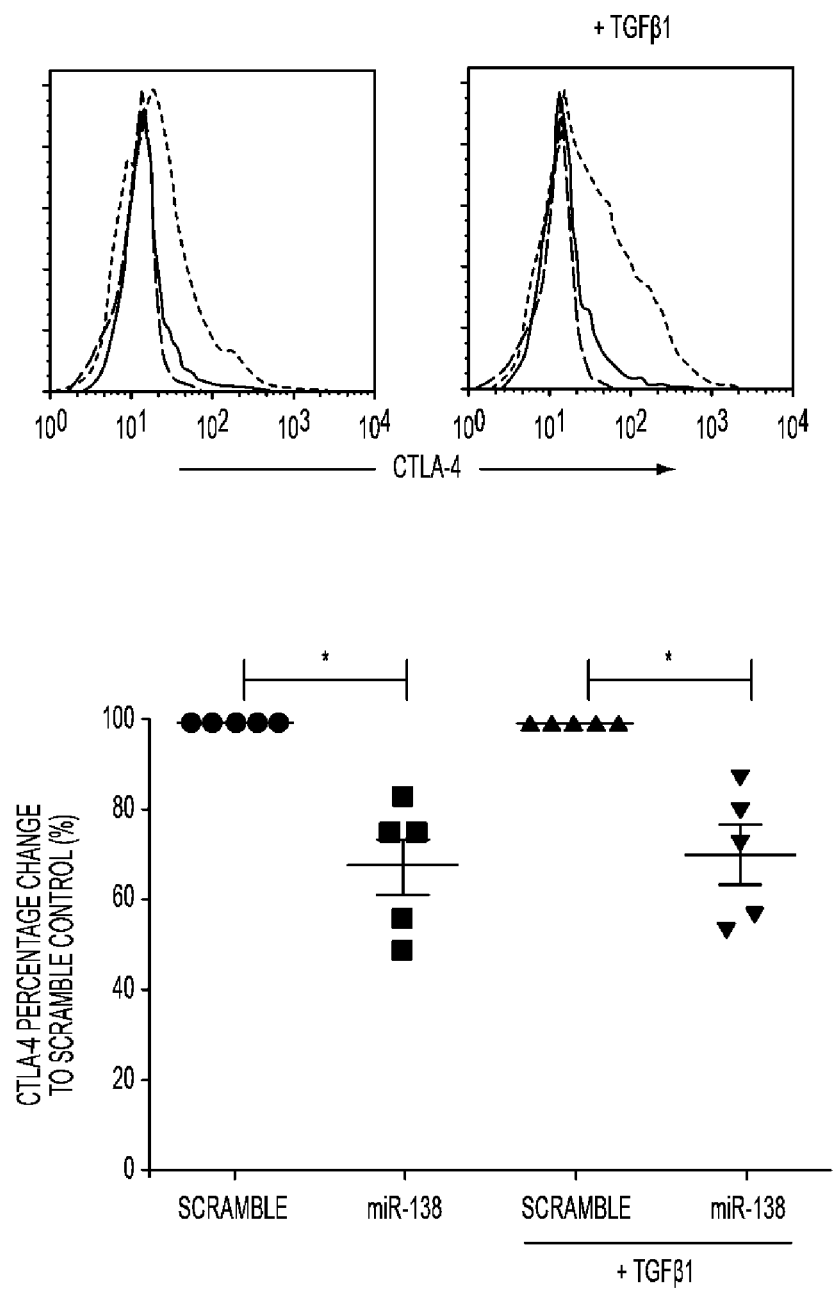
Figure 26C:
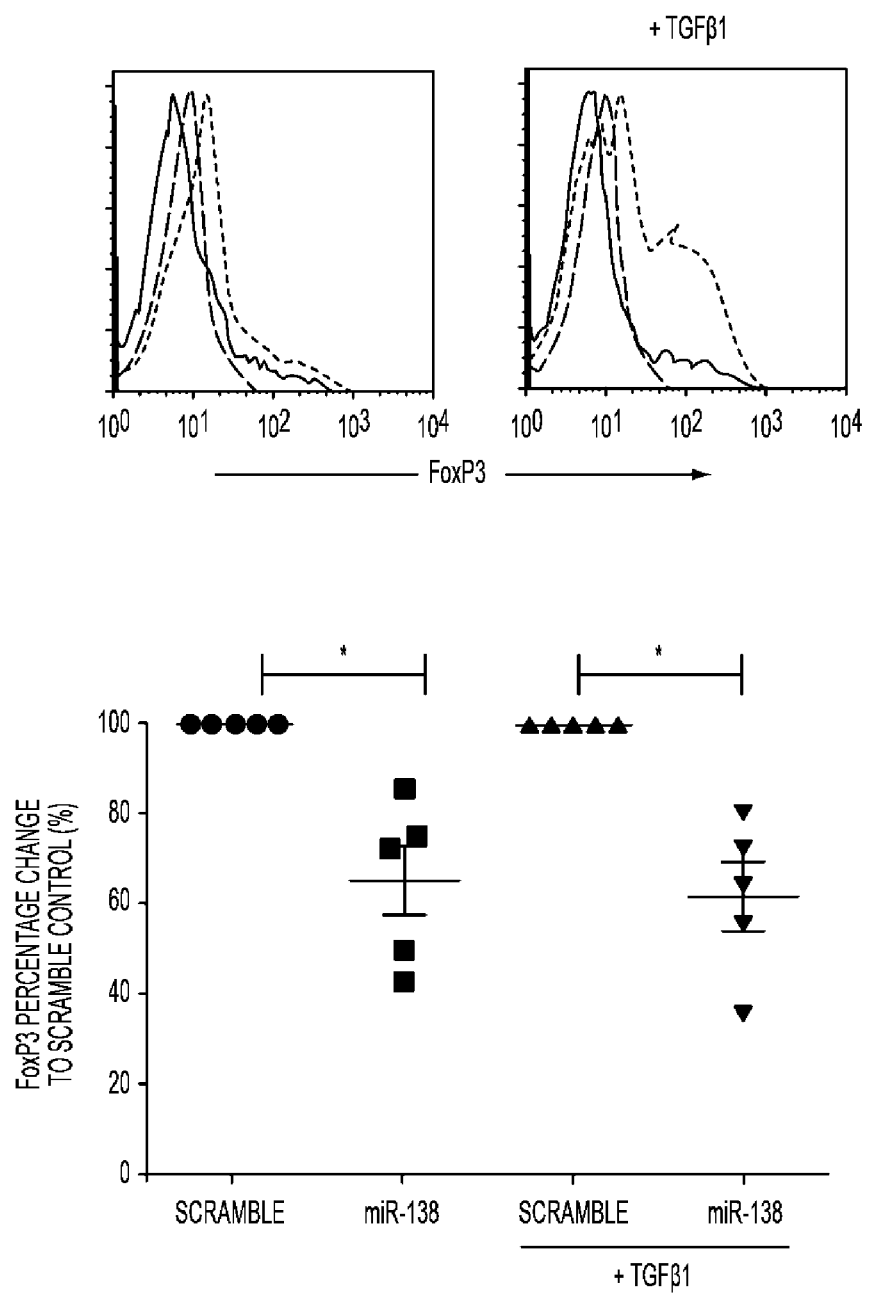

To determine the effects of miR-138 on the de novo synthesis of Tregs, miR-138 was transfected into human T cells during in vitro Treg induction with TGF-β1. miR-138 transfected T cells significantly down-regulated CTLA-4, PD-1 and FoxP3 expression compared to the scramble control (FIG. 26A-C). Since the mechanism of activity of ipilimumab has been shown to entail the activation of the ICOS/ICOSL pathway (an inducible co-stimulator) (Fu et al., 2011; Carthon et al., 2010; Chen et al., 2009) and the ICOS ligand is expressed by glioma cells (Schreiner et al., 2003), we evaluated if miR-138 would alter ICOS expression in human T cells but found that there was no difference after miR-138 transfection versus scramble control stimulated and un-stimulated CD4+ cells.

3. miR-138 Inhibits In Vivo Glioma Growth

Given the role of miR-138 in modulating the CTLA-4 and PD-1 pathways, we next determined whether miR-138 exerted a therapeutic effect in vivo. To assess the in vivo anti-tumor efficacy of miR-138, GL261 murine glioma cells were implanted into immune competent C57BL/6 mice and were treated with miR-138 or scramble control (n=10 per group). After the subcutaneous GL261 tumors had grown to a palpable size, miR-138 duplex or scramble control was administered. Subcutaneous tumor growth progressed in all the C57BL/6J mice treated with the scramble control. In contrast, in the miR-138-treated group, the tumor volume was markedly suppressed (P<0.05) (FIG. 27A). Gliomas started to shrink as soon as miR-138 was administered; moreover, the tumors continued to regress even after miR-138 treatment was discontinued. In contrast, tumors kept growing aggressively in scramble microRNA-treated and untreated tumor-bearing mice groups.

To ascertain if systemic administration of miR-138 had a therapeutic effect against established intracerebral gliomas, C57/BL6J mice with established GL261 tumors were treated with i.v. administered miR-138. In mice treated with miR-138 median survival was 33.5 days which compared favorably to mice treated with scramble control with a median survival of 23.5 days (P=0.011) (FIG. 27B). In the aggressive B16 murine model of intracranial melanoma, treatment with miR-138 increased median survival by 23%.

4. The Therapeutic Effect of miR-138 is Immune Mediated

Figure 28A:
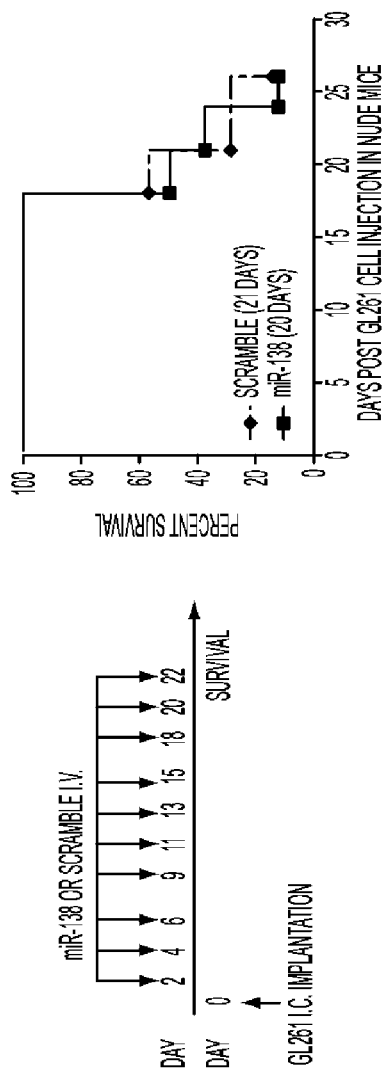
FIGS. 28A-B: The therapeutic effect of miR-138 is immune mediated.
Figure 28B:
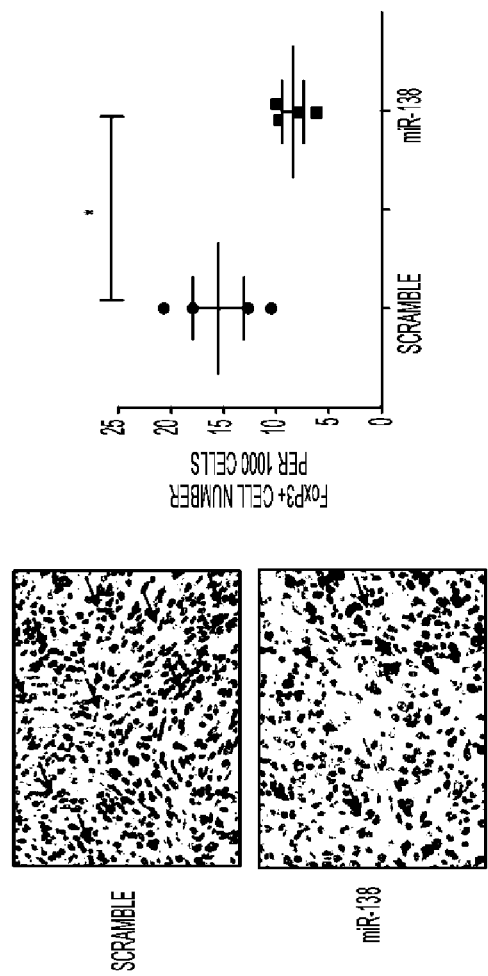

To determine if the therapeutic effect of miR-138 is immunologically mediated, nude mice were implanted with GL261 and subsequently treated with miR-138. In the immune-incompetent animal background, miR-138 failed to exert any therapeutic effect, indicating that miR-138 mediates in vivo activity via the immune system (FIG. 28A). Ex vivo analysis of the miR-138-treated GL261 gliomas from the immune competent mice demonstrated a marked reduction of FoxP3+ T cells by 51% relative to the scramble control (P=0.03) (FIG. 28B).

5. The PD-1 Ligand, PD-L1, is Expressed in Glioblastomas

Figure 30C:
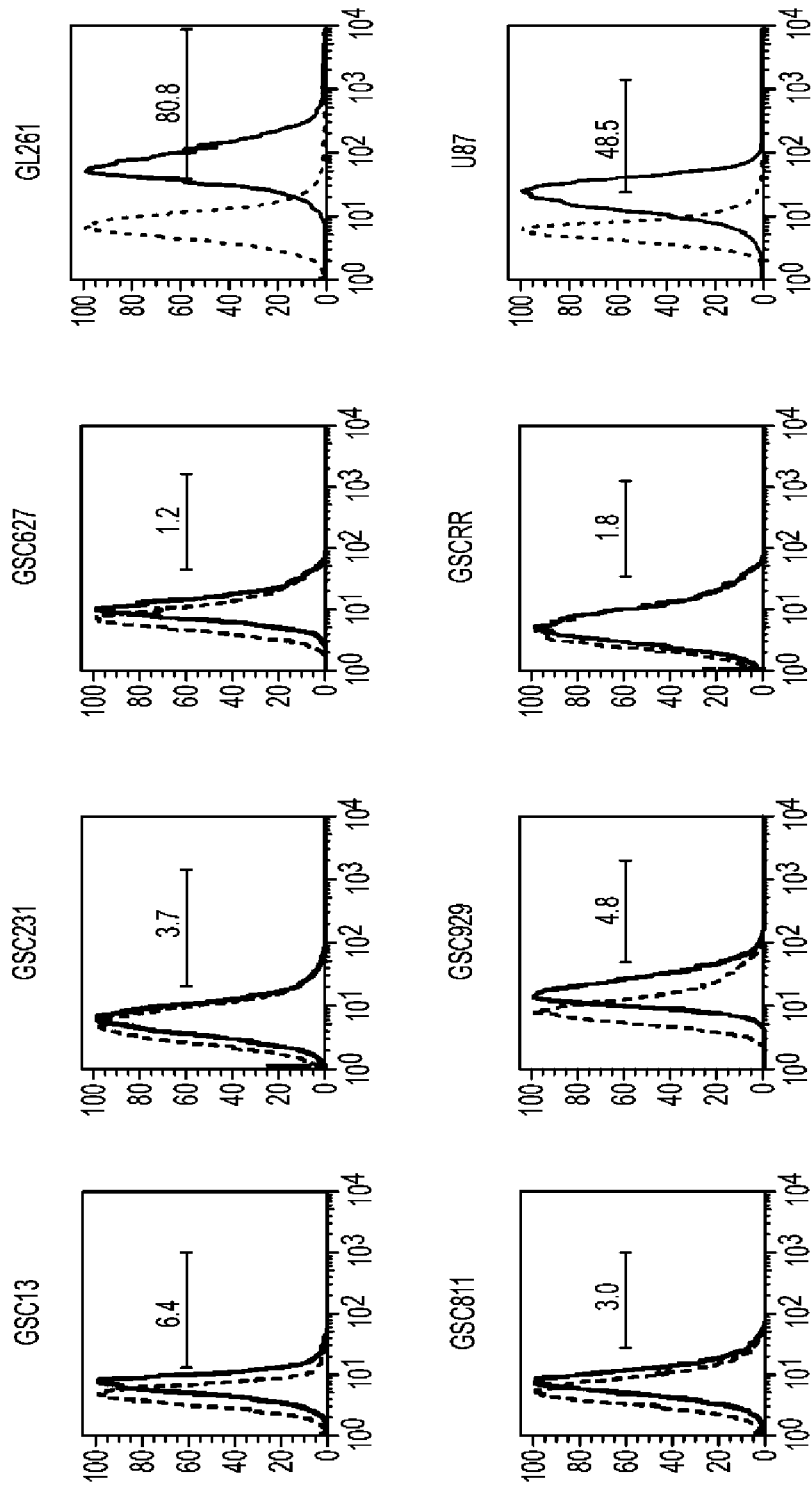

To determine if the overexpression of PD-L1 impacts the survival of glioblastoma patients, we analyzed expression relative to outcome using the TCGA database. The relative expression levels of PD-L1 were categorized by the upper and lower percentiles of expression, and there was a statistically significant difference between survival, with the patients with PD-L1 expression in the top $20^{th}$ percentile surviving longer than those in the bottom 20% of relative expression (FIG. 30B). To validate this data, the frequency of PD-L1 expression in gliomas and its prognostic impact were determined by immunohistochemical staining for PD-L1 on the glioblastoma TMA (FIG. 30A). We found that universally that almost all glioblastomas express PD-L1 expression. Furthermore, by direct ex vivo staining of glioblastomas by flow cytometry, most demonstrated positive PD-L1 expression. Since have previously demonstrated the glioblastoma cancer stem cells (gCSCs) are profoundly immune suppressive and since these cells can be infrequent within the overall tumor mass, we analyzed the expression of PD-L1 expression on gCSCs and found only low frequency of expression on rare gCSCs. However, PD-L1 is expressed on commonly used laboratory glioma cell lines such as GL261 and U87 (FIG. 30C).

Unlike many cancers such as melanoma, where immune therapy has made great strides over the years, immunotherapy for glioma has not yet matured into therapeutics capable of successful widespread translation to the clinic (Heimberger et al., 2011). Many reasons exist for this, including difficulties in scaling up production for many difficult and expensive processes as is the case of dendritic cell vaccines, challenges in clinical trial design, lack of interest in drug development for glioblastoma by pharmaceutical companies secondary to the rarity of the disease and barriers in drug delivery. Use of the microRNAs described herein may present an opportunity to sidestep many of these concerns. Their easy reproduction lowers costs, as above, and their biocompatibility may lower toxicity concerns. As shown in the above examples, two other miRNAs (i.e., miR-124 and miR-142-3p) down regulated in glioblastoma may be used therapeutically, e.g., by overcoming immune suppression by different mechanisms. Given the variable expression of immunosuppressive cells throughout the different subtypes of glioblastoma (Doucette et al., 2013), these miRNAs may be combined (e.g., miR-124, miR-142-3p, and/or miR-138) for further therapeutic synergy and comprehensive targeting of tumor-mediated immune suppression.

Example 4

Combination Therapies Involving miR-138 miR-142-3p, and/or miR-138

To assess whether these immune modulatory miRNAs would have an additive or synergistic therapeutic effect, we assessed all possible combinations and compared to monotherapy. C57BL/6J mice with established intracerebral GL261 gliomas were treated intravenously for 3 weeks on Monday, Wednesday, and Friday with 20 µg of each miRNA (scramble control, miR-124, miR-138, miR-142-3p, miR124+miR142-3p, miR124+miR138, miR142-3p+miR138, miR124+miR138+miR142-3p) in 48 µL of phosphate-buffered saline (PBS) mixed with the vehicle (40 µL PBS containing 10 µL LIPOFECTAMINE2000).

Figure 31:
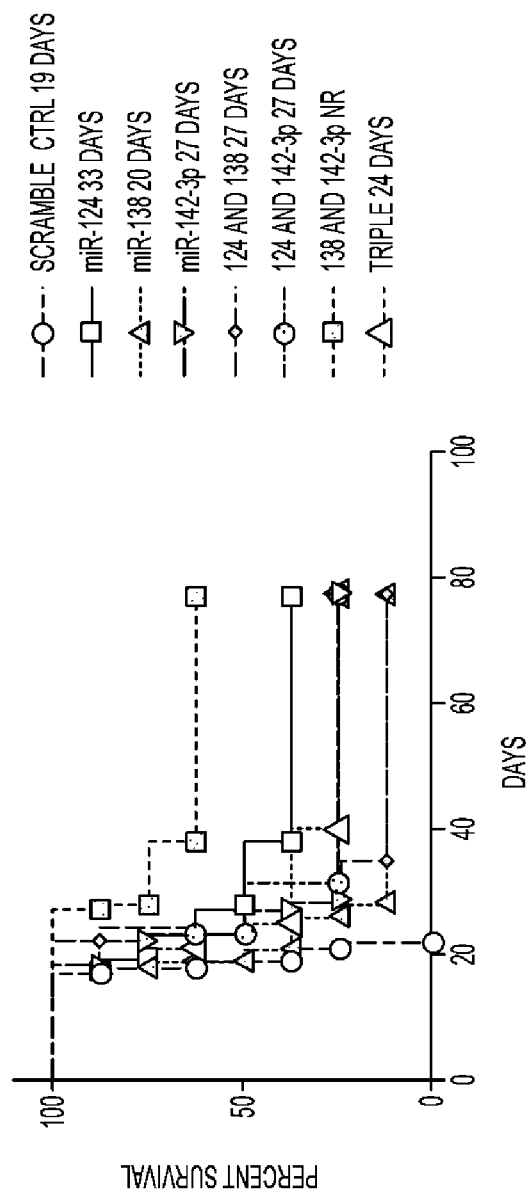
FIG. 31: Combination Therapies Involving miR-138 miR-142-3p, and/or miR-138.

Results are shown in FIG. 31. The study endpoint is median survival time. miR-124 was identified as the lead monotherapy and miR-138+miR142-3p the optimal combinatorial approach. More specifically, it appears that the CTLA-4 and PD-1 inhibition provided by miR-138 is synergistic with the TGFBR1 inhibition in immunosuppressive M2 macrophages provided by miR-142-3p. Complementary mechanistic studies are underway that will evaluate both the systemic and intratumoral immune responses that are modulated with this combinatorial approach.

Example 5

Formulations of Immune Modulatory miRNAs for Use in Cancer Patients

Figure 32:
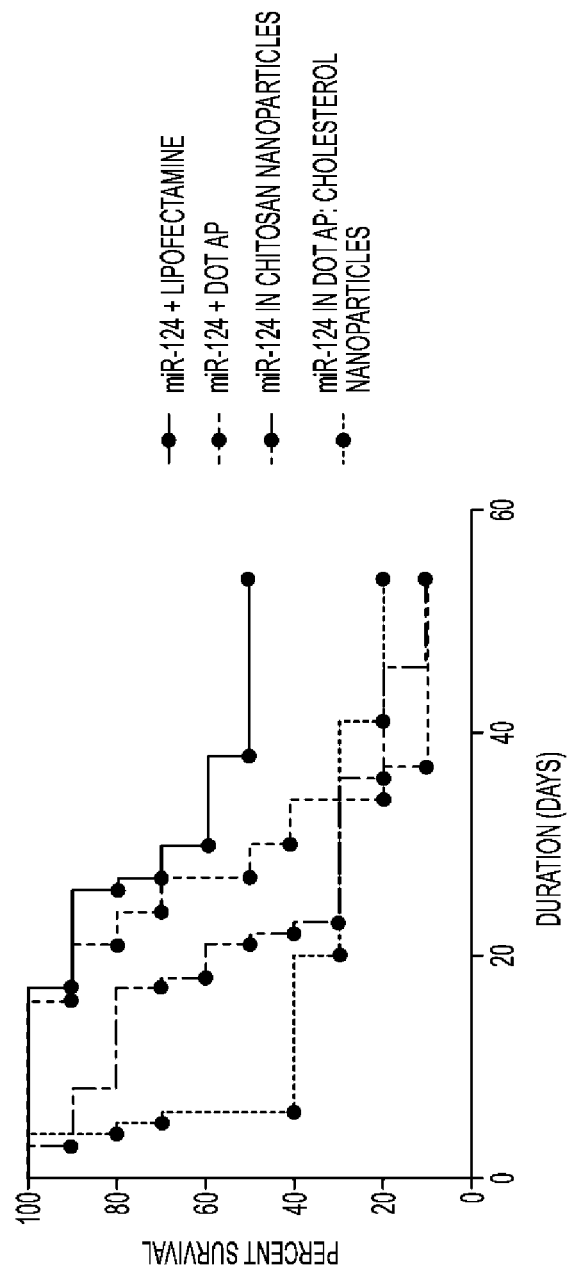
FIG. 32: Formulation equivalency studies of miRNA124 in nanoparticles. Graph of the Kaplan-Meier estimate demonstrating survival in the intracerebral GL261 intracerebral murine model treated with various formulations of miR-124.

We have conducted a number of formulation equivalency studies with miRNAs and found that co-administration with DOTAP was not satisfactory in comparison to LIPOFECTAMINE. MiR-124 chitosan nanoparticles were prepared on an ionic gelation of anionic tripolyphosphate. Furthermore, miR-124 DOTAP:cholesterol nanoparticles were created. Based on efficacy against intracranial GL261 glioma tumors, these constructs were not deemed to be sufficiently satisfactory for further translational development (FIG. 32). Further modifications were made to enhance the therapeutic delivery of miRNAs to the immune cell population.

Figure 33:
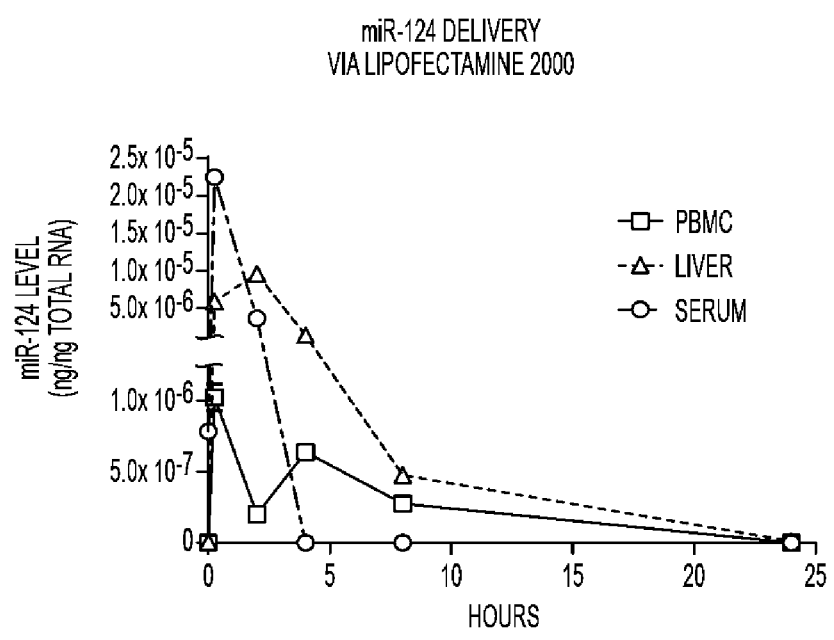
FIG. 33: Formulation equivalency studies and pharmacokinetics of immune modulatory miRNAs. Non-tumor bearing C57BL/6J mice were administered miR-124+ lipofectamine i.v. once and subsequently terminated at the designated time points. The liver, peripheral blood mononuclear cells (PBMCs) and serum were subsequently analyzed for miR-124 expression by quantitative PCR.

Specific formulation modifications were made in the lipid nanoparticles to potentially drive entry into the circulating immune cell population and to accommodate the miRNAs. To ascertain the pharmacokinetics and half-life of liposomes comprising miR-124 in vivo, non-tumor bearing C57BL/6J mice may be dosed at 1 mg/kg of the test article and the PBMC, liver and serum will be fractionated at various time points. Three animals will be used per each experimental time point of 0, 15 minutes, 1, 4, 8 and 24 hours. The comparator (positive control) will be miR-124 administered with LIPOFECTAMINE for which we have previously conducted this type of analysis (FIG. 32B). The miR-124 duplex that mimics pre-miR-124a (sense: 5'-UAAGGCACGCGGUGAAUGCCA-3' (SEQ ID NO:4), antisense: 3'-UAAUUCCGUGCGCCACUUACG-5' (SEQ ID NO:5)) is synthesized by SynGen, San Carlos, Calif. The treatment cohorts consisted of 20 µg of the miR-124 duplex in 10 µL of PBS mixed with the vehicle (80 µL PBS containing 10 µL LIPOFECTAMINE 2000; Invitrogen). Quantitative PCR may be used to assess the miRNA level in each compartment and it's in vivo half-life, similar to the previous analysis we have conducted for miR-124+LIPOFECTAMINE (FIG. 33).

Experiment 2

Figure 34:
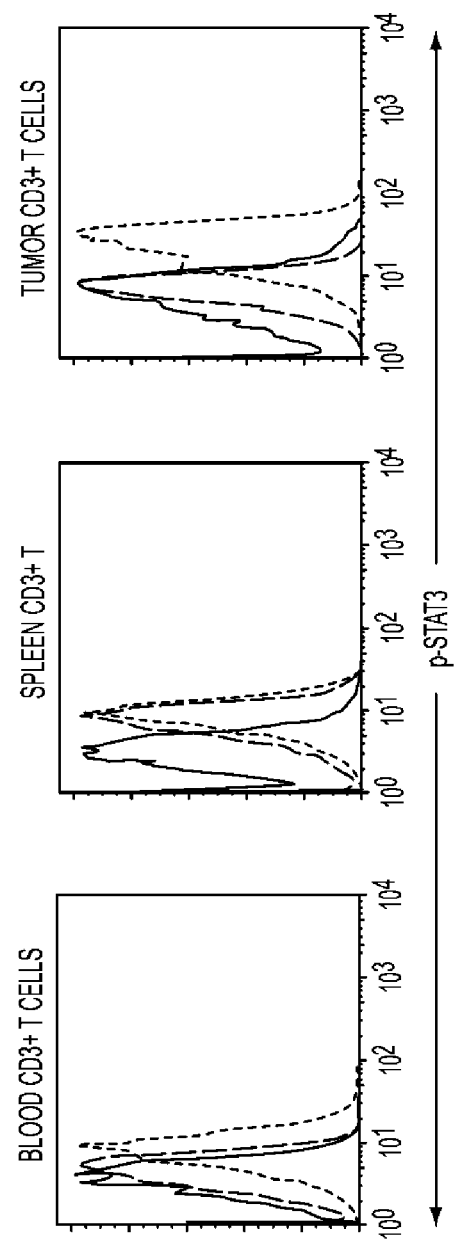
FIG. 34: p-STAT3 expression levels were decreased in the T-cells from the peripheral blood and gliomas in the miR-124 treated mice. Representative histograms were shown. The p-STAT3 expression levels relative to isotype control in the peripheral blood T-cells in the miR-124 treated mice (1.4±0.2%) was down-modulated compared to scramble treated mice (17.9±1.9%) (P=0.007; n=3) and glioma-infiltrating T-cells (miR-124: 4.3±0.1%; scramble: 18.2±4.3%; P=0.007), but not within the splenic T-cells (miR-124: 16.8±0.9%; scramble: 12.9±2.7%; P=0.07). The isotype is light grey dashed lines, the scramble miRNA control is the dashed black line and miR-124 is the solid grey line.

Ascertain if liposomes targeting the STAT3 pathway and has select immune modulatory properties. The inventors have shown that miR-124 can target multiple hubs within the STAT-3 signaling pathway. The levels of blood and spleen T cells have only modest expression of p-STAT3 even in tumor bearing animals. The highest levels of p-STAT3 were observed within the tumor microenvironment (FIG. 34).

C57BL/6J mice bearing subcutaneous GL261 cells may be treated by either miR-124+LIPOFECTAMINE 2000 (n=3 per group) or control liposomes for two weeks. For glioma-infiltrating T-cell isolation, the gliomas may be cut into small pieces and digested with Liberase™ for 2 hours at 37° C. to make a single-cell suspension for CD3+ T-cell selection using the CD3 negative selection kit (BD Biosciences). The purity of CD3+ T-cells is >94%. For intracellular p-STAT3 detection, the CD3+ T cells are first fixed with 2% paraformaldehyde at room temperature for 10 minutes. Thereafter, the cells were washed and permeabilized with 90% methanol on ice for 30 minutes, and then stained with PE-conjugated anti-p-STAT3 (Y705) antibody (BD Pharmingen) for 30 minutes at room temperature. The most robust immune modulatory endpoint was the inhibition of Tregs in the glioma microenvironment, and p-STAT3 is a transcriptional regulator of FoxP3. As a secondary endpoint, the T cells may also be stained with a PE-conjugated anti-FoxP3 antibody. Flow cytometry acquisition may be performed with a FACS CALIBUR (Becton Dickinson, San Diego, Calif.), and data will be analyzed with FLOWJO software (TreeStar, Ashland, Oreg.).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,034,506
U.S. Pat. No. 5,235,033
U.S. Pat. No. 5,399,363
U.S. Pat. No. 5,466,468
U.S. Pat. No. 5,466,468
U.S. Pat. No. 5,543,158
U.S. Pat. No. 5,629,001
U.S. Pat. No. 5,641,515
U.S. Pat. No. 5,756,353
U.S. Pat. No. 5,780,045
U.S. Pat. No. 5,804,212
U.S. Pat. No. 6,268,490
U.S. Pat. No. 6,613,308
U.S. Pat. No. 6,770,748
U.S. Patent Publication No. 2002/0115080
U.S. Patent Publication No. 2005/0107325
U.S. Patent Publication No. 2005/0182005
Allavena et al., *Cancer Res.* 2005; 65:2964-2971.
Bao et al., *Nature.* 2006; 444:756-60.
Barnett et al., *Clin Cancer Res.* 2007; 13:3559-67.
Behm-Ansmant et al., *Cold Spring Harb. Symp. Quant. Biol.,* 71:523-530, 2006.
Bharali et al. *PNAS* (2005) 102(32): 11539-11544
Bjorge et al., *PLoS One.* 2011; 6:e19309.
Bouquet et al., *Clin Cancer Res.* 2011; 17:6754-6765.
Brennecke et al., *Cell,* 113(1):25-36, 2003.
Cai et al., *Stem Cells.* 2012; 30:1746-55.
Calin et al., *Proc. Natl. Acad. Sci. USA,* 105:5166-5171, 2008.
Carrington and Ambros, *Science,* 301(5631):336-338, 2003.
Carthon et al., *Clin Cancer Res.* 2010; 16:2861-71.
Chan et al., *Cancer Res.* 2005; 65:6029-33.
Chan et al., *Cell Cycle.* 2011; 10:1845-1852.
Chan et al., *Cell Rep.* 2012; 2:591-602.
Chen and Okayama, *Mol. Cell Biol.,* 7(8):2745-2752, 1987.
Chen et al., *J Leukoc Biol.* 2008; 83:1165-1173.
Chen et al., *Mol. Microbiol.,* 53843-856, 2004.
Chen et al., *PLoS ONE,* 6, 2011.
Chen et al., *Proc Natl Acad Sci USA.* 2009; 106:2729-34.
Chen, *Science,* 303:2022-2025, 2004.
Chihara et al., *J Immunol.* 2012; 188:3620-3627.
Chu and Rana, *Plos. Biology.,* 4:e210, 2006.
Corsten et al., *Cancer Res.* 2007; 67:8994-9000.
Dai et al., *Cancer Res.* 2011; 71:3658-68.
Dai et al., *Genes Dev.* 2001; 15:1913-1925.
Dostie et al., *Rna-A Publication of the Rna Society,* 9:180-186, 2003.
Doucette et al., *Cancer Immunol Res.* 2013; 1:112-22.
Doucette et al., *Neuro Oncol.,* 2012; 14:1136-45.
Eulalio et al., *Cell,* 132:9-14, 2008.
Fecci et al., *Clin Cancer Res.* 2007; 13:2158-67.
Flavell et al., *Nat Rev Immunol.* 2010; 10:554-567.
Friedman et al., *Genome Res.,* 19:92-105, 2009.
Fu et al., *Cancer Res.* 2011; 71:5445-54.
Gabriely et al., *Mol Cell Biol.* 2008; 28:5369-80.
Gaur et al., *Neuro Oncol.* 2011; 13:580-90.
Giraudo et al., *J Clin Invest.* 2004; 114:623-633.
Halder et al., *Neoplasia.* 2005; 7:509-521.
Hardee et al., *Cancer Res.* 2012; 72:4119-4129.
Hashimoto et al., *Blood.* 1999; 94:837-844.
Hatziapostolou et al., *Cell.* 2011; 147:1233-47.
Heimberger et al., *Clin Cancer Res.* 2003; 9:4247-4254.
Heimberger et al., *Neuro Oncol.* 2011; 13:3-13.
Heusinkveld et al., *J Transl Med.* 2011; 9:216.
Hjelmeland et al., *Mol Cancer Ther.* 2004; 3:737-745.
Hui et al., *Clin Cancer Res.* 2010; 16:1129-1139.
Huse et al., *Brain Pathol.* 2009; 19:132-143.
Hussain et al., *Neuro Oncol.* 2006; 8:261-279.
Iliopoulos et al., *Mol Cell.* 2010; 39:493-506.
Inman et al., *Mol Pharmacol.* 2002; 62:65-74.
Inoue et al., *Oncol Rep.* 2012; 27:1759-1764.
Jarkowski et al., *J Oncol Pharm Pract.* 2013.
Jensen et al., *J Clin Oncol.* 2009; 27:3330-3337.
Kong et al., *Clin Cancer Res.* 2010; 16:5722-33.
Kortylewski et al., *Nat Biotechnol.* 2009; 27:925-32.
Kortylewski et al., *Nat Med.* 2005; 11:1314-21.
Krausgruber et al., *Nat Immunol.* 2011; 12:231-238.
Krutzfeldt et al., *Nature,* 438(7068):685-689, 2005.
Lim et al., *Nature.* 2005; 433:769-73.
Linde et al., *J Pathol.* 2012; 227:17-28.
Loffler et al., *Blood.* 2007; 110:1330-3.
Lu et al. (*Cancer Cell* (2010) 18:185-197)
Lujambio et al., *Cancer Res.* 2007; 67:1424-9.
Lv et al., *Leukemia.* 2012; 26:769-777.
Magrassi et al., *Oncogene.* 2005; 24:5198-206.
Metzler et al., *Genes Chromosomes Cancer,* 39:167-169, 2004.
Michael et al., *Mol. Cancer Res.,* 1:882-891, 2003.
Muraoka et al., *J Clin Invest.* 2002; 109:1551-1559.
Murray et al., *Biochem Soc Trans.* 2006; 34:1028-31.
Namlos et al., *PLoS One.* 2012; 7:e48086.
Nuovo et al., *Nat Protoc.* 2009; 4:107-15.
Onco-Path siRNA Library—Overview. 2013; Available from: avetrabiocom.ipage.com/1701.html
Pander et al., *Clin Cancer Res.* 2011; 17:5668-5673.
Pfeffer et al., *Science,* 304:734-736, 2004.
Pinheiro et al., *Science,* 336(6079):341-344, 2012.
Ponomarev et al., *Nat Med.* 2011; 17:64-70.
Pramanik et al. *Mol Cancer Ther* (2011) 10:1470-1480
Puig-Kroger et al., *Cancer Res.* 2009; 69:9395-9403.
Reinhart et al., *Nature,* 403:901-906, 2000.
Robinson et al., *Cancer Res.* 2003; 63:8360-8365.
Schreiner et al., *GLIA.* 2003; 44:296-301.
Scuto et al., *Cancer Res.* 2011; 71:3182-8.
Seth et al., *J. Med. Chem.,* 52(1): 10-13, 2009.
Seth et al., *Nucleic Acids Symp. Ser.* (Oxford), 52:553-554, 2008.
Sierra-Filardi et al., *Blood.* 2011; 117:5092-5101.
Soutschek et al., *Nature,* 432:173-178, 2004.
Stupp et al., *N Engl J Med.* 2005; 352:987-996.
Teplova et al., *Nat. Struct. Biol.,* 6:535-539, 1999.

Veedu et al., *Bioorganic Med. Chem. Lett.*, 20(22):6565-6568, 2010.
Vogt et al., *Cell Signal.* 2011; 23:1831-1842.
Wang et al., *Mol Biol Rep.* 2012; 39:2713-2722.
Wei et al., *Cancer Res.* 2013; 73:3913-26.
Wei et al., *Clin Cancer Res.* 2010; 16:461-73.
Wei et al., *Mol Cancer Ther.* 2010; 9:67-78.
Wu et al., *FEBS Lett.* 2011; 585:1322-1330.
Wu et al., *Neuro Oncol.* 2010; 12:1113-25.
Xu et al., *Curr. Biol.,* 13(9):790-795, 2003.
Zhao et al., *Cell,* 129:303-317, 2007.
Zhou et al., *Lab Invest.* 2010; 90:144-55.

The invention claimed is:

1. A method of inducing an anti-cancer immune response in a subject, comprising administering to immune cells of said subject a pharmaceutically effective amount of a nucleic acid composition comprising a miR-124, a miR-142, or a miR-138 nucleic acid sequence in an amount sufficient to induce, enhance, or promote an immune response against the cancer in the subject.

2. The method of claim 1, wherein the immune cells comprise T-cells, natural killer (NK) cells, or dendritic cells.

3. The method of claim 1, wherein the immune cells are contacted in vivo.

4. The method of claim 3, wherein the nucleic acid composition is administered parenterally to the subject.

5. The method of claim 4, wherein the nucleic acid composition is administered to the subject intradermally, intravenously, intraarterially, intrathecally, intraperitoneally, intramuscularly, or by injection into a surgical/resection cavity.

6. The method of claim 3, wherein the nucleic acid composition is administered to the subject via an aerosol.

7. The method of claim 1, wherein the immune cells are contacted with the nucleic acid composition ex vivo in an amount sufficient to immunologically prime the immune cells, and the immunologically primed immune cells are subsequently administered to the patient.

8. The method of claim 1, wherein miR-124 is administered to the immune cells.

9. The method of claim 1, wherein miR-142 is administered to the immune cells.

10. The method of claim 1, wherein miR-138 is administered to the immune cells.

11. The method of claim 1, wherein the nucleic acid is a modified nucleic acid.

12. The method of claim 11, wherein the nucleic acid is a LNA.

13. The method of claim 1, wherein the nucleic acid is an unmodified nucleic acid.

14. The method of claim 1, wherein the cancer is selected from the group consisting of a brain cancer, a glioma, a neuroblastoma, a medulloblastoma, a glioblastoma, an astrocytoma, or a melanoma.

15. The method of claim 14, wherein the cancer is a brain cancer, a glioma, a neuroblastoma, or glioblastoma.

16. The method of claim 1, wherein the nucleic acid comprises a phosphoramidate linkage, a phosphorothioate linkage, a phosphorodithioate linkage, or an O-methylphosphoroamidite linkage.

17. The method of claim 1, wherein said nucleic acid comprises one or more nucleotide analogs.

18. The method of claim 1, wherein the subject is a mammal.

19. The method of claim 18, wherein the mammal is a human.

20. The method of claim 18, further comprising administering to the subject a chemotherapy, immunotherapy, radiotherapy, cytokine therapy, or surgery.

21. The method of claim 20, wherein an immunotherapy is administered to the subject.

22. The method of claim 21, wherein the immunotherapy is an adoptive immunotherapy.

23. The method of claim 22, wherein the adoptive immunotherapy comprises a T-cell immunotherapy, a natural killer (NK) cell immunotherapy, or a dendritic cell immunotherapy, a viral immunotherapy, or an adoptive T-cell transfer.

24. The method of claim 21, wherein the immunotherapy comprises administration of a monoclonal antibody, interleukin 2 (IL-2), or gamma interferon to the subject.

25. The method of claim 24, wherein a monoclonal antibody is administered to the subject, wherein the monoclonal antibody selectively targets an immune checkpoint or immune suppressive pathway or mechanism.

26. The method of claim 1, wherein said nucleic acid is comprised in a vector.

27. The method of claim 26, wherein said vector is a viral vector.

28. The method of claim 27, wherein said viral vector is an adenovirus, an adeno-associated virus, a lentivirus, or a herpes virus.

29. The method of claim 26, wherein said vector comprises a lipid, lipid emulsion, liposome, nanoparticle, or exosomes.

30. The method of claim 29, wherein the miRNA is comprised in a liposome, nanoparticle, or exosome.

31. The method of claim 29, wherein the miRNA is comprised in a liposome, wherein the liposome comprises N-[1-(2,3-Dioleoyloxy)propyl]-N,N,N-trimethylammonium methyl-sulfate (DOTAP) or Lipofectamine™.

32. The method of claim 29, wherein the miRNA is comprised in a nanoparticle, wherein the nanoparticle comprises silicone.

33. A method of treating a cancer in an individual, comprising
(a) contacting T-cells, natural killer (NK) cells, or dendritic cells to be used in an adoptive therapy with a synthetic or recombinant miR-124, miR-142, or miR-138 in an amount sufficient to promote or enhance the function or proliferation of the cells; and
(b) administering the T-cells, natural killer (NK) cells, or dendritic cells to the individual.

* * * * *

UNITED STATES PATENT AND TRADEMARK OFFICE
CERTIFICATE OF CORRECTION

PATENT NO. : 9,675,633 B2
APPLICATION NO. : 14/775667
DATED : June 13, 2017
INVENTOR(S) : Heimberger et al.

Page 1 of 1

It is certified that error appears in the above-identified patent and that said Letters Patent is hereby corrected as shown below:

In Column 1, Lines 10-13, delete the paragraph and insert --This invention was made with government support under grant numbers R01 CA120813, P50 CA127001, and P50 CA093459 awarded by the National Institutes of Health. The government has certain rights in the invention.-- therefor.

Signed and Sealed this
Second Day of October, 2018

Andrei Iancu
*Director of the United States Patent and Trademark Office*